(12) United States Patent
Eggenweiler et al.

(10) Patent No.: US 8,546,565 B2
(45) Date of Patent: *Oct. 1, 2013

(54) QUINAZOLINAMIDE DERIVATIVES

(75) Inventors: Hans-Michael Eggenweiler, Darmstadt (DE); Christian Sirrenberg, Darmstadt (DE); Hans-Peter Buchstaller, Griesheim (DE)

(73) Assignee: Merck Patent Gesellschaft, Darmstadt (DE)

(*) Notice: Subject to any disclaimer, the term of this patent is extended or adjusted under 35 U.S.C. 154(b) by 253 days.

This patent is subject to a terminal disclaimer.

(21) Appl. No.: 13/133,495

(22) PCT Filed: Nov. 12, 2009

(86) PCT No.: PCT/EP2009/008061
§ 371 (c)(1),
(2), (4) Date: Jun. 8, 2011

(87) PCT Pub. No.: WO2010/066324
PCT Pub. Date: Jun. 17, 2010

(65) Prior Publication Data
US 2011/0245225 A1    Oct. 6, 2011

(30) Foreign Application Priority Data
Dec. 9, 2008 (DE) .................... 10 2008 061 214

(51) Int. Cl.
*C07D 239/70* (2006.01)
*A01N 43/54* (2006.01)

(52) U.S. Cl.
USPC ............... 544/253; 514/258.1; 514/266.1

(58) Field of Classification Search
None
See application file for complete search history.

(56) References Cited

U.S. PATENT DOCUMENTS

2008/0214586 A1   9/2008 Eggenweiler et al.
2008/0280878 A1  11/2008 Castro et al.
2010/0234324 A1   9/2010 Eggenweiler et al.

FOREIGN PATENT DOCUMENTS

| GB | 2449293 A | 11/2008 |
| WO | 2006050457 A2 | 5/2006 |
| WO | 2006113498 A2 | 10/2006 |
| WO | 2006122631 A1 | 11/2006 |
| WO | 2009010139 A2 | 1/2009 |

OTHER PUBLICATIONS

Maria Mbura,"Health Article on Cancer" Mar. 27, 2008, p. 1.*
World IP Organization. "International Search Report". PCT/EP2009/008061, Applicant: Merck Patent GMBH, Mailed: Jan. 21, 2010.

* cited by examiner

*Primary Examiner* — James O Wilson
*Assistant Examiner* — Oluwafemi Masha
(74) *Attorney, Agent, or Firm* — Millen, White, Zelano & Branigan, P.C.

(57) ABSTRACT

Novel quinazolinamide derivatives of the formula (I), in which $R^1$-$R^5$ and X have the meanings indicated in Claim 1, are HSP90 inhibitors and can be used for the preparation of a medicament for the treatment of diseases in which the inhibition, regulation and/or modulation of HSP90 plays a role.

23 Claims, No Drawings

QUINAZOLINAMIDE DERIVATIVES

BACKGROUND OF THE INVENTION

The invention was based on the object of finding novel compounds having valuable properties, in particular those which can be used for the preparation of medicaments.

The present invention relates to compounds in which the inhibition, regulation and/or modulation of HSP90 plays a role, furthermore to pharmaceutical compositions which comprise these compounds, and to the use of the compounds for the treatment of diseases in which HSP90 plays a role.

The correct folding and conformation of proteins in cells is ensured by molecular chaperones and is critical for the regulation of the equilibrium between protein synthesis and degradation. Chaperones are important for the regulation of many central functions of cells, such as, for example, cell proliferation and apoptosis (Jolly and Morimoto, 2000; Smith et al., 1998; Smith, 2001).

Heat Shock Proteins (HSPs)

The cells of a tissue react to external stress, such as, for example, heat, hypoxia, oxidative stress, or toxic substances, such as heavy metals or alcohols, with activation of a number of chaperones which are known under the term "heat shock proteins" (HSPs).

The activation of HSPs protects the cell against damage initiated by such stress factors, accelerates the restoration of the physiological state and results in a stress-tolerant state of the cell.

Besides this originally discovered protective mechanism promoted by HSPs against external stress, further important chaperone functions have also been described in the course of time for individual HSPs under normal stress-free conditions. Thus, various HSPs regulate, for example, correct folding, intracellular localisation and function or regulated degradation of a number of biologically important proteins of cells.

HSPs form a gene family with individual gene products whose cellular expression, function and localisation differs in different cells. The naming and classification within the family is carried out on the basis of their molecular weight, for example HSP27, HSP70, and HSP90.

Some human diseases are based on incorrect protein folding (see review, for example, Tytell et al., 2001; Smith et al., 1998). The development of therapies which engages in the mechanism of the chaperone-dependent protein folding could therefore be useful in such cases. For example, incorrectly folded proteins result in aggregation of protein with neurodegenerative progression in the case of Alzheimer's disease, prion diseases or Huntington's syndrome. Incorrect protein folding may also result in loss of wild-type function, which can have the consequence of incorrectly regulated molecular and physiological function.

HSPs are also ascribed great importance in tumour diseases. There are, for example, indications that the expression of certain HSPs correlates with the stage of progression of tumours (Martin et al., 2000; Conroy et al., 1996; Kawanishi et al., 1999; Jameel et al., 1992; Hoang et al., 2000; Lebeau et al., 1991).

The fact that HSP90 plays a role in a number of central oncogenic signalling pathways in the cell and certain natural products having cancer-inhibiting activity target HSP90 has led to the concept that inhibition of the function of HSP90 would be sensible in the treatment of tumour diseases. An HSP90 inhibitor, 17-allylamino-17-demethoxygeldanamycin (17AAG), a derivative of geldanamycin, is currently undergoing clinical trials.

HSP90

HSP90 represents approximately 1-2% of the total cellular protein mass. It is usually in the form of a dimer in the cell and is associated with a multiplicity of proteins, so-called co-chaperones (see, for example, Pratt, 1997). HSP90 is essential for the vitality of cells (Young et al., 2001) and plays a key role in the response to cellular stress by interaction with many proteins whose native folding has been modified by external stress, such as, for example, heat shock, in order to restore the original folding or to prevent aggregation of the proteins (Smith et al., 1998).

There are also indications that HSP90 is of importance as buffer against the effects of mutations, presumably through correction of incorrect protein folding caused by the mutation (Rutherford and Lindquist, 1998).

In addition, HSP90 also has a regulatory importance. Under physiological conditions, HSP90, together with its homologue in the endoplasmatic reticulum, GRP94, plays a role in the cell balance for ensuring the stability of the conformation and maturing of various client key proteins. These can be divided into three groups: receptors for steroid hormones, Ser/Thr or tyrosine kinases (for example ERBB2, RAF-1, CDK4 and LCK) and a collection of various proteins, such as, for example, mutated p53 or the catalytic subunit of telomerase hTERT. Each of these proteins takes on a key role in the regulation of physiological and biochemical processes of cells. The preserved HSP90 family in humans consists of four genes, cytosolic HSP90α, the inducible HSP90β isoform (Hickey et al., 1989), GRP94 in the endoplasmatic reticulum (Argon et al., 1999) and HSP75/TRAP1 in the mitochondrial matrix (Felts et al., 2000). It is assumed that all members of the family have a similar mode of action, but, depending on their localisation in the cell, bind to different client proteins. For example, ERBB2 is a specific client protein of GRP94 (Argon et al., 1999), while the type 1 receptor of tumour necrosis factor (TNFR1) or the retinoblastoma protein (Rb) have been found to be clients of TRAP1 (Song et al., 1995; Chen et al., 1996).

HSP90 is involved in a number of complex interactions with a large number of client proteins and regulatory proteins (Smith, 2001). Although precise molecular details have not yet been clarified, biochemical experiments and investigations with the aid of X-ray crystallography in recent years have increasingly been able to decipher details of the chaperone function of HSP90 (Prodromou et al., 1997; Stebbins et al., 1997). Accordingly, HSP90 is an ATP-dependent molecular chaperone (Prodromou et al, 1997), with dimerisation being important for ATP hydrolysis. The binding of ATP results in the formation of a toroidal dimer structure, in which the two N-terminal domains come into close contact with one another and act as a switch in the conformation. (Prodromou and Pearl, 2000).

Known HSP90 Inhibitors

The first class of HSP90 inhibitors to be discovered were benzoquinone ansamycins with the compounds herbimycin A and geldanamycin. Originally, the reversion of the malignant phenotype in fibroblasts which had been induced by transformation with the v-Src oncogene was detected with them (Uehara et al., 1985).

Later, a strong antitumoural activity was demonstrated in vitro (Schulte et al., 1998) and in vivo in animal models (Supko et al., 1995).

Immune precipitation and investigations on affinity matrices then showed that the principal mechanism of action of geldanamycin involves binding to HSP90 (Whitesell et al., 1994; Schulte and Neckers, 1998). In addition, X-ray crystallographic studies have shown that geldanamycin competes for the ATP binding site and inhibits the intrinsic ATPase activity of HSP90 (Prodromou et al., 1997; Panaretou et al., 1998). This prevents the formation of the multimeric HSP90 complex, with its property of functioning as chaperone for client proteins. As a consequence, client proteins are degraded via the ubiquitin-proteasome pathway.

The geldanamycin derivative 17-allylamino-17-demethoxygeldanamycin (17AAG) showed an unchanged property in the inhibition of HSP90, the degradation of client proteins and antitumoural activity in cell cultures and in xenograft tumour models (Schulte et al, 1998; Kelland et al, 1999), but had significantly lower liver cytotoxicity than geldanamycin (Page et al. 1997). 17AAG is currently undergoing phase I/II clinical trials.

Radicicol, a macrocyclic antibiotic, likewise exhibited revision of the v-Src and v-Ha-Ras-induced malignant phenotype of fibroblasts (Kwon et al 1992; Zhao et al, 1995). Radicicol degrades a large number of signal proteins as a consequence of HSP90 inhibition (Schulte et al., 1998). X-ray crystallographic studies have shown that radicicol likewise binds to the N-terminal domain of HSP90 and inhibits the intrinsic ATPase activity (Roe et al., 1998).

As is known, antibiotics of the coumarine type bind to the ATP binding site of the HSP90 homologue DNA gyrase in bacteria. The coumarine, novobiocin, binds to the carboxy-terminal end of HSP90, i.e. to a different site in HSP90 than the benzoquinone-ansamycins and radicicol, which bind to the N-terminal end of HSP90. (Marcu et al., 2000b).

The inhibition of HSP90 by novobiocin results in degradation of a large number of HSP90-dependent signal proteins (Marcu et al., 2000a).

The degradation of signal proteins, for example ERBB2, was demonstrated using PU3, an HSP90 inhibitor derived from purines. PU3 causes cell cycle arrest and differentiation in breast cancer cell lines (Chiosis et al., 2001).

HSP90 as Therapeutic Target

Due to the participation of HSP90 in the regulation of a large number of signalling pathways which are of crucial importance in the phenotype of a tumour, and the discovery that certain natural products exert their biological effect through inhibition of the activity of HSP90, HSP90 is currently being tested as a novel target for the development of a tumour therapeutic agent (Neckers et al., 1999).

The principal mechanism of action of geldanamycin, 17AAG, and radicicol includes the inhibition of the binding of ATP to the ATP binding site at the N-terminal end of the protein and the resultant inhibition of the intrinsic ATPase activity of HSP90 (see, for example, Prodromou et al., 1997; Stebbins et al., 1997; Panaretou et al., 1998). Inhibition of the ATPase activity of HSP90 prevents the recruitment of co-chaperones and favours the formation of an HSP90 heterocomplex, which causes client proteins to undergo degradation via the ubiquitin-proteasome pathway (see, for example, Neckers et al., 1999; Kelland et al., 1999). The treatment of tumour cells with HSP90 inhibitors results in selective degradation of important proteins having fundamental importance for processes such as cell proliferation, regulation of the cell cycle and apoptosis. These processes are frequently deregulated in tumours (see, for example, Hostein et al., 2001).

An attractive rationale for the development of an inhibitor of HSP90 is that a strong tumour-therapeutic action can be achieved by simultaneous degradation of a plurality of proteins which are associated with the transformed phenotype.

In detail, the present invention relates to compounds which inhibit, regulate and/or modulate HSP90, to compositions which comprise these compounds, and to methods for the use thereof for the treatment of HSP90-induced diseases, such as tumour diseases, viral diseases, such as, for example, hepatitis B (Waxman, 2002); immune suppression in transplants (Bijlmakers, 2000 and Yorgin, 2000); inflammation-induced diseases (Bucci, 2000), such as rheumatoid arthritis, asthma, multiple sclerosis, type 1 diabetes, lupus erythematosus, psoriasis and inflammatory bowel disease; cystic fibrosis (Fuller, 2000); diseases associated with angiogenesis (Hur, 2002 and Kurebayashi, 2001), such as, for example, diabetic retinopathy, haemangiomas, endometriosis and tumour angiogenesis; infectious diseases; autoimmune diseases; ischaemia; promotion of nerve regeneration (Rosen et al., WO 02/09696; Degranco et al., WO 99/51223; Gold, U.S. Pat. No. 6,210,974 B1); fibrogenetic diseases, such as, for example, scleroderma, polymyositis, systemic lupus, cirrhosis of the liver, keloid formation, interstitial nephritis and pulmonary fibrosis (Strehlow, WO 02/02123).

The invention also relates to the use of the compounds according to the invention for the protection of normal cells against toxicity caused by chemotherapy, and to the use in diseases where incorrect protein folding or aggregation is a principal causal factor, such as, for example, scrapie, Creutzfeldt-Jakob disease, Huntington's or Alzheimer's (Sittler, Hum. Mol. Genet., 10, 1307, 2001; Tratzelt et al., Proc. Nat. Acad. Sci., 92, 2944, 1995; Winklhofer et al., J. Biol. Chem., 276, 45160, 2001).

WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease.

WO 01/72779 furthermore discloses the use of the compounds mentioned therein for the treatment of viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type I (HIV-I) and human immunodeficiency virus type II (HIV-II).

WO 01/72779 furthermore describes the use of the compounds mentioned therein for GRP94 modulation, where the modulated biological GRP94 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Finally, WO 01/72779 describes the use of an effective amount of a GRP94 protein modulator for the preparation of a medicament for changing a subsequent cellular reaction to an ischaemic state in a tissue site in an individual, by treatment of the cells at the tissue site with the GRP94 protein modulator in order that the GRP94 activity in cells is increased to such an extent that a subsequent cellular reaction to an ischaemic state is changed, where the subsequent ischaemic condition is preferably the consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress, or where the tissue site is the donor tissue for a transplant.

A. Kamal et al. in Trends in Molecular Medicine, Vol. 10 No. 6 Jun. 2004, describe therapeutic and diagnostic applications of HSP90 activation, inter alia for the treatment of diseases of the central nervous system and of cardiovascular diseases.

The identification of small compounds which specifically inhibit, regulate and/or modulate HSP90 is therefore desirable and an aim of the present invention.

It has been found that the compounds according to the invention and salts thereof have very valuable pharmacological properties while being well tolerated.

In particular, they exhibit HSP90-inhibiting properties.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammalian species, for example a primate species, particularly humans; rodents, including mice, rats and hamsters; rabbits; horses, cows, dogs, cats, etc. Animal models are of interest for experimental investigations, where they provide a model for the treatment of a human disease.

PRIOR ART

WO 00/53169 describes HSP90 inhibition using coumarine or a coumarine derivative.

WO 03/041643 A2 discloses HSP90-inhibiting zearalanol derivatives. HSP90-inhibiting indazole derivatives are known from WO 06/010595 and WO 02/083648.

FURTHER LITERATURE

Argon Y and Simen B B. 1999 "Grp94, an ER chaperone with protein and peptide binding properties", Semin. Cell Dev. Biol., Vol. 10, pp. 495-505.

Bijlmakers M-J J E, Marsh M. 2000 "Hsp90 is essential for the synthesis and subsequent membrane association, but not the maintenance, of the Src-kinase p56Ick", Mol. Biol. Cell, Vol. 11(5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", Brit. J. Pharmacol., Vol 131(1), pp. 13-16.

Carreras C W, Schirmer A, Zhong Z, Santi V S. 2003 "Filter binding assay for the geldanamycin-heat shock protein 90 interaction", Analytical Biochem., Vol 317, pp 40-46.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", Mol. Cell. Biol., Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", Chem. Biol., Vol. 8, pp. 289-299.

Chiosis G, Lucas B, Shtil A, Huezo H, Rosen N 2002 "Development of a purine-scaffold novel class of HSP90 binders that inhibit the proliferation of cancer cells and induce the degradation of her2 tyrosine kinase". Bioorganic Med. Chem., Vol 10, pp 3555-3564.

Conroy S E and Latchman D S. 1996 "Do heat shock proteins have a role in breast cancer?", Brit. J. Cancer, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", J. Biol. Chem., Vol. 5, pp. 3305-331 2.

Fuller W, Cuthbert A W. 2000 "Post-translational disruption of the delta F508 cystic fibrosis transmembrane conductance regulator (CFTR)-molecular Chaperone complex with geldanamycin stabilises delta F508 CFTR in the rabbit reticulocyte lysate", J. Biol. Chem., Vol. 275(48), pp. 37462-37468.

Hickey E, Brandon S E, Smale G, Lloyd D and Weber L A. 1999 "Sequence and regulation of a gene encoding a human 89-kilodalton heat shock protein", Mol. Cell. Biol., Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor 1 (HSF1) and prostate adenocarcinoma, Am. J. Pathol., Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", Cancer Res., Vol. 61, pp. 4003-4009.

Hur E, Kim H-H, Choi S M, Kim J H, Yim S, Kwon H J, Choi Y, Kim D K, Lee M-0, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", Mol. Pharmacol., Vol 62(5), pp. 975-982.

Jameel A, Skilton R A, Campbell T A, Chander S K, Coombes R C and Luqmani Y A. 1992 "Clinical Jolly C and Morimoto R I. 2000 "Role of the heat shock response and molecular chaperones in oncogenesis and cell death", J. Nat. Cancer Inst., Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", Cancer, Vol. 85, pp. 1649-1657.

Kelland L R, Abel G, McKeage M J, Jones M, Goddard P M, Valenti M, Murrer B A, and Harrap K R. 1993 "Preclinical antitumour evaluation of bisacetalo-amino-dichloro-cyclohexylamine platinum (IV): an orally active platinum drug", Cancer Research, Vol. 53, pp. 2581-2586.

Kelland L R, Sharp S Y, Rogers P M, Myers T G and Workman P. 1999 "DT-diaphorase expression and tumour cell sensitivity to 17-allylamino, 17-demethoxygeldanamycin, an inhibitor of heat shock protein 90", J. Natl. Cancer Inst., Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", Jap. J. Cancer Res., Vol. 92(12), 1342-1351.

Kwon H J, Yoshida M, Abe K, Horinouchi S and Bepple T. 1992 "Radicicol, an agent inducing the reversal of transformed phentoype of src-transformed fibroblasts, Biosci., Biotechnol., Biochem., Vol. 56, pp. 538-539.

Lebeau J, Le Cholony C, Prosperi M T and Goubin G. 1991 "Constitutive overexpression of 89 kDa heat shock protein gene in the HBL100 mammary cell line converted to a tumourigenic phenotype by the EJE24 Harveyras oncogene", Oncogene, Vol. 6, pp. 1125-1132.

Marcu M G, Chadli A, Bouhouche I, Catelli M and Neckers L. 2000a "The heat shock protein 90 antagonist novobiocin interacts with a previously unrecognised ATP-binding domain in the carboxyl terminus of the chaperone", J. Biol. Chem., Vol. 275, pp. 37181-37186.

Marcu M G, Schulte T W and Neckers L. 2000b "Novobiocin and related coumarins and depletion of heat shock protein 90-dependent signaling proteins", J. Natl. Cancer Inst., Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", Cancer Res., Vol. 60, pp. 2232-2238.

Neckers L, Schulte T W and Momnaaugh E. 1999 "Geldanamycin as a potential anti-cancer agent: its molecular target and biochemical activity", Invest. New Drugs, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", Proc. Am. Assoc. Cancer Res., Vol. 38, pp. 308.

Panaretou B, Prodromou C, Roe S M, OBrien R, Ladbury J E, Piper P W and Pearl L H. 1998 "ATP binding and hydrolysis are essential to the function of the HSP90 molecular chaperone in vivo", EMBO J., Vol. 17, pp. 4829-4836.

Pratt W B. 1997 "The role of the HSP90-based chaperone system in signal transduction by nuclear receptors and receptors signalling via MAP kinase", Annu. Rev. Pharmacol. Toxicol., Vol. 37, pp. 297-326.

Prodromou C, Roe S M, O'Brien R, Ladbury J E, Piper P W and Pearl L H. 1997 "Identification and structural characterisation of the ATP/ADP-binding site in the HSP90 molecular chaperone", Cell, Vol. 90, pp. 65-75.

Prodromou C, Panaretou B, Chohan S, Siligardi G, O'Brien R, Ladbury J E, Roe S M, Piper P W and Pearl L H. 2000 "The ATPase cycle of HSP90 drives a molecular "clamp" via transient dimerisation of the N-terminal domains", EMBO J., Vol. 19, pp. 4383-4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", J. Med. Chem., Vol. 42, pp. 260-266.

Rutherford S L and Lindquist S. 1998 "HSP90 as a capacitor for morphological evolution. Nature, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", Mol. Endocrinoloqy, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", Cell Stress and Chaperones, Vol. 3, pp. 100-108.

Schulte T W and Neckers L M. 1998 "The benzoquinone ansamycin 17-allylamino-17-demethoxygeldanamcyin binds to HSP90 and shares important biologic activities with geldanamycin", Cancer Chemother. Pharmacol., Vol. 42, pp. 273-279.

Smith D F. 2001 "Chaperones in signal transduction", in: Molecular chaperones in the cell (P Lund, ed.; Oxford University Press, Oxford and NY), pp. 165-178.

Smith D F, Whitesell L and Katsanis E. 1998 "Molecular chaperones: Biology and prospects for pharmacological intervention", Pharmacological Reviews, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", J. Biol. Chem., Vol. 270, pp. 3574-3581.

Stebbins C E, Russo A, Schneider C, Rosen N, Hartl F U and Pavietich N P. 1997 "Crystal structure of an HSP90-geldanamcyin complex: targeting of a protein chaperone by an antitumour agent", Cell, Vol. 89, pp. 239-250.

Supko J G, Hickman R L, Grever M R and Malspeis L. 1995 "Preclinical pharmacologic evaluation of geldanamycin as an antitumour agent", Cancer Chemother. Pharmacol., Vol. 36, pp. 305-315.

Tytell M and Hooper P L. 2001 "Heat shock proteins: new keys to the development of cytoprotective therapies", Emerging Therapeutic Targets, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", Mol. Cell. Biol., Vol. 6, pp. 21 98-2206.

Waxman, Lloyd H. Inhibiting hepatitis C virus processing and replication. (Merck & Co., Inc., USA). PCT Int. Appl. (2002), WO 0207761

Whitesell L, Mimnaugh E G, De Costa B, Myers C E and Neckers L M. 1994 "Inhibition of heat shock protein HSP90-pp 60v-src heteroprotein complex formation by benzoquinone ansamycins: essential role for stress proteins in oncogenic transformation", Proc. Natl. Acad. Sci. USA., Vol. 91, pp. 8324-8328.

Yorgin et al. 2000 "Effects of geldanamycin, a heat-shock protein 90-binding agent, on T cell function and T cell nonreceptor protein tyrosine kinases", J. Immunol., Vol 164(6), pp. 2915-2923.

Young J C, Moarefi I and Hartl F U. 2001 "HSP90: a specialised but essential protein-folding tool", J. Cell. Biol., Vol. 154, pp. 267-273.

Zhao J F, Nakano H and Sharma S. 1995 "Suppression of RAS and MOS transformation by radicicoi", Oncoqene, Vol. 11, pp. 161-173.

SUMMARY OF THE INVENTION

The invention relates to compounds of the formula I

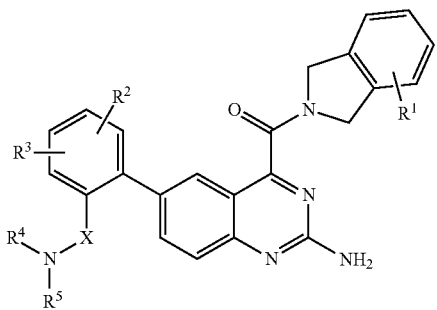

in which $R^1$ denotes H, $(CH_2)_n$Het, $(CH_2)_n$Ar, Hal or A, $R^2$, $R^3$ each, independently of one another, denote H, $(CH_2)_n$Het, $(CH_2)_n$Ar, Hal, OH or OA, $R^4$, $R^5$ each, independently of one another, denote H, A, $(CH_2)_n$Het, $(CH_2)_n$Ar or $(CH_2)_p OC(=O)(CH_2)_p NH_2$, $R^4$ and $R^5$, together with the N atom to which they are bonded, also denote a saturated, unsaturated or aromatic mono- or bicyclic heterocycle which is unsubstituted or mono-, di- or trisubstituted by Hal, A, $(CH_2)_n$OH, $(CH_2)_n$OA, $(CH_2)_n$NH$_2$, $(CH_2)_n$COOH, $(CH_2)_n$COOA, NHCOA, NA'COA, CONH$_2$, CONHA, CONAA', OC(=O)(CH$_2)_p$NH$_2$ and/or =O (carbonyl oxygen) and which may contain a further 1 to 3 N, O and/or S atoms, and in which, in addition, one N atom may be oxidised, X denotes CO or SO$_2$, Ar denotes phenyl, naphthyl, tetrahydronaphthyl or biphenyl, each of which is unsubstituted or mono-, di-, tri-, tetra- or pentasubstituted by A, Hal, $(CH_2)_n$OA, $(CH_2)_n$OH, $(CH_2)$CN, SA, SOA, SO$_2$A, NO$_2$, C≡CH, $(CH_2)_n$COOH, CHO, $(CH_2)_n$COOA, CONH$_2$, CONHA, CONAA', NHCOA, CH(OH)A, $(CH_2)_n$NH$_2$, $(CH_2)_n$NHA, $(CH_2)_n$NAA', $(CH_2)_n$NHSO$_2$A, SO$_2$NH$(CH_2)_n$NH$_2$, SO$_2$NH$_2$, SO$_2$NHA, SO$_2$NAA', CONH(CH$_2)_n$COOA, CONH(CH$_2)_n$COOH, NHCO(CH$_2)_n$COOA, NHCO(CH$_2)_n$COOH, CONH(CH$_2)_n$NH$_2$, CONH(CH$_2)_n$NHA, CONH(CH$_2)_n$NAA', CONH(CH$_2)_n$CN and/or $(CH_2)_n$CH(NH$_2$)COOH, Het denotes a mono- or bicyclic saturated, unsaturated or aromatic heterocycle having 1 to 4 N, O and/or S atoms, which may be unsubstituted or mono-, di- or trisubstituted by A, OA, OH, phenyl, SH, S(O)$_m$A, Hal, NO$_2$, CN, COA, COOA, COObenzyl, CONH$_2$, CONHA, CONAA', SO$_2$NH$_2$, NH$_2$, NHA, NAA', NHSO$_2$A and/or =O (carbonyl oxygen), A, A' each, independently of one another, denote unbranched or branched alkyl having 1-10 C atoms, in which 1-3 non-adjacent CH$_2$ groups may be replaced by O, S, SO, SO$_2$, NH, NMe or NEt and/or, in addition, 1-5 H atoms may be replaced by F and/or Cl, or cyclic alkyl having 3-8 C atoms, n denotes 0, 1, 2, 3 or 4, p denotes 1, 2, 3 or 4, and pharmaceutically usable salts and stereoisomers thereof, including mixtures thereof in all ratios.

The invention relates to the compounds of the formula I and salts thereof and to a process for the preparation of compounds of the formula I and pharmaceutically usable salts, tautomers and stereoisomers thereof, characterised in that a) a compound of the formula II

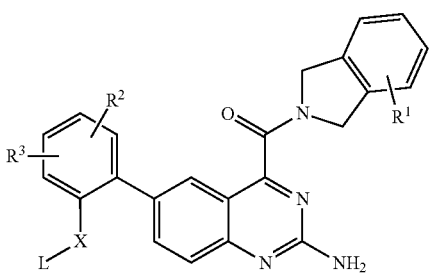

in which $R^1$, $R^2$, $R^3$ and X have the meanings indicated in Claim 1, and L denotes F, Cl, Br, I or a free or reactively modified OH group, is reacted with a compound of the formula II

NHR$^4$R$^5$   III in which $R^4$ and $R^5$ have the meanings indicated in Claim 1, or b) a compound of the formula IV

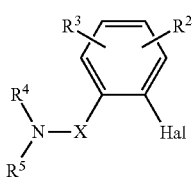

in which X, $R^2$, $R^3$, $R^4$ and $R^5$ have the meanings indicated in Claim 1,
and Hal denotes bromine or iodine,
is reacted with a compound of the formula V

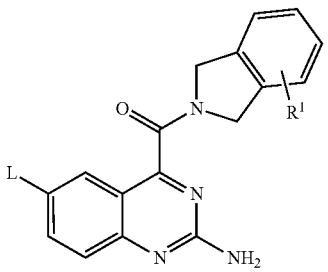

in which $R^1$ has the meaning indicated in Claim 1,
and L denotes a boronic acid or boronic acid ester radical, or c) a compound of the formula VI

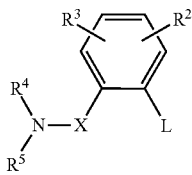

in which X, $R^2$, $R^3$, $R^4$ and $R^5$ have the meanings indicated in Claim 1
and L denotes a boronic acid or boronic acid ester radical,
is reacted with a compound of the formula VII

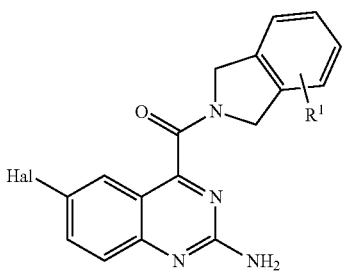

in which $R^1$ has the meaning indicated in Claim 1,
and Hal denotes bromine or iodine,
and/or a base or acid of the formula I is converted into one of its salts.

Compounds of the formula I are also taken to mean the hydrates and solvates of these compounds, furthermore pharmaceutically usable derivatives. The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, the salts of the compounds according to the invention and also so-called prodrug compounds.

Prodrug derivatives are taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The expression "effective amount" means the amount of a medicament or pharmaceutical active ingredient that causes a biological or medical response which is sought or desired, for example, by a researcher or physician in a tissue, system, animal or human.

In addition, the expression "therapeutically effective amount" means an amount which, compared with a corresponding subject who has not received this amount, has the following consequence:

improved healing treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric @

For all radicals which occur more than once, their meanings are independent of one another.

Above and below, the radicals and parameters $R^1$, $R^2$, $R^3$, $R^4$, $R^5$ and X have the meanings indicated for the formula I, unless expressly indicated otherwise.

Carbamoyl denotes aminocarbonyl.

BOC or Boc denotes tert-butyloxycarbonyl.

A or A' preferably denotes alkyl, is unbranched (linear) or branched, and has 1, 2, 3, 4, 5, 6, 7, 8, 9 or 10 C atoms. A or A' particularly preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

A or A' very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoro-ethyl.

A, A' also each denote, independently of one another, unbranched or branched alkyl having 1-10 C atoms, in which 1-3 non-adjacent $CH_2$ groups may be replaced by O, S, SO, $SO_2$, NH, NMe, or NEt, such as, for example, 2-methoxyethyl or 3-methylaminopropyl.

A or A' also denotes cyclic alkyl(cycloalkyl). Cycloalkyl preferably denotes cyclopropyl, cyclobutyl, cyclopentyl, cyclohexyl or cycloheptyl. Cyclic alkyl furthermore preferably denotes cyclopropylmethyl, cyclopentylmethyl or cyclohexylmethyl.

Cycloalkylalkylene denotes, for example, cyclopropylmethylene or cyclohexylmethylene.

A,A' particularly preferably denote, in each case independently of one another, unbranched or branched alkyl having 1-6 C atoms, in which 1-2 non-adjacent $CH_2$ groups may be replaced by O, NH, NMe or NEt and/or, in addition, 1-5 H atoms may be replaced by F and/or Cl, cyclic alkyl having 3-8 C atoms $R^1$ preferably denotes H, Hal or A, very particularly preferably H.

$R^2, R^3$ preferably denote, in each case independently of one another, H, Hal, OH or OA, very particularly preferably H, F, Cl, methoxy, ethoxy, propoxy or isopropoxy.

$R^4, R^5$ preferably denote, in each case independently of one another, H, methyl, ethyl, propyl, isopropyl, butyl, isobutyl, sec-butyl, tert-butyl, pentyl, hexyl, trifluoromethyl, cyclopropyl, cyclobutyl, cyclopentyl, cyclohexyl, cycloheptyl, 2-hydroxyethyl, 2-dimethylaminoethyl, 2-methylaminoethyl, 2-aminoethyl, 2-dimethylamino-1-methylethyl, 3-methyl-3H-imidazol-4-ylmethyl or azetidinyl.

$R^4$ and $R^5$ preferably also denote, together with the N atom to which they are bonded, 1,3-dihydroisoindolyl, pyrrolidinyl, azetidinyl, azepanyl, piperazinyl, piperidinyl, morpholinyl, pyridyl, pyrrolyl, imidazolyl, benzimidazolyl, triazolyl or pyrimidinyl, each of which is unsubstituted or mono-, di- or tri-substituted by Hal, A, $(CH_2)_n$OH, $(CH_2)_n$OA, $(CH_2)_n$NH$_2$, $(CH_2)_n$COOH, $(CH_2)_n$COOA, NHCOA, NA'COA, CONH$_2$, CONHA, CONAA', OC(=O)$(CH_2)_p$NH$_2$ and/or =O (carbonyl oxygen), and in which, in addition, one N atom may be oxidised.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes phenyl which is unsubstituted or mono-, di-, tri-, tetra- or pentasubstituted by A, Hal and/or OA.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes pyridyl, pyrimidinyl, furyl, thienyl, pyrrolyl, imidazolyl, pyrazolyl, triazolyl, oxazolyl, isoxazolyl, thiazolyl, benzothiazolyl, benzo-1,4-dioxanyl, quinolyl, isoquinolyl, quinazolinyl, benzimidazolyl, indazolyl, indolyl, 1,3-dihydroisoindolyl, benzofuranyl, dihydrobenzofuranyl, benzo-1,3-dioxolyl, piperazinyl, pyrazinyl, pyridazinyl, morpholinyl, azepanyl, azetidinyl, pyrrolidinyl or piperidinyl, each of which is unsubstituted or mono-, di- or trisubstituted by A, OA, OH, Hal, CN and/or =O (carbonyl oxygen).

n preferably denotes 0, 1 or 2.

p preferably denotes 1 or 2.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia Het denotes pyridyl, pyrimidinyl, furyl, thienyl, pyrrolyl, imidazolyl, pyrazolyl, triazolyl, oxazolyl, isoxazolyl, thiazolyl, benzothiazolyl, benzo-1,4-dioxanyl, quinolyl, isoquinolyl, quinazolinyl, benzimidazolyl, indazolyl, indolyl, 1,3-dihydroisoindolyl, benzofuranyl, dihydrobenzofuranyl, benzo-1,3-dioxolyl, piperazinyl, pyrazinyl, pyridazinyl, morpholinyl, azepanyl, azetidinyl, pyrrolidinyl or piperidinyl, each of which is unsubstituted or mono-, di- or tri-substituted by A, OA, OH, Hal, CN and/or =O (carbonyl oxygen);

in Ib Ar denotes phenyl which is unsubstituted or mono-, di-, tri-, tetra- or pentasubstituted by A, Hal and/or OA;

in Ic A, A' each, independently of one another, denote unbranched or branched alkyl having 1-6 C atoms, in which 1-2 non-adjacent $CH_2$ groups may be replaced by O, NH, NMe or NEt and/or, in addition, 1-5 H atoms may be replaced by F and/or Cl, cyclic alkyl having 3-8 C atoms;

in Id Het denotes pyridyl, pyrimidinyl, furyl, thienyl, pyrrolyl, imidazolyl, pyrazolyl, triazolyl, oxazolyl, isoxazolyl, thiazolyl, piperazinyl, pyrazinyl, pyridazinyl, morpholinyl, azepanyl, azetidinyl, pyrrolidinyl or piperidinyl, each of which is un-substituted or mono-, di- or trisubstituted by A, OA, OH, Hal, CN and/or =O (carbonyl oxygen);

in Ie $R^4$ and $R^5$, together with the N atom to which they are bonded, also denote 1,3-dihydroisoindolyl, pyrrolidinyl, azetidinyl, azepanyl, piperazinyl, piperidinyl, morpholinyl, pyridyl, pyrrolyl, imidazolyl, benzimidazolyl, triazolyl or pyrimidinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA', $OC(=O)(CH_2)NH_2$ and/or =O (carbonyl oxygen), and in which, in addition, one N atom may be oxidised;

in If $R^1$ denote H, Hal or A;

in Ig $R^1$ denotes H;

in Ih $R^2$, $R^3$ each, independently of one another, denote H, Hal, OH or OA;

in Ii $R^2$, $R^3$ each, independently of one another, denote H, F, Cl, methoxy, ethoxy, propoxy or isopropoxy;

in Ij $R^1$ denotes H, Hal or A, $R^2$, $R^3$ each, independently of one another, denote H, Hal, OH or OA, $R^4$, $R^5$ each, independently of one another, denote H, A, $(CH_2)_n$Het, $(CH_2)_n$Ar or $(CH_2)_pOC(=O)(CH_2)_pNH_2$, $R^4$ and $R^5$, together with the N atom to which they are bonded, also denote 1,3-dihydroisoindolyl, pyrrolidinyl, azetidinyl, azepanyl, piperazinyl, piperidinyl, morpholinyl, pyridyl, pyrrolyl, imidazolyl, benzimidazolyl, triazolyl or pyrimidinyl, each of which is unsubstituted or mono-, di- or tri-substituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA', $OC(=O)(CH_2)_pNH_2$ and/or =O (carbonyl oxygen), and in which, in addition, one N atom may be oxidised, X denotes CO or $SO_2$, Ar denotes phenyl which is unsubstituted or mono-, di-, tri-, tetra- or pentasubstituted by A, Hal and/or OA, Het denotes pyridyl, pyrimidinyl, furyl, thienyl, pyrrolyl, imidazolyl, pyrazolyl, triazolyl, oxazolyl, isoxazolyl, thiazolyl, piperazinyl, pyrazinyl, pyridazinyl, morpholinyl, azepanyl, azetidinyl, pyrrolidinyl or piperidinyl, each of which is un-substituted or mono-, di- or trisubstituted by A, OA, OH, Hal, CN and/or =O (carbonyl oxygen), A, A' each, independently of one another, denote unbranched or branched alkyl having 1-6 C atoms, in which 1-2 non-adjacent $CH_2$ groups may be replaced by O, NH, NMe or NEt and/or, in addition, 1-5 H atoms may be replaced by F and/or Cl, or cyclic alkyl having 3-8 C atoms, n denotes 0, 1, 2, 3 or 4, p denotes 1, 2, 3 or 4;

and pharmaceutically usable salts, tautomers and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

Compounds of the formula I can preferably be obtained by reacting a compound of the formula II with a compound of the formula III.

In the compounds of the formula II, L preferably denotes F, Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy). In the compounds of the formula II, L preferably denotes Cl.

The reaction is generally carried out in an inert solvent, in the presence of an acid-binding agent, preferably an alkali or alkaline-earth metal hydroxyide, carbonate or bicarbonate, or of another salt of a weak acid of the alkali or alkaline-earth metals, preferably potassium, sodium, calcium or caesium.

The addition of an organic base, such as 4-methylmorpholine, triethylamine, dimethylaniline, pyridine or quinoline, may also be favourable.

If a compound of the formula II in which L denotes OH is reacted with an amine, a coupling reagent is preferably added before and/or during the reaction, for example ethyl 2-ethoxy-1,2-dihydroquinoline-1-carboxylate, propane-phosphonic cycloanhydride or O-(benzotriazol-1-yl)-N,N,N',N',-tetramethyluronium tetrafluoroborate (TBTU).

The reaction is carried out by methods which are known to the person skilled in the art.

Reaction is initially carried out in a suitable solvent.

Examples of suitable solvents are hydrocarbons, such as hexane, petroleum ether, benzene, toluene or xylene; chlorinated hydrocarbons, such as trichloroethylene, 1,2-dichloro-ethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The solvent is particularly preferably acetonitrile or DMF.

Depending on the conditions used, the reaction time is between a few minutes and 14 days, the reaction temperature is between about 0° and 150°, normally between 15° and 120°, particularly preferably between 50° and 100° C.

Compounds of the formula I can furthermore preferably be obtained by reacting a compound of the formula IV with a compound of the formula V. The reaction is carried out under conditions as are known to the person skilled in the art for a Suzuki reaction.

The starting compounds of the formulae IV and V are generally known. If they are novel, however, they can be prepared by methods known per se. In the compounds of the formula V, L preferably denotes

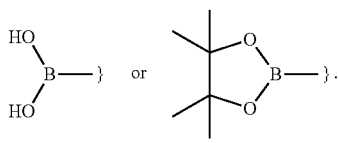

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane and/or water.

Compounds of the formula I can furthermore preferably be obtained by reacting a compound of the formula VI with a compound of the formula VII. The reaction is carried out under conditions as are known to the person skilled in the art for a Suzuki reaction.

The starting compounds of the formulae VI and VII are generally known. If they are novel, however, they can be prepared by methods known per se. In the compounds of the formula VI, L preferably denotes

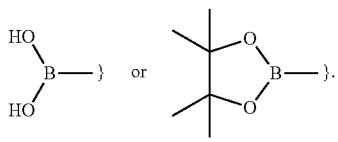

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane and/or water.

It is furthermore possible to convert a compound of the formula I into another compound of the formula I by, for example, reducing nitro groups to amino groups, for example by hydrogenation on Raney nickel or Pd/carbon in an inert solvent, such as methanol or ethanol, and/or converting an ester group into a carboxyl group and/or converting an aldehyde group into an alkylated amine by reductive amination and/or esterifying carboxyl groups by reaction with alcohols and/or converting acid chlorides into an acid amide by reaction with an amine.

Furthermore, free amino and/or hydroxyl groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

Ether cleavages are carried out by methods which are known to the person skilled in the art.

The reaction is carried out in a suitable solvent, as indicated above, preferably by addition of boron tribromide.

The reaction is particularly preferably carried out in dichloromethane at a reaction temperature between about −30° and 50°, normally between −20° and 20°, in particular between about −15° and about 0°.

The invention also relates to the compounds of the formula II

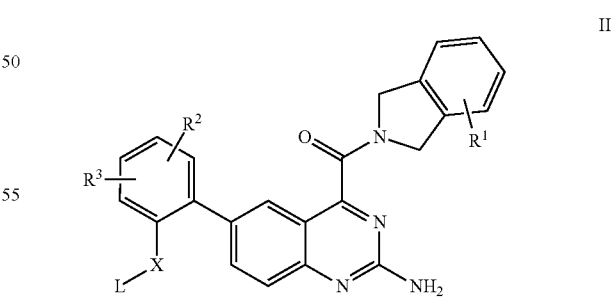

in which $R^1$ denotes H, Hal or A, $R^2$, $R^3$ each, independently of one another, denote H, Hal, OH or OA, X denotes CO or $SO_2$, A denotes unbranched or branched alkyl having 1-6 C atoms, in which 1-2 non-adjacent $CH_2$ groups may be replaced by O, NH, NMe or Net and/or, in addition, 1-5 H atoms may be replaced by F and/or Cl, or cyclic alkyl having 3-8 C atoms, L denotes F, Cl, Br, I or a free or reactively modified OH group, and salts thereof.

The meanings and the preferred meanings of the radicals indicated are those as indicated above for the compounds of the formula I.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner.

The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/l acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.1 mg to 3 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition requiring treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

Further medicament active ingredients are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

The invention also relates to a set (kit) consisting of separate packs of
(a) an effective amount of a compound according to the invention and/or pharmaceutically usable derivatives, solvates and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of diseases in which HSP90 plays a role.

The invention thus relates to the use of the compounds according to the invention, and pharmaceutically usable derivatives, solvates and stereoisomers thereof, including mixtures thereof in all ratios, for the preparation of a medicament for the treatment of diseases in which the inhibition, regulation and/or modulation of HSP90 plays a role.

The present invention encompasses the use of the compounds according to the invention and/or physiologically acceptable salts and solvates thereof for the preparation of a medicament for the treatment of tumour diseases, such as, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease; viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type I (HIV-I) and human immunodeficiency virus type II (HIV-II);

for immune suppression in transplants; inflammation-induced diseases, such as rheumatoid arthritis, asthma, sepsis, multiple sclerosis, type 1 diabetes, lupus erythematosus, psoriasis and inflammatory bowel disease; cystic fibrosis; diseases associated with angiogenesis, such as, for example, diabetic retinopathy, haemangiomas, endometriosis, tumour angiogenesis; infectious diseases; autoimmune diseases; ischaemia; promotion of nerve regeneration; fibrogenetic diseases, such as, for example, scleroderma, polymyositis, systemic lupus, cirrhosis of the liver, keloid formation, interstitial nephritis and pulmonary fibrosis;

The compounds according to the invention can inhibit, in particular, the growth of cancer, tumour cells and tumour metastases and are therefore suitable for tumour therapy.

The present invention furthermore encompasses the use of the compounds according to the invention and/or physiologically acceptable salts and solvates thereof for the preparation of a medicament for the protection of normal cells against toxicity caused by chemotherapy, and for the treatment of diseases in which incorrect protein folding or aggregation is a principal causal factor, such as, for example, scrapie, Creutzfeldt-Jakob disease, Huntington's or Alzheimer's.

The invention also relates to the use of the compounds according to the invention and/or physiologically acceptable salts and solvates thereof for the preparation of a medicament for the treatment of diseases of the central nervous system, of cardiovascular diseases and cachexia.

In a further embodiment, the invention also relates to the use of the compounds according to the invention and/or physiologically acceptable salts and solvates thereof for the preparation of a medicament for HSP90 modulation, where the modulated biological HSP90 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemiaireperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

In a further embodiment, the invention also relates to the use of the compounds according to the invention and/or physiologically acceptable salts and solvates thereof for the preparation of a medicament for the treatment of ischaemia as a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Test Method for the Measurement of HSP90 Inhibitors

The binding of geldanamycin or 17-allylamino-17-demethoxygeldanamycin (17AAG) to HSP90 and competitive inhibition thereof can be utilised in order to determine the inhibitory activity of the compounds according to the invention (Carreras et al. 2003, Chiosis et al. 2002).

In the specific case, a radioligand filter binding test is used. The radioligand used here is tritium-labelled 17-allylaminogeldanamycin, [3H]17AAG. This filter binding test allows a targeted search for inhibitors which interfere with the ATP binding site.

Material

Recombinant human HSP90a (*E. coli* expressed, 95% purity);

[3H]17AAG (17-allylaminogeldanamycin, [allylamino-2,3-$^3$H. Specific activity: $1.11 \times 10^{12}$ Bq/mmol (Moravek, MT-1717);

HEPES filter buffer (50 mM HEPES, pH 7.0, 5 mM MgCl2, BSA 0.01%)

Multiscreen FB (1 µm) filter plate (Millipore, MAFBNOB 50).

Method

The 96-well microtitre filter plates are firstly irrigated and coated with 0.1% of polyethylenimine.

The test is carried out under the following conditions:
Reaction temperature 22° C.
Reaction time: 30 min., shaking at 800 rpm
Test volume: 50 µl Final concentrations:
50 mM HEPES HCl, pH 7.0, 5 mM MgCl2, 0.01% (w/v) of BSA
HSP90: 1.5 µg/assay
[3H]17AAG: 0.08 µM.

At the end of the reaction, the supernatant in the filter plate is removed by suction with the aid of a vacuum manifold (Multiscreen Separation System, Millipore), and the filter is washed twice.

The filter plates are then measured in a beta counter (Microbeta, Wallac) with scintillator (Microscint 20, Packard).

"% of control" is determined from the "counts per minutes" values, and the IC-50 value of a compound is calculated therefrom.

TABLE I

HSP90 inhibition by compounds of the formula I according to the invention

| Compound No. | IC$_{50}$ |
|---|---|
| "A1" | A |
| "A2" | A |
| "A3" | A |
| "A4" | A |
| "A5" | A |
| "A6" | A |
| "A7" | A |
| "A8" | A |
| "A9" | A |
| "A10" | A |
| "A11" | A |
| "A12" | A |
| "A13" | A |
| "A14" | A |
| "A15" | A |
| "A16" | A |
| "A17" | A |
| "A18" | A |
| "A19" | A |
| "A20" | A |
| "A21" | A |
| "A22" | A |
| "A23" | A |
| "A24" | A |
| "A25" | A |
| "A26" | A |
| "A27" | B |
| "A28" | A |
| "A29" | A |
| "A30" | A |
| "A31" | A |
| "A32" | A |
| "A33" | A |
| "A34" | A |
| "A35" | A |
| "A36" | A |
| "A37" | A |
| "A38" | A |
| "A39" | A |
| "A40" | A |
| "A41" | A |
| "A42" | A |
| "A43" | A |
| "A44" | A |
| "A45" | A |
| "A46" | A |
| "A47" | A |
| "A48" | A |
| "A49" | A |
| "A50" | B |
| "A51" | A |
| "A52" | A |
| "A53" | A |
| "A54" | A |
| "A55" | A |
| "A56" | A |

TABLE I-continued

HSP90 inhibition by compounds of the formula I according to the invention

| Compound No. | IC$_{50}$ |
| --- | --- |
| "A57" | A |
| "A58" | A |
| "A59" | A |
| "A60" | A |
| "A61" | A |
| "A62" | A |
| "A63" | A |
| "A64" | A |
| "A65" | A |
| "A66" | A |
| "A67" | A |
| "A68" | A |
| "A69" | A |
| "A70" | A |
| "A71" | A |
| "A72" | A |
| "A73" | A |
| "A74" | A |
| "A75" | A |
| "A76" | A |
| "A77" | A |
| "A78" | A |
| "A79" | A |
| "A80" | A |
| "A81" | A |
| "A82" | A |
| "A83" | A |
| "A84" | C |
| "A85" | C |
| "A86" | A |
| "A87" | A |
| "A88" | B |
| "A89" | |
| "A90" | |

IC$_{50}$: 10 nM-1 μM=A
1 μM-10 μM=B
>10 μM=C

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

LC-MS Conditions

Hewlett Packard HP 1100 series system with the following features: ion source: electrospray (positive mode); scan: 100-1000 m/e; fragmentation voltage: 60 V; gas temperature: 300° C., DAD: 220 nm.

Method 1
A=water+0.05% of HCOOH/B=acetonitrile+0.04% of HCOOH
Flow=2.4 ml/min
WL=220 nm
Column: Chromolith Speed Rod RP18e 50-4.6
Gradient: 0 min 4% of B, 2.8 min 100% of B, 3.3 min 100% of B, 3.4 min 4% of B Method 2
A=water+0.01% of TFA/B=acetonitrile+0.01% of TFA
Flow: 1.5 ml/min
WL=220 nm
Column: Chromolith Performance RP18 100-3
Gradient: 0 min 1% of B, 3.5 min 100% of B, 5.0 min 100% of B, 5.5 min 10% of B, 6 min 1% of B Gradient polar:
5% of B→100% of B: 0 min to 3.0 min
100% of B: 3.0 min to 3.3 min
100% of B→20% of B: 3.3 min to 4 min
General Synthesis Schemes:

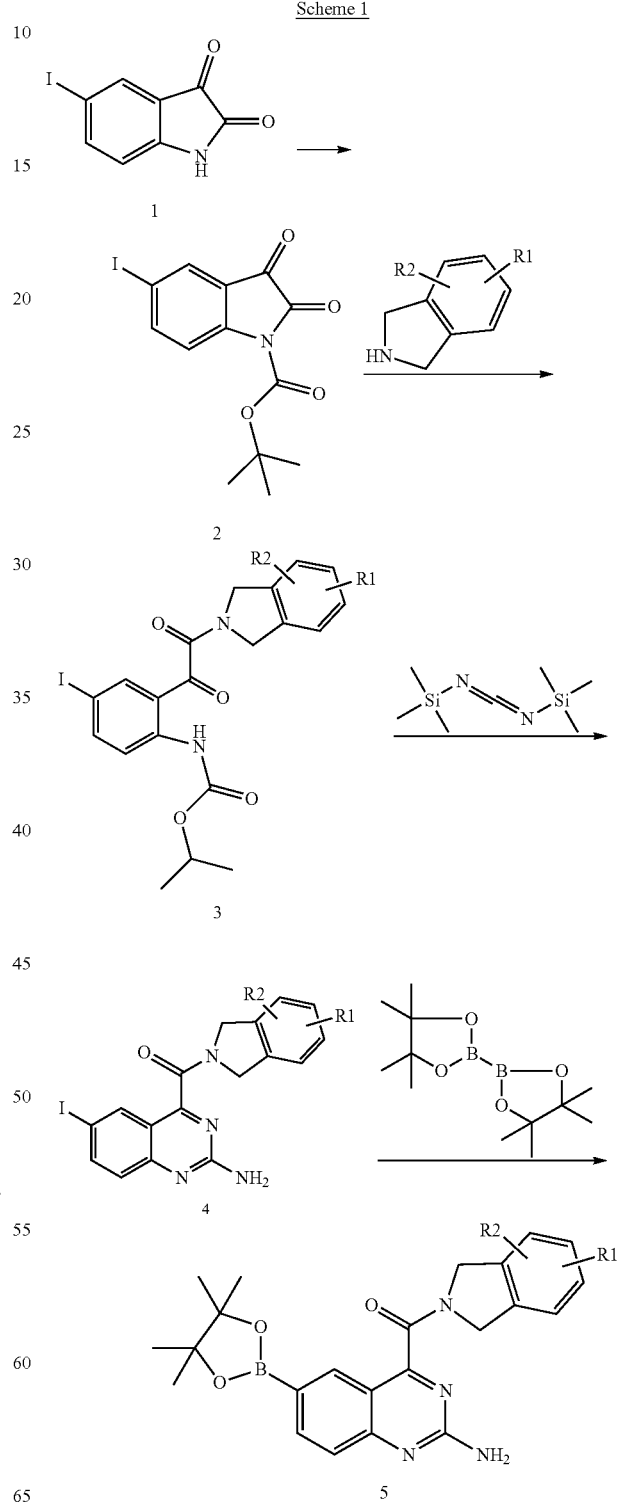

Scheme 1

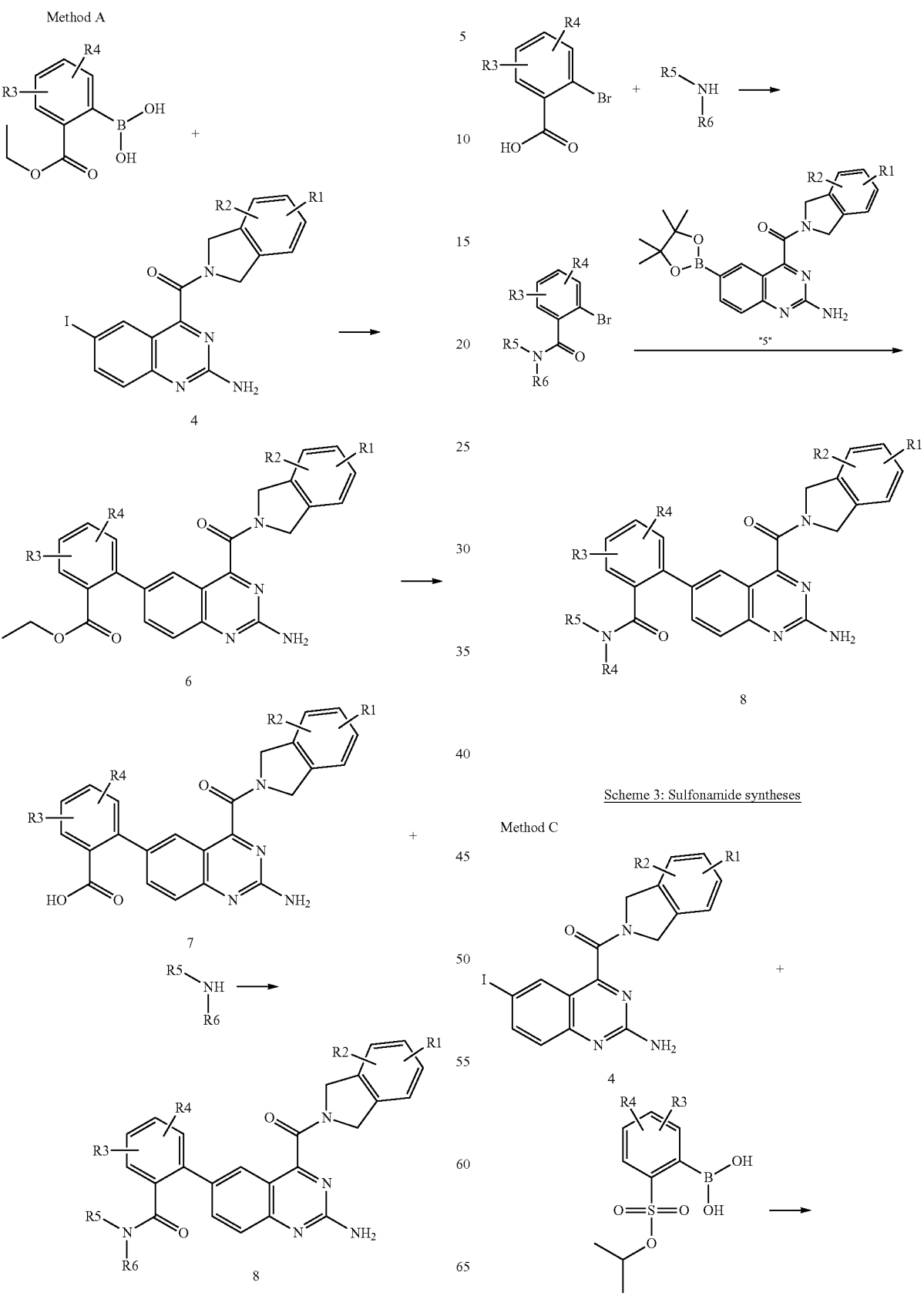

33

-continued

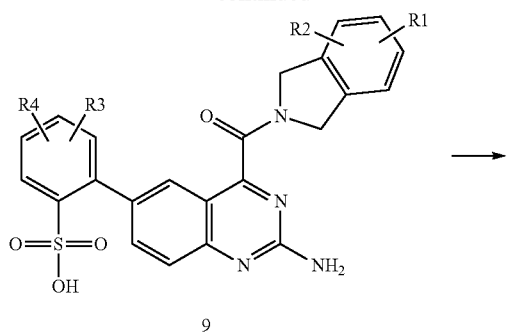

9

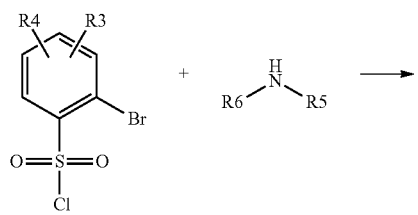

10

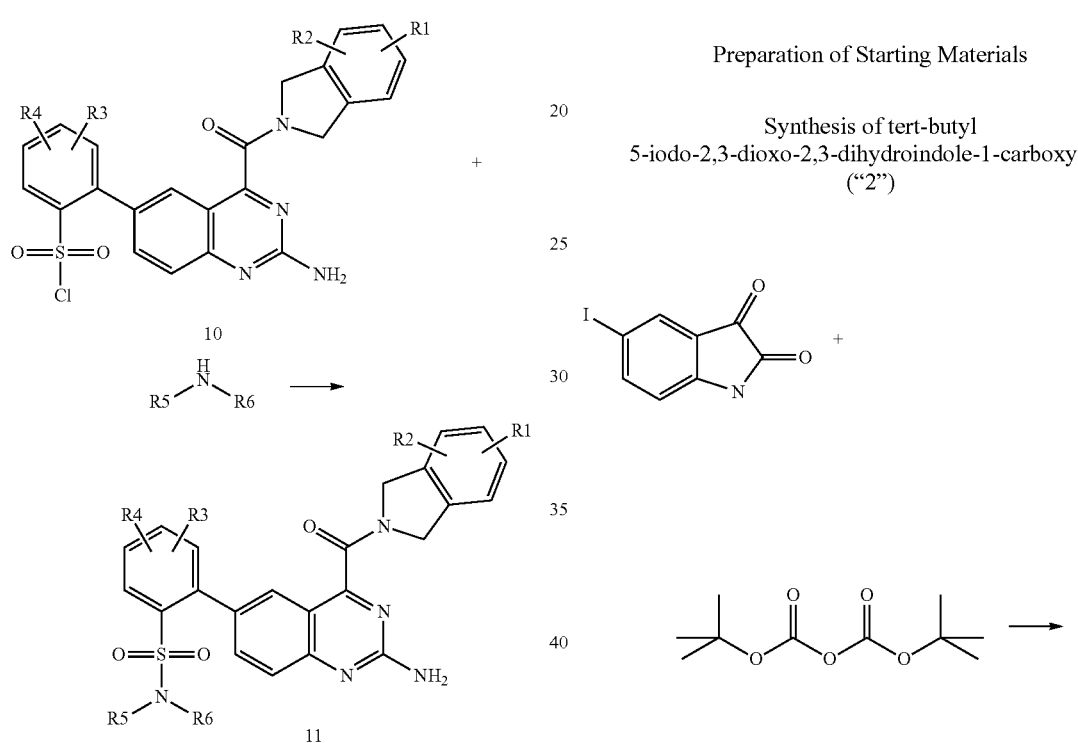

11

Method D

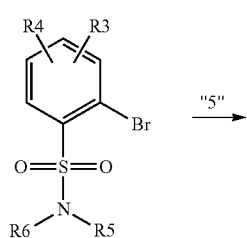

34

-continued

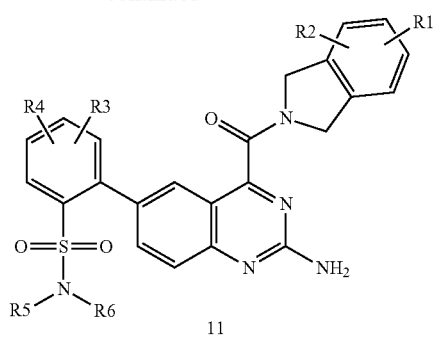

11

Preparation of Starting Materials

Synthesis of tert-butyl
5-iodo-2,3-dioxo-2,3-dihydroindole-1-carboxylate
("2")

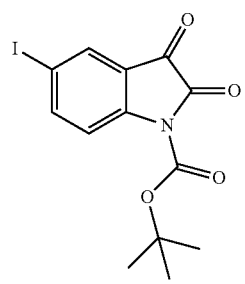

50 g of 5-iodo-1H-indole-2,3-dione are dissolved in 500 ml of THF, cooled to 10° C., and 43.97 g of di-tert-butyl dicarbonate are added. The mixture is stirred overnight at 23° C. and subsequently evaporated to dryness in vacuo. The residue is taken up in petroleum ether and THF and crystallised at −20° C. The yellow solid obtained in this way is filtered and dried at 30° C. in a drying cabinet. Yield: 62.41 g of tert-butyl 5-iodo-2,3-dioxo-2,3-dihydroindole-1-carboxylate; LC-MS retention time: 2.113 min.

Synthesis of tert-butyl {2-[2-(1,3-dihydroisoindol-2-yl)-2-oxoacetyl]-4-iodophenyl}carbamate ("3")

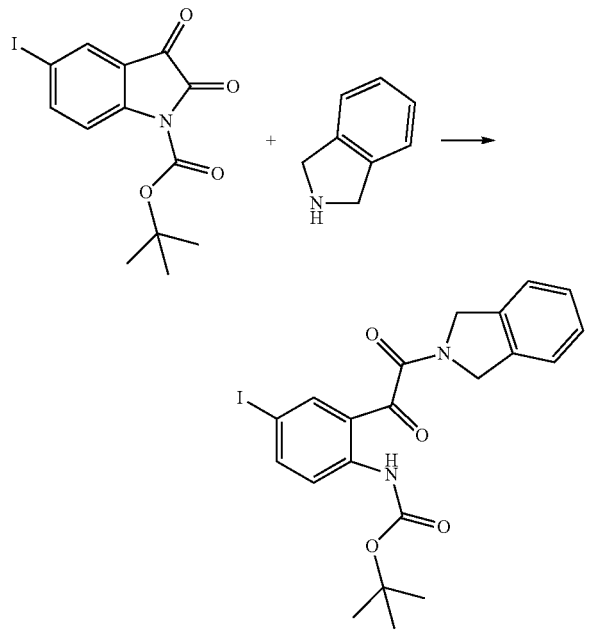

62.41 g of tert-butyl 5-iodo-2,3-dioxo-2,3-dihydroindole-1-carboxylate are dissolved in dried THF, and 18.98 ml of 2,3-dihydro-1H-isoindole are added. The mixture is stirred at 25° C. for 30 min, evaporated to dryness in vacuo, and the residue is triturated with petroleum ether, filtration gives 82.3 g of tert-butyl {2-[2-(1,3-dihydroisoindol-2-yl)-2-oxoacetyl]-4-iodophenyl}-carbamate (beige solid);

LC-MS retention time: 2.63 min;

$^1$H NMR (500 MHz, DMSO-d$_6$/TFA-d$_1$): ☐ [ppm] 8.014 (d, 1H), 7.962 (dd, 1H), 7.913 (d, 1H), 7.391 (d, 1H), 7.326-7.292 (m, 3H), 4.901 (s, 2H), 4.872 (s, 2H), 1.398 (s, 9H).

Synthesis of (2-amino-6-iodoquinazolin-4-yl)-(1,3-dihydroisoindol-2-yl)-methanone ("4")

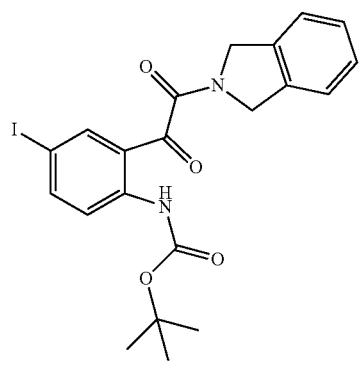

+

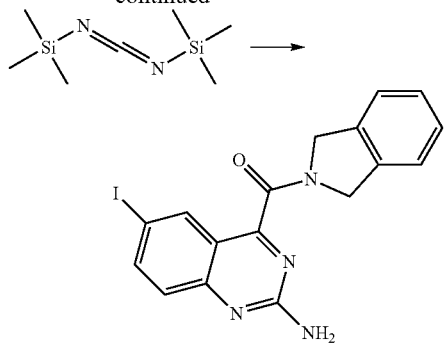

24.50 g of tert-butyl {2-[2-(1,3-dihydroisoindol-2-yl)-2-oxoacetyl]-4-iodophenyl}carbamate are dissolved in 500 ml of acetonitrile under argon. 0.756 g of caesium fluoride is added, and 16.887 ml of bis(trimethylsilyl)-carbodiimide are added dropwise to the solution over 5 min. The mixture is stirred at room temperature for 15 min, and 400 ml of dichloromethane are added. After addition of 400 ml of hydrochloric acid (1N), the product precipitates out as a white solid. Yield: 14 g of (2-amino-6-iodoquinazolin-4-yl)-(1,3-dihydroisoindol-2-yl)methanone; LC-MS retention time: 1.655 min;

$^1$H NMR (500 MHz, DMSO-d$_6$/TFA-d$_1$): δ [ppm] 8.143 (d, 1H), 7.957 (dd, 1H), 7.451 (d, 1H), 7.361-7.256 (m, 4H), 7.213 (s, 2H), 4.993 (s, 2H), 4.745 (s, 2H).

Synthesis of [2-amino-6-(4,4,5,5-tetramethyl-1,3,2-dioxaborolan-2-yl)-quinazolin-4-yl]-(1,3-dihydroisoindol-2-yl)methanone ("5")

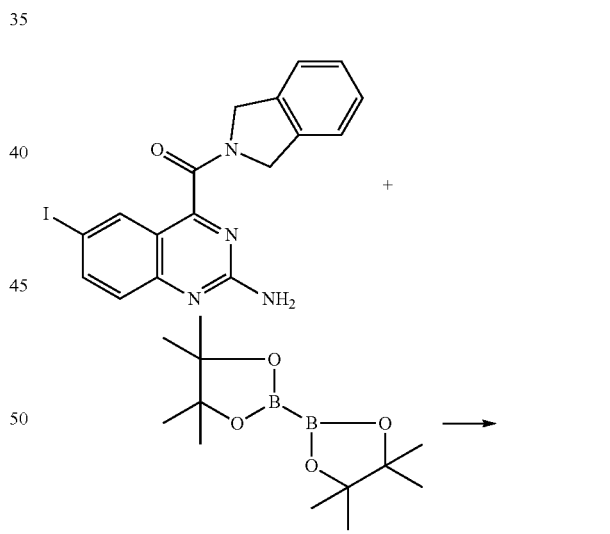

10 g of (2-amino-6-iodoquinazolin-4-yl)-(1,3-dihydroisoindol-2-yl)methanone ("4") are dissolved in 500 ml of dimethyl sulfoxide under an argon atmosphere. 6.1 g of bis(pinacolato)diboron, 8.017 g of potassium acetate and 981 mg of [1,1'-bis(diphenylphosphino)ferrocene]palladium(II) dichloride are added to this solution, and the mixture is then heated at 80° C. for 60 min. After cooling, 250 ml of diethyl ether are added to the mixture, which is then extracted four times against 100 ml of water each time. The combined organic phases are dried over sodium sulfate, filtered, and the filtrate is evaporated until a red oil is present. This oil is triturated with acetonitrile, giving pale-beige crystals. The precipitate is filtered and dried at 50° C. for 12 h in a drying cabinet. The resultant product is reacted further without further purification.

Yield: 6.45 g (65%) of [2-amino-6-(4,4,5,5-tetramethyl-1,3,2-dioxaborolan-2-yl)quinazolin-4-yl]-(1,3-dihydroisoindol-2-yl)methanone;

LC-MS retention time: 2.077 min (method 1).

Method A

Synthesis of ethyl 2-[2-amino-4-(1,3-dihydroisoindole-2-carbonyl)-quinazolin-6-yl]benzoate ("6")

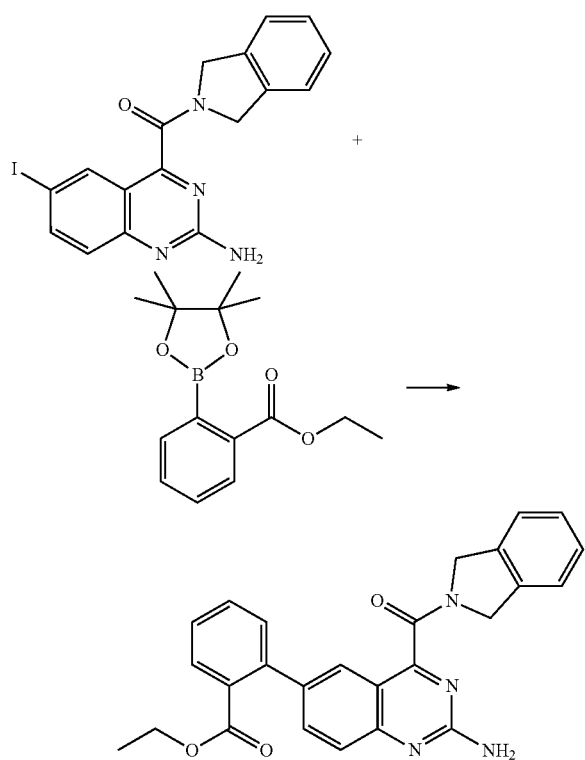

11.66 g of ethyl 2-(4,4,5,5-tetramethyl-1,3,2-dioxaborolan-2-yl)benzoate, 10.29 g of potassium carbonate, 0.67 ml of water and 912.4 mg of [1,1'-bis-(diphenylphosphino)ferrocene]palladium(II)dichloride are added to a solution of 15 g of 2-amino-6-iodo-4-(1,3-dihydroisoindol-2-ylcarbonyl)quinazoline in 200 ml of ethanol under argon. The mixture is heated at 120° C. for min, giving a clear solution. The hot solution is filtered through kieselguhr. On cooling, ethyl 2-[2-amino-4-(1,3-dihydroisoindole-2-carbonyl)-quinazolin-6-yl]benzoate crystallises out.

Yield: 15.4 g (94%) of ethyl 2-[2-amino-4-(1,3-dihydroisoindole-2-carbonyl)-quinazolin-6-yl]benzoate (LC-MS retention time: 2.056 min; "polar gradient" method).

The compound ethyl 2-[2-amino-4-(1,3-dihydroisoindole-2-carbonyl)quinazolin-6-yl]-4,5-difluorobenzoate is obtained analogously from [2-amino-6-(4,4,5,5-tetramethyl-1,3,2-dioxaborolan-2-yl)quinazolin-4-yl]-(1,3-dihydroisoindol-2-yl)methanone and ethyl 2-bromo-4,5-difluorobenzoate;

Yield: 67%; LC-MS retention time: 2.09 min (method 1).

Preparation of 2-[2-amino-4-(1,3-dihydroisoindole-2-carbonyl)quinazolin-6-yl]benzoic acid ("7")

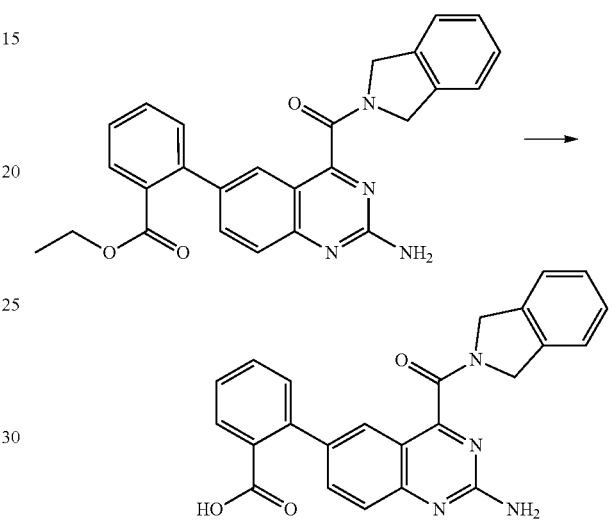

A solution of 15.3 g of ethyl 2-[2-amino-4-(1,3-dihydroisoindole-2-carbonyl)-quinazolin-6-yl]benzoate in 70 ml of sodium hydroxide solution (2 N) and 100 ml of THF is stirred at 80° C. for 6 h. The mixture is extracted three times with 100 ml of diethyl ether each time, and the aqueous phase is adjusted to pH7, whereupon 2-[2-amino-4-(1,3-dihydroisoindole-2-carbonyl)quinazolin-6-yl]benzoic acid precipitates out. The precipitate is filtered and dried at 50° C. in a drying cabinet.

Yield: 8.8 g (62%) of 2-[2-amino-4-(1,3-dihydroisoindole-2-carbonyl)quinazolin-6-yl]benzoic acid; LC-MS retention time: 1.707 min (method 1);

$^1$H NMR (500 MHz, DMSO-$d_6$/TFA-$d_1$): δ [ppm] 8.005-7.985 (m, 2H), 7.891 (d, 1H), 7.748 (d, 1H), 7.598 (t, 1H), 7.499 (t, 1H), 7.415-7.389 (m, 2H), 7.327-7.254 (m, 2H), 7.233 (d, 1H), 4.993 (s, 2H), 4.837 (s, 2H).

The compound 2-[2-amino-4-(1,3-dihydroisoindole-2-carbonyl)quinazolin-6-yl]-4,5-difluorobenzoate is obtained analogously from ethyl 2-[2-amino-4-(1,3-dihydroisoindole-2-carbonyl)quinazolin-6-yl]-4,5-difluorobenzoate;

Yield: 61%; LC-MS retention time: 2.09 min (method 1).

The compound 2-[2-amino-4-(1,3-dihydroisoindole-2-carbonyl)quinazolin-6-yl]-4-fluorobenzoic acid is obtained analogously from ethyl 2-[2-amino-4-(1,3-dihydroisoindole-2-carbonyl)quinazolin-6-yl]-4-fluorobenzoate;

Yield: 58%; LC-MS retention time: 2.00 min (method 1).

The compound 2-[2-amino-4-(1,3-dihydroisoindole-2-carbonyl)quinazolin-6-yl]-5-fluorobenzoic acid is obtained analogously from ethyl 2-[2-amino-4-(1,3-dihydroisoindole-2-carbonyl)quinazolin-6-yl]-5-fluorobenzoate;

Yield: 58%; LC-MS retention time: 1.99 min (method 1).

Synthesis of {2-amino-6-[2-(4-methylpiperazine-1-carbonyl)phenyl]quinazolin-4-yl}-(1,3-dihydroisoindol-2-yl)methanone ("A34") by method A

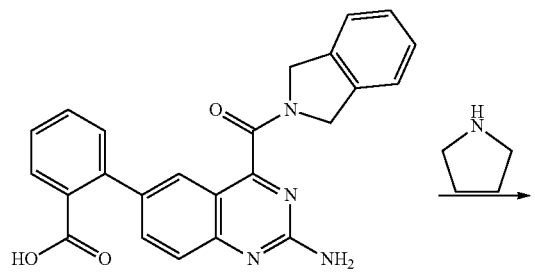

175.9 mg of O-(benzotriazol-1-yl)-N,N,N',N'-tetramethyluronium tetrafluoroborate (TBTU), 33.8 µl of pyrrolidine and 200.9 µl of 4-methylmorpholine are added to a solution of 150 mg of 2-[2-amino-4-(1,3-dihydroisoindole-2-carbonyl)quinazolin-6-yl]benzoic acid in 1 ml of dimethylformamide. The mixture is subsequently stirred at 25° C. for 12 h. The mixture is evaporated to dryness in vacuo, the residue is taken up in 1 ml of dimethyl sulfoxide and purified by chromatography (reversed phase HPLC).

Yield: 50 mg (30%) of {2-amino-6-[2-(4-methylpiperazine-1-carbonyl)-phenyl]quinazolin-4-yl}-(1,3-dihydroisoindol-2-yl)methanone;

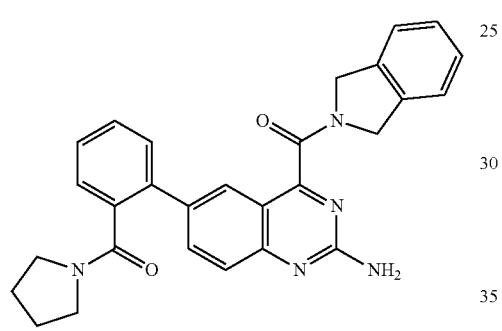

LC-MS retention time: 1.77 min (method 1);

$^1$H NMR (500 MHz, DMSO-d$_6$/TFA-d$_1$): δ [ppm] 8.071 (s, 1H), 8.004 (d, 1H), 7.855 (d, 1H), 7.716 (d, 1H), 7.547-7.498 (m, 2H), 7404-7.377 (m, 2H), 7.303 (t, 1H), 7.264 (t, 1H), 7.205 (d, 1H), 4.988 (s, 2H), 4.803 (s, 2H), 4.274 (s, 2H), 3.360 (s, 2H), 2.798 (bs, 2H), 1.750 (m, 4H).

The following compounds are obtained analogously

| No. | Structure and/or name | HPLC retention time [min] (method) | ESI-MS m/e = MW + 1 | NMR |
|---|---|---|---|---|
| "A22" | 2-[2-Amino-4-(1,3-dihydroisoindole-2-carbonyl)quinazolin-6-yl]-N-(2-hydroxyethyl)-N-methylbenzamide | 1.55 (1) | 468.53 | $^1$H NMR (400 MHz, DMSO-d$_6$/TFA): δ [ppm] 8.154-8.083(m, 1H), 8.040(m, 1H), 7.877(d, 1H), 7.535-7.459(m, 4H), 7.418-7.297(m, 3H), 7.251(m, 1H), 5.053-5.043(m, 2H), 4.851-4.819(m, 2H), 3.367-3.318(m, 2H), 3.268-2.674(m, 3H) |

| No. | Structure and/or name | HPLC retention time [min] (method) | ESI-MS m/e = MW + 1 | NMR |
|---|---|---|---|---|
| "A23" | {2-Amino-6-[2-(4-hydroxypiperidine-1-carbonyl)phenyl]quinazolin-4-yl}-(1,3-dihydroisoindol-2-yl)methanone | 1.54 (1) | 494.57 | $^1$H NMR (400 MHz, DMSO-$d_6$/TFA): δ [ppm] 8.075(d, 1H), 8.007(s, 1H), 7.815(d, 1H), 7.530-7.439(m, 4H), 7.352-7.277(m, 3H), 7.225(d, 1H), 5.041(s, 2H), 4.793(s, 2H), 3.665-3.551(m, 2H), 3.165-2.779(m, 3H), 1.494-1.130(m, 4H). |
| "A24" | 2-[2-Amino-4-(1,3-dihydroisoindole-2-carbonyl)quinazolin-6-yl]-N-ethyl-N-(2-hydroxyethyl)benzamide | 1.64 (1) | 482.56 | $^1$H NMR (400 MHz, DMSO-$d_6$/TFA): δ [ppm] 8.156-8.091(m, 2H), 7.838(d, 1H), 7.544-7.458(m, 4H), 7.397-7.303(m, 3H), 7.254(d, 1H), 5.058-5.047(m, 2H), 4.842(s, 2H), 3.310-2.937(m, 6H), 8.810(t, 3H). |
| "A35" | {2-Amino-6-[2-(3-hydroxymethylpyrrolidine-1-carbonyl)phenyl]quinazolin-4-yl}-(1,3-dihydroisoindol-2-yl)methanone | 1.55 | 494.57 | $^1$H NMR (400 MHz, DMSO-$d_6$/TFA): δ [ppm] 8.030-8.035(m, 1H), 8.012-7.989(m, 1H), 7.791(d, 1H), 7.470-7.454(m, 2H), 7.426-7.325(m, 3H), 7.267(t, 1H), 7.223(t, 1H), 7.159(d, 1H), 4.997-4.986(m, 2H), 4.763(s, 2H), 3.290-3.215(m, 1H), 3.151-2.707(m, 5H), 2.095-2.026(m, 1H), 1.670-1.609(m, 1H), 1.420-1.334(m, 1H). |

| No. | Structure and/or name | HPLC retention time [min] (method) | ESI-MS m/e = MW + 1 | NMR |
|---|---|---|---|---|
| "A36" | {2-Amino-6-[2-(3-hydroxypyrrolidine-1-carbonyl)phenyl]quinazolin-4-yl}-(1,3-dihydroisoindol-2-yl)methanone | 1.55 (1) | 480.54 | $^1$H NMR (400 MHz, DMSO-d$_6$/TFA): δ [ppm] 8.116-8.061(m, 1H), 7.998(d, 1H), 7.805-7.774(m, 1H), 7.531-7.369(m, 5H), 7.323 (t, 1H), 7.279(t, 1H), 7.216(d, 1H), 5.027-5.001(m, 2H), 4.798-4.778(m, 2H), 4.096-4.036(m, 1H), 3.284-2.682(m, 4H), 1.742-1.570(m, 2H). |
| "A37" | Methyl 1-{2-[2-amino-4-(1,3-dihydroisoindole-2-carbonyl)quinazolin-6-yl]-benzoyl}pyrrolidine-2-carboxylate and therefrom by ester hydrolysis 1-{2-[2-amino-4-(1,3-dihydroisoindole-2-carbonyl)quinazolin-6-yl]benzoyl}-pyrrolidine-2-carboxylic acid ("A44") | 1.78 (1) | 522.58 | |
| "A38" | 2-[2-Amino-4-(1,3-dihydroisoindole-2-carbonyl)quinazolin-6-yl]-N,N-dimethylbenzamide | 1.70 (1) | 438.50 | $^1$H NMR (400 MHz, DMSO-d$_6$/TFA): δ [ppm] 8.082-8.055(m, 1H), 7.945(d, 1H), 7.815(d, 1H), 7.519-7.299 (m, 7H), 7.214(d, 1H), 5.012-4.995(m, 2H), 4.838-4.792(m, 2H), 2.672-2.598(m, 6H). |

| No. | Structure and/or name | HPLC retention time [min] (method) | ESI-MS m/e = MW + 1 | NMR |
|---|---|---|---|---|
| "A39" | 2-[2-Amino-4-(1,3-dihydroisoindole-2-carbonyl)quinazolin-6-yl]-N-ethyl-N-methylbenzamide | 1.77 (1) | 452.53 | $^1$H NMR (400 MHz, DMSO-d$_6$/TFA): δ [ppm] 8.082-8.036(m, 1H), 8.000-7.979(m, 1H), 7.815-7.791(m, 1H), 7.498-7.412(m, 4H), 7.322-7.244(m, 3H), 7.202(d, 1H), 5.006 (s, 2H), 4.794-4.765(m, 2H), 3.125-2.519(m, 5H), 0.794-0.755(m, 3H). |
| "A40" | 2-[2-Amino-4-(1,3-dihydroisoindole-2-carbonyl)quinazolin-6-yl]-N,N-diethyl-benzamide | 1.87 (1) | 466.56 | $^1$H NMR (400 MHz, DMSO-d$_6$/TFA): δ [ppm] 8.122-8.099(m, 2H), 7.854(d, 1H), 7.542-7.463(m, 4H), 7.374-7.302(m, 3H), 7.246(d, 1H), 5.063(s, 2H), 4.833(s, 2H), 3.165-2.944 (m, 4H), 0.829-0.783(m, 6H). |
| "A41" | 2-[2-Amino-4-(1,3-dihydroisoindole-2-carbonyl)quinazolin-6-yl]-N-ethylbenz-amide | 1.65 (1) | 438.50 | $^1$H NMR (400 MHz, DMSO-d$_6$/TFA): δ [ppm] 8.097-8.076(m, 1H), 8.021(d, 1H), 7.837(d,1H), 7.560-7.527(m, 1H), 7.483-7.459(m, 4H), 7.358(t, 1H), 7.317(t, 1H), 7.253(d, 1H), 5.050(s, 2H), 4.822(s, 2H), 2.976-2.933(q, 2H), 0.853(t, 3H). |
| "A42" | {2-Amino-6-[2-(2-methylpyrrolidine-1-carbonyl)phenyl]quinazolin-4-yl}-(1,3-dihydroisoindol-2-yl)methanone | 1.85 (1) | 478.57 | |
| "A46" | 2-[2-Amino-4-(1,3-dihydroisoindole-2-carbonyl)quinazolin-6-yl]-N-cyclobutyl-benzamide | 1.76 (1) | 464.54 | $^1$H NMR (400 MHz, DMSO-d$_6$/TFA): δ [ppm] 8.019(m, 1H), 7.971(d, 1H), 7.790(d, 1H), 7.533-7.501(m, 1H), 7.450-7.492(m, 4H), 7.334(t, 1H), 7.297(t, 1H), 7.227(t, 1H), 5.010(s, 2H), 4.789(s, 2H), 3.960(m, 1H), 1.948-1.899(m, 2H), 1.730-1.651(m, 2H), 1.474-1.336(m, 2H). |
| "A47" | 2-[2-Amino-4-(1,3-dihydroisoindole-2-carbonyl)quinazolin-6-yl]-N-tert-butylbenz-amide | 1.85 (1) | 466.56 | $^1$H NMR (400 MHz, DMSO-d$_6$/TFA): δ [ppm] 8.048-8.027(m, 2H), 7.989(d, 1H), 7.497-7.372(m, 5H), 7.319(t, 1H), 7.297(t, 1H), 7.195(d, 1H), 5.007 (s, 2H), 4.800(s, 2H), 1.083(s, 9H). |
| "A48" | 2-[2-Amino-4-(1,3-dihydroisoindole-2-carbonyl)quinazolin-6-yl]-N-cyclopropyl-benzamide | 1.65 (1) | 450.51 | $^1$H NMR (400 MHz, DMSO-d$_6$/TFA): δ [ppm] 8.037-8.015(m, 1H), 7.965(d, 1H), 7.807(d, 1H), 7.520-7.487(m, 1H), 7.443-7.396 (m, 4H), 7.314(t, 1H), 7.271(t, 1H), 7.212 (d, 1H), 5.017(s, 2H), 4.796(s, 2H), 2.400 (m, 1H), 0.331(m, 2H), 0.249(m, 2H). |
| "A49" | {2-Amino-6-[2-(3,3-difluoropyrrolidine-1-carbonyl)phenyl]quinazolin-4-yl}-(1,3-dihydroisoindol-2-yl)methanone | 2.57 (2) | 500.52 | $^1$H NMR (400 MHz, DMSO-d$_6$/TFA): δ [ppm] 8.093-8.063(m, 1H), 8.030-7.995(m, 1H), 7.820(d, 1H), 7.571-7.522(m, 2H), 7.499-7.417(m, 3H), 7.312(t, 1H), 7.297(t, 1H), 7.206(d, 1H), 4.997(s, 2H), 4.776(d, 2H), 3.680-3.304(m, 4H), 2.345-2.202(m, 2H). |

-continued

| No. | Structure and/or name | HPLC retention time [min] (method) | ESI-MS m/e = MW + 1 | NMR |
|---|---|---|---|---|
| "A54" | {2-Amino-6-[2-(azetidine-1-carbonyl)-phenyl]quinazolin-4-yl}-(1,3-dihydro-isoindol-2-yl)methanone | 2.38 (2) | 450.51 | $^1$H NMR (400 MHz, DMSO-d$_6$/TFA): δ [ppm] 8.136-8.115(m, 1H), 8.047(d, 1H), 7.866(d, 1H), 7.571-7.451(m, 5H), 7.347(t, 1H), 7.307(t, 1H), 7.253(d, 1H), 5.053(s, 2H), 4.850(s, 2H), 3.884-3.826(m, 4H), 2.173-2.112(m, 2H). |
| "A55" | 2-[2-Amino-4-(1,3-dihydroisoindole-2-carobnyl)quinazolin-6-yl]-N-(2-dimethyl-aminoethyl)-N-ethylbenzamide | 2.20 (2) | 509.63 | $^1$H NMR (400 MHz, DMSO-d$_6$/TFA): δ [ppm] 8.091-8.069(m, 1H), 8.006(d, 1H), 7.931(s, 1H), 7.839 (d, 1H), 7.551-7.404(m, 4H), 7.309(t, 1H), 7.267(t, 1H), 7.199(d, 1H), 5.000(s, 2H), 4.783(s, 2H), 3.534-2.990(m, 6H), 2.870(s, 3H), 2.723(s, 3H), 0.788(t, 3H). |
| "A56" | 2-[2-Amino-4-(1,3-dihydroisoindole-2-carbonyl)quinazolin-6-yl]-N-tert-butyl-N-methylbenzamide | 2.67 (2) | 480.58 | $^1$H NMR (400 MHz, DMSO-d$_6$/TFA): δ [ppm] 8.049-8.030(m, 2H), 7.824(d, 1H), 7.520-7.456(m, 4H), 7.370-7.301(m, 3H), 7.258(d, 1H), 5.031(s, 2H), 4.872(s, 2H), 2.645(s, 3H), 1.227(s, 9H). |
| "A57" | {2-Amino-6-[2-(2,5-dimethylpyrrolidine-1-carbonyl)phenyl]quinazolin-4-yl}-(1,3-dihydroisoindol-2-yl)methanone | 2.65 (2) | 492.59 | |

-continued

| No. | Structure and/or name | HPLC retention time [min] (method) | ESI-MS m/e = MW + 1 | NMR |
|---|---|---|---|---|
| "A62" | {2-Amino-6-[2-((S)-3-fluoropyrrolidine-1-carbonyl)phenyl]quinazolin-4-yl}-(1,3-dihydroisoindol-2-yl)methanone | 1.95 (1) | 482.53 | $^1$H NMR (400 MHz, DMSO-$d_6$/TFA): δ [ppm] 8.14-8.08(m, 1H), 8.03(dd, J = 1.9, 10.5, 1H), 7.84 (d, J = 8.7, 1H), 7.58(dd, J = 4.2, 7.6, 2H), 7.54-7.49(m, 1H), 7.49-7.41(m, 2H), 7.36(t, J = 7.3, 1H), 7.31(t, J = 7.4, 1H), 7.25(d, J = 7.5, 1H), 5.26-5.09(m, 1H), 5.08-4.99(m, 2H), 4.85-4.74(m, 2H), 3.56-3.04(m, 4H), 2.02-1.83(m, 2H). |
| "A63" | {2-Amino-6-[2-((R)-2-methylpyrrolidine-1-carbonyl)phenyl]quinazolin-4-yl}-(1,3-dihydroisoindol-2-yl)methanone | 2.07 (1) | 478.57 | |
| "A70" | 2-[2-Amino-4-(1,3-dihydroisoindole-2-carbonyl)quinazolin-6-yl]-N,N-diethyl-4-fluorobenzamide | 2.11 (1) | 484.55 | $^1$H NMR (400 MHz, DMSO-$d_6$/TFA): δ [ppm] 8.04(dd, J = 2.0, 8.7, 1H), 8.01(d, J = 1.8, 1H), 7.79 (d, J = 8.7, 1H), 7.54(dd, J = 5.4, 8.6, 1H), 7.44(d, J = 7.5, 1H), 7.36-7.30(m, 1H), 7.28(t, J = 7.3, 1H), 7.21(d, J = 8.6, 1H), 7.19(dd, J = 2.8, 8.9, 1H), 5.01(s, 2H), 4.77(bs, 2H), 3.13(bs, 2H), 2.88(s, 2H), 0.79-0.72(m, 6H). |
| "A71" | 2-[2-Amino-4-(1,3-dihydroisoindole-2-carbonyl)quinazolin-6-yl]-N,N-diethyl-5-fluorobenzamide | 2.65 (2) | 484.55 | $^1$H NMR (400 MHz, DMSO-$d_6$/TFA): δ [ppm] 8.04(dd, J = 2.0, 8.7, 1H), 8.01(d, J = 1.8, 1H), 7.79(d, J = 8.7, 1H), 7.54(dd, J = 5.4, 8.6, 1H), 7.44(d, J = 7.5, 1H), 7.37-7.30(m, 2H), 7.28(t, J = 7.3, 1H), 7.21(d, J = 8.6, 1H), 7.19(dd, J = 2.8, 8.9, 1H), 5.01(s, 2H), 4.77(s, 2H), 3.13(s, 2H), 2.88(s, 2H), 0.81-0.68(m, 6H). |
| "A72" | {2-Amino-6-[2-((S)-2-methylpyrrolidine-1-carbonyl)phenyl]quinazolin-4-yl}-(1,3-dihydroisoindol-2-yl)methanone | 2.57 (2) | 478.57 | |

-continued

| No. | Structure and/or name | HPLC retention time [min] (method) | ESI-MS m/e = MW + 1 | NMR |
|---|---|---|---|---|
| "A73" | 2-[2-Amino-4-(1,3-dihydroisoindole-2-carbonyl)quinazolin-6-yl]-N,N-bis-(2-hydroxyethyl)benzamide | 1.64 (1) | 498.55 | $^1$H NMR (400 MHz, DMSO-d$_6$/TFA): δ [ppm] 8.15(dd, J = 2.0, 8.7, 1H), 8.12(t, J = 1.9, 1H), 7.84(d, J = 8.7, 1H), 7.55-7.48(m, 3H), 7.46(d, J = 7.5, 1H), 7.43(d, J = 7.3, 1H), 7.34(dt, J = 7.2, 19.8, 2H), 7.26(d, J = 7.4, 1H), 5.04(d, J = 20.6, 2H), 4.85(d, J = 13.9, 2H), 3.59-2.89(m, 8H). |
| "A74" | 2-[2-Amino-4-(1,3-dihydroisoindole-2-carbonyl)quinazolin-6-yl]-N-ethyl-4,5-difluorobenzamide | 1.92 (1) | 474.48 | $^1$H NMR (400 MHz, DMSO-d$_6$/TFA): δ [ppm] 8.06(dd, J = 2.0, 8.7, 1H), 8.01(d, J = 1.8, 1H), 7.82(d, J = 8.7, 1H), 7.57(ddd, J = 7.9, 10.9, 18.5, 2H), 7.47(d, J = 7.4, 1H), 7.34(dt, J = 7.2, 20.2, 2H), 7.28-7.23(m, 1H), 5.05(s, 2H), 4.82(s, 2H), 2.95(q, J = 7.2, 2H), 0.88(t, J = 7.2, 3H). |
| "A75" | 2-[2-Amino-4-(1,3-dihydroisoindole-2-carbonyl)quinazolin-6-yl]-N-ethyl-4,5-difluoro-N-(2-hydroxyethyl)benzamide | 1.90 | 518.54 | $^1$H NMR (400 MHz, DMSO-d$_6$/TFA): δ [ppm] 8.12-8.05(m, 2H), 7.82(dd, J = 2.9, 8.9, 1H), 7.63(td, J = 7.7, 11.5, 1H), 7.52(td, J = 8.2, 11.1, 1H), 7.47(d, J = 7.3, 1H), 7.34(dt, J =7.3, 20.8, 2H), 7.25(d, J = 7.5, 1H), 5.04(d, J = 4.3, 2H), 4.83(s, 2H), 3.43-2.78(m, 6H), 0.87-0.73(m, 3H). |
| "A76" | 2-[2-Amino-4-(1,3-dihydroisoindole-2-carbonyl)quinazolin-6-yl]-N-(2-dimethyl-aminoethyl)-N-ethyl-4,5-difluoro-benzamide | 1.63 (1) | 545.61 | $^1$H NMR (400 MHz, DMSO-d$_6$/TFA): δ [ppm] 8.12-8.06(m, 1H), 8.05(d, J = 1.9, 1H), 7.88(d, J = 8.7, 1H), 7.71-7.57(m, 2H), 7.49-7.44(m, 1H), 7.34(dt, J = 7.2, 21.1, 2H), 7.25 (d, J = 7.5, 1H), 5.05(s, 2H), 4.83(s, 2H), 3.56(s, 2H), 3.17-2.95(m, 4H), 2.81-2.68(m, 6H), 0.88-0.75(m, 3H). |
| "A77" | 2-[2-Amino-4-(1,3-dihydroisoindole-2-carbonyl)quinazolin-6-yl]-N-ethyl-4,5-difluoro-N-methylbenzamide | 2.03 (1) | 488.51 | $^1$H NMR (400 MHz, DMSO-d$_6$/TFA): δ [ppm] 8.10-8.00 (m, 2H), 7.84(dd, J = 3.3, 8.7, 1H), 7.68-7.62(m, 1H), 7.54-7.44(m, 2H), 7.39-7.28(m, 2H), 7.24(dd, J = 7.2, 14.1, 1H), 5.05(s, 2H), 4.82(d, J = 13.9, 2H), 3.16(q, J = 7.2, 2H), 2.65(s, 3H), 0.83(t, J = 7.1, 14.2, 3H). |
| "A78" | {2-Amino-6-[4,5-difluoro-2-(pyrrolidine-1-carbonyl)phenyl]quinazolin-4-yl}-(1,3-dihydroisoindol-2-yl)methanone | 2.02 (1) | 500.52 | $^1$H NMR (400 MHz, DMSO-d$_6$/TFA): δ [ppm] 8.10(dd, J = 2.0, 8.7, 1H), 8.01(d, J = 1.9, 1H), 7.85(d, J = 8.7, 1H), 7.66(dd, J = 7.6, 11.3, 1H), 7.55 (dd, J = 8.1, 10.5, 1H), 7.48(d, J = 7.5, 1H), 7.34(dt, J = 7.2, 22.3, 2H), 7.24 (d, J = 7.5, 1H), 5.04(s, 2H), 4.81(s, 2H), 3.17(t, J = 6.4, 2H), 3.03(t, J = 6.0, 2H), 1.71-1.62(m, 4H). |
| "A79" | {2-Amino-6-[4,5-difluoro-2-(2-methyl-pyrrolidine-1-carbonyl)phenyl]quinazolin-4-yl}-(1,3-dihydroisoindol-2-yl)methanone | 2.16 (1) | 514.55 | $^1$H NMR (400 MHz, DMSO-d$_6$/TFA): δ [ppm] 8.11-8.07(m, 2H), 7.85(dd, J = 6.5, 10.8, 1H), 7.63(dd, J = 7.7, 17.3, 1H), 7.49(dd, J = 8.6, 14.5, 2H), 7.34(dt, J = 7.3, 21.8, 2H), 7.25(d, J = 7.3, 1H), 5.06(d, J = 6.4, 2H), 4.88-4.76(m, 2H), 3.91-3.77(m, 1H), 3.06-2.87(m, 1H), 1.82(dq, J = 7.4, 15.1, 1H), 1.74-1.59(m, 1H), 1.59-1.41(m, 1H), 1.41-1.24(m, 1H), 0.97-0.69(m, 3H). |
| "A80" | {2-Amino-6-[2-(azetidine-1-carbonyl)-4,5-difluorophenyl]quinazolin-4-yl}-(1,3-dihydroisoindol-2-yl)methanone | 1.97 (1) | 486.49 | $^1$H NMR (400 MHz, DMSO-d$_6$/TFA): δ [ppm] 8.10(dd, J = 2.0, 8.7, 1H), 8.05(d, J = 1.9, 1H), 7.85(d, J = 8.7, 1H), 7.65(dd, J = 7.6, 11.3, |

-continued

| No. | Structure and/or name | HPLC retention time [min] (method) | ESI-MS m/e = MW + 1 | NMR |
|---|---|---|---|---|
| | | | | 1H), 7.60(dd, J = 8.1, 10.4, 1H), 7.46(d, J = 7.4, 1H), 7.33(dt, J = 7.0, 20.5, 2H), 7.25(d, J = 7.3, 1H), 5.05(s, 2H), 4.84(s, 2H), 3.90(t, J = 7.6, 2H), 3.83(t, J = 7.7, 2H), 2.19-2.09(m, 2H). |
| "A81" | 2-[2-Amino-4-(1,3-dihydroisoindole-2-carbonyl)quinazolin-6-yl]-N-tert-butyl-4,5-difluorobenzamide | 2.12 (1) | 502.54 | $^1$H NMR (400 MHz, DMSO-d$_6$/TFA): δ [ppm] 8.04-7.98(m, 2H), 7.78(dd, J = 1.4, 8.0, 1H), 7.58-7.41(m, 3H), 7.37-7.26(m, 2H), 7.21(d, J = 7.3, 1H), 5.01(s, 2H), 4.80(s, 2H), 1.06(s, 9H). |
| "A83" | 2-[2-Amino-4-(1,3-dihydroisoindole-2-carbonyl)quinazolin-6-yl]-N-ethyl-5-fluorobenzamide | 1.83 (1) | 456.49 | $^1$H NMR (400 MHz, DMSO-d$_6$/TFA): δ [ppm] 8.05(dd, J = 2.0, 8.7, 1H), 7.99(d, J = 1.9, 1H), 7.82(d, J = 8.7, 1H), 7.53(dd, J = 5.4, 8.6, 1H), 7.47(d, J = 7.2, 1H), 7.38(dt, J = 2.9, 5.6, 1H), 7.37-7.26(m, 3H), 7.26(d, J = 7.2, 1H), 5.04(s, 2H), 4.81(s, 2H), 2.94(q, J = 7.2, 2H), 0.85(t, J = 7.2, 3H). |
| "A84" | 2-[2-Amino-4-(1,3-dihydroisoindole-2-carbonyl)quinazolin-6-yl]-N-ethyl-4,5-dimethoxybenzamide | 1.69 (1) | 498.55 | $^1$H NMR (400 MHz, DMSO-d$_6$): δ [ppm] 8.10(dd, J = 2.0, 8.7, 1H), 7.95(d, J = 1.7, 1H), 7.83(d, J = 8.7, 1H), 7.47(d, J = 7.3, 1H), 7.40-7.29(m, 2H), 7.25(d, J = 7.2, 1H), 7.08(s, 1H), 6.98(s, 1H), 5.06(s, 2H), 4.82(s, 2H), 3.86(s, 3H), 3.84(s, 3H), 2.93(q, J = 7.2, 2H), 0.84(t, J = 7.2, 3H). |
| "A85" | 2-[2-Amino-4-(1,3-dihydroisoindole-2-carbonyl)quinazolin-6-yl]-N-tert-butyl-4,5-dimethoxybenzamide | 1.89 (1) | 526.61 | $^1$H NMR (400 MHz, DMSO-d$_6$): δ [ppm] 8.06(dd, J = 1.9, 8.7, 1H), 8.01(d, J = 1.7, 1H), 7.81(d, J = 8.6, 1H), 7.46(d, J = 7.5, 1H), 7.33(dt, J = 7.2, 20.8, 2H), 7.22(d, J = 7.4, 1H), 7.02(s, 1H), 6.91(s, 1H), 5.04(s, 2H), 4.83(s, 2H), 3.85(s, 3H), 3.81(s, 3H), 1.09(s, 9H). |
| "A86" | 2-[2-Amino-4-(1,3-dihydroisoindole-2-carbonyl)quinazolin-6-yl]-4-chloro-N-ethylbenzamide | 1.99 (1) | 472.95 | $^1$H NMR (400 MHz, DMSO-d$_6$): δ [ppm] 8.12-8.06(m, 2H), 7.85(d, J = 8.6, 1H), 7.57-7.50(m, 3H), 7.46(d, J = 7.4, 1H), 7.39-7.29(m, 2H), 7.25(d, J = 7.3, 1H), 5.07(s, 2H), 4.84(s, 2H), 2.98(q, J = 7.3, 2H), 0.87(t, J = 7.2, 3H). |
| "A87" | 2-[2-Amino-4-(1,3-dihydroisoindole-2-carbonyl)quinazolin-6-yl]-4-chloro-N,N-diethylbenzamide | 2.14 (1) | 501.00 | $^1$H NMR (400 MHz, DMSO-d$_6$): δ [ppm] 8.17-8.09(m, 2H), 7.86(d, J = 8.7, 1H), 7.60(d, J = 2.0, 1H), 7.54(dd, J = 2.1, 8.2, 1H), 7.47(d, J = 7.4, 1H), 7.40-7.29(m, 3H), 7.25(d, J = 7.4, 1H), 5.07(s, 2H), 4.84(s, 2H), 3.33-2.84(m, 4H), 0.81(td, J = 1.6, 7.0, 6H). |
| "A88" | 2-[2-Amino-4-(1,3-dihydroisoindole-2-carbonyl)quinazolin-6-yl]-N,N-diethyl-4,5-dimethoxybenzamide | 1.88 (1) | 526.61 | $^1$H NMR (400 MHz, DMSO-d$_6$): δ [ppm] 8.15(dd, J = 2.0, 8.7, 1H), 8.04(d, J =1.9, 1H), 7.83(d, J = 8.7, 1H), 7.48(d, J =7.3, 1H), 7.34(dt, J = 7.2, 18.0, 2H), 7.25(d, J = 7.4, 1H), 7.02(s, 1H), 6.89(s, 1H), 5.06(s, 2H), 4.81(s, 2H), 3.84(s, 3H), 3.83(s, 3H), 3.22-2.76(m, 4H), 0.78(dd, J = 7.0, 12.1, 6H). |
| "A89" | 2-[2-Amino-4-(1,3-dihydroisoindole-2-carbonyl)quinazolin-6-yl]-N-tert-butyl-4-chlorobenzamide | 2.13 (1) | 501.00 | $^1$H NMR (400 MHz, DMSO-d$_6$): δ [ppm] 8.12(d, J = 1.7, 1H), 8.08(dd, J = 1.9, 8.7, 1H), 7.84(d, J = 8.7, 1H), 7.53-7.44(m, 4H), 7.39-7.28(m, 2H), 7.23 (d, J = 7.2, 1H), 5.07(s, 2H), 4.86(s, 2H), 1.12(s, 9H). |
| "A90" | 2-[2-Amino-4-(1,3-dihydroisoindole-2-carbonyl)quinazolin-6-yl]-4-chloro-N-ethyl-N-(2-hydroxyethyl)benzamide | 1.94 (1) | 517.00 | $^1$H NMR (400 MHz, DMSO-d$_6$): δ [ppm] 8.19-8.09(m, 2H), 7.85(dd, J = 1.8, 9.0, 1H), 7.59(dd, J = 2.0, 6.0, 1H), 7.57-7.52(m, 1H), 7.49-7.40(m, 2H), 7.39-7.28(m, 2H), 7.25(d, J = 7.4, 1H), 5.07(d, J = 4.2, 2H), 4.86(s, 2H), 3.47-2.85(m, 6H), 0.91-0.73(m, 3H). |

Synthesis of "8" by method B

Preparation of 2-[2-amino-4-(1,3-dihydroisoindole-2-carbonyl)quinazolin-6-yl]-N,N-diethyl-4,5-difluorobenzamide ("A69")

Step 1: 2-Bromo-N,N-diethyl-4,5-difluorobenzamide

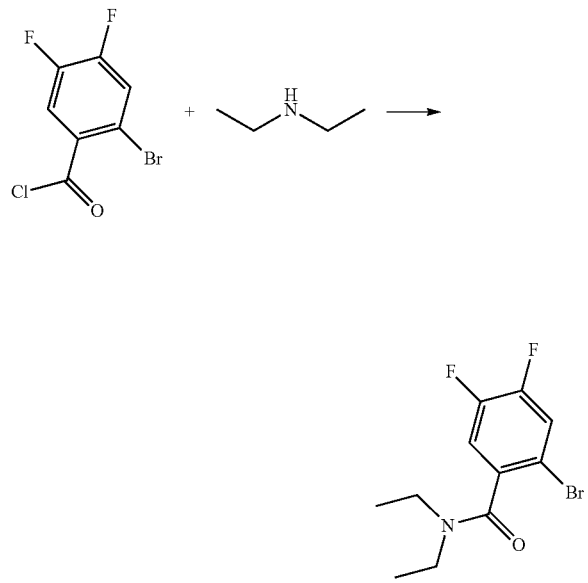

1.05 g of 2-bromo-4,5-difluorobenzoyl chloride in 5 ml of DCM are added dropwise with stirring to a solution of 846.9 µl of diethylamine in 5 ml of DCM. The mixture is subsequently stirred at RT for 1 h. The mixture is then extracted a number of times against water (pH 9), the organic phase is dried and purified by column chromatography.

Yield: 1 g (83%) of 2-bromo-N,N-diethyl-4,5-difluorobenzamide;
LC-MS retention time: 1.73 min (method 1).
The following are obtained analogously:

2-bromo-N-ethyl-5-fluorobenzamide;
LC-MS retention time: 1.55 min (method 1);

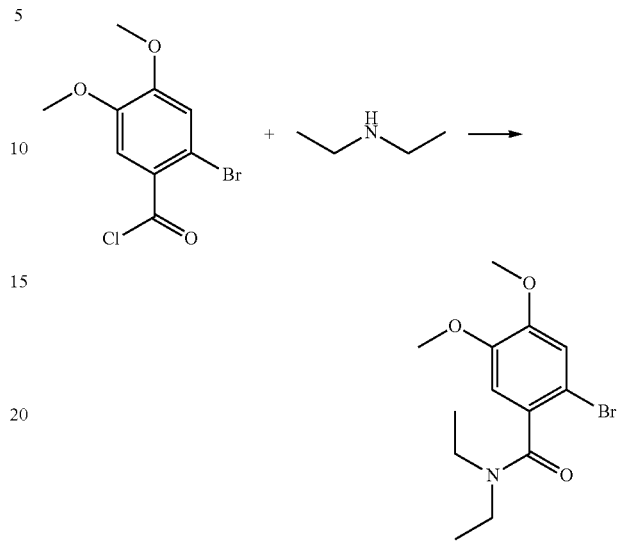

2-bromo-N,N-diethyl-4,5-dimethoxybenzamide;
HPLC retention time: 2.52 min (method 2);

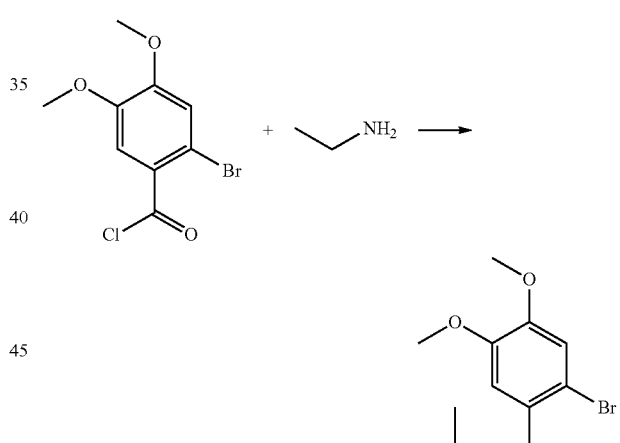

2-bromo-N-ethyl-4,5-dimethoxybenzamide;
LC-MS retention time: 1.53 min (method 1);

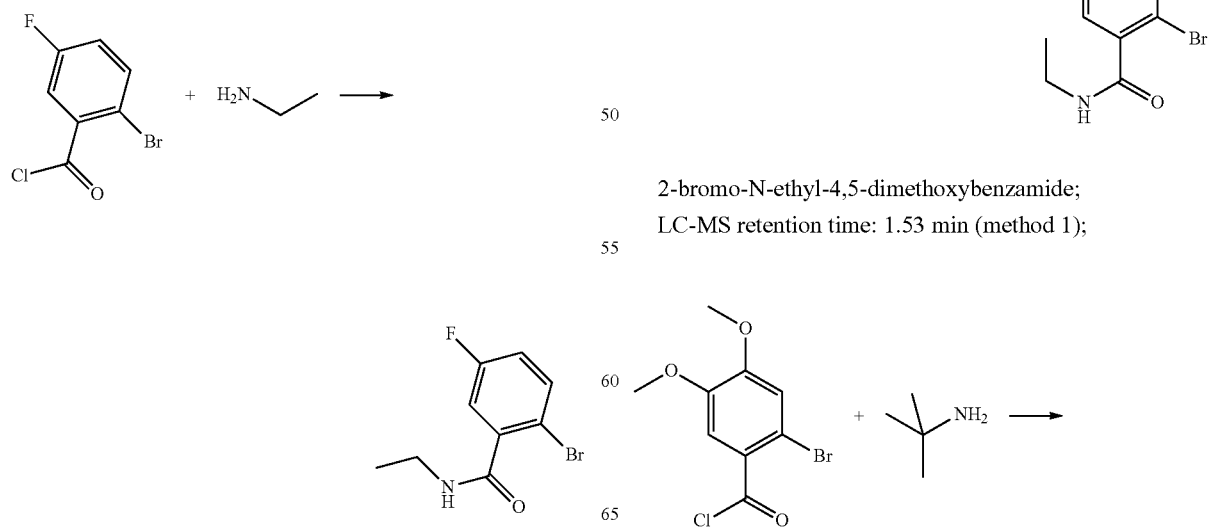

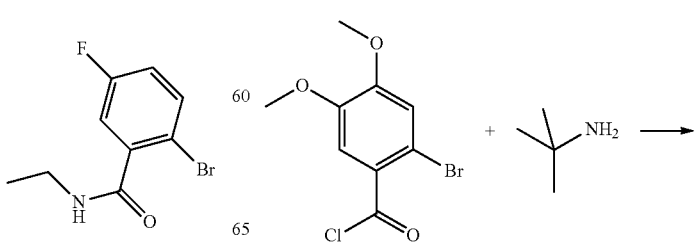

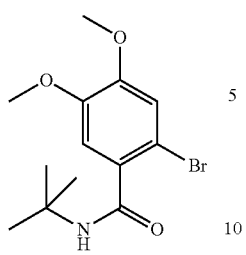

2-bromo-N-tert-butyl-4,5-dimethoxybenzamide;
LC-MS retention time: 2.02 min (method 1);

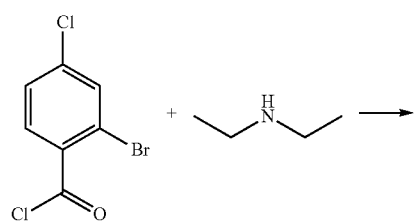

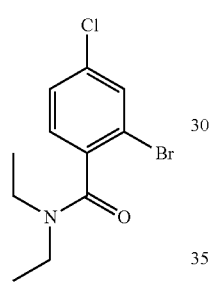

2-bromo-4-chloro-N,N-diethylbenzamide;
LC-MS retention time: 2.24 min (method 1);

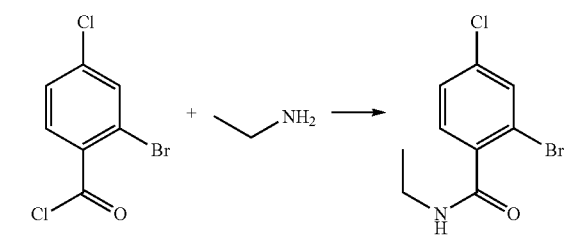

2-bromo-4-chloro-N-ethylbenzamide;
LC-MS retention time: 1.53 min (method 1);

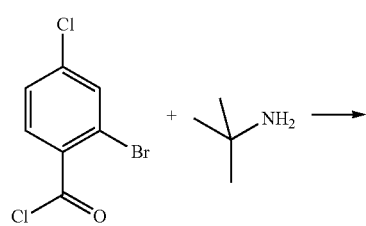

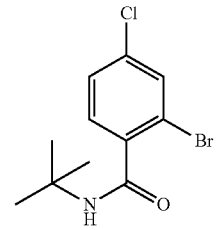

2-bromo-4-chloro-N-tert-butylbenzamide;
HPLC retention time: 2.26 min (method 2);

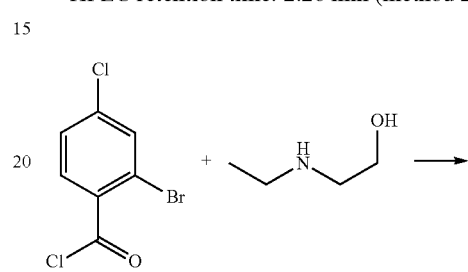

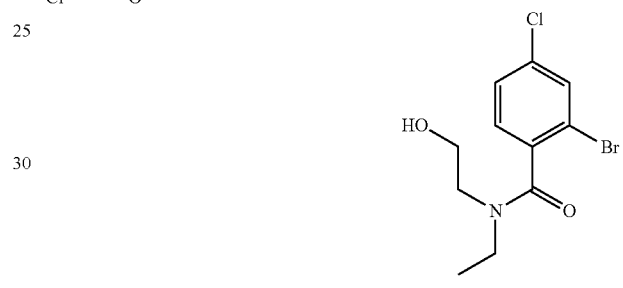

2-bromo-4-chloro-N-ethyl-N-(2-hydroxyethyl)benzamide;
LC-MS retention time: 1.84 min (method 1).

Step 2: 2-[2-Amino-4-(1,3-dihydroisoindole-2-carbonyl)quinazolin-6-yl]-N,N-diethyl-4,5-difluorobenzamide ("A69")

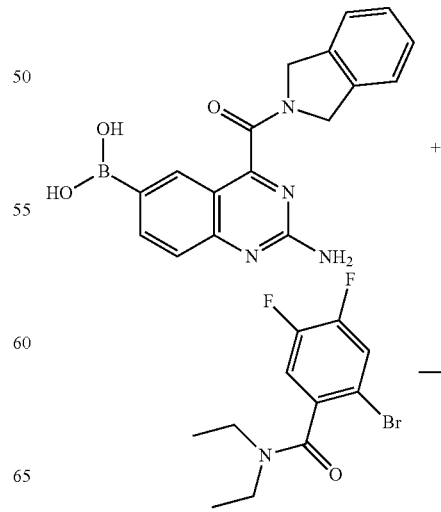

-continued

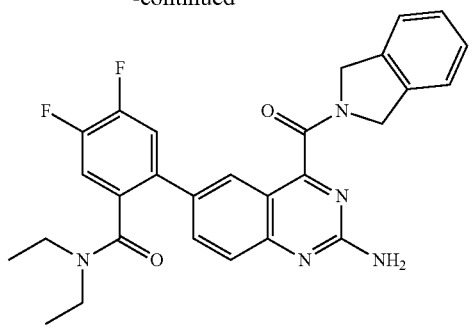

1.05 g of 2-bromo-N,N-diethyl-4,5-difluorobenzamide, 0.99 g of potassium carbonate, 0.6 µl of water and 146.6 mg of [1,1'-bis(diphenylphosphino)-ferrocene]palladium(II) dichloride are added to a solution of 1.2 g of 2-amino-6-boronyl-4-(1,3-dihydroisoindol-2-ylcarbonyl)quinazoline in 100 ml of ethanol under argon. The mixture is heated at 120° C. for 30 min, giving a clear solution. The hot solution is filtered through kieselguhr and purified by column chromatography.

Yield: 710 mg (39%) of 2-[2-amino-4-(1,3-dihydroisoindole-2-carbonyl)-quinazolin-6-yl]-N,N-diethyl-4,5-difluorobenzamide;

HPLC retention time: 2.72 min (method 2);

$^1$H NMR (500 MHz, DMSO-d$_6$/TFA) δ [ppm] 8.07 (dd, J=2.1, 8.6, 2H), 7.82 (d, J=9.0, 1H), 7.65 (dd, J=7.7, 11.3, 1H), 7.53-7.44 (m, 2H), 7.36 (t, J=7.3, 1H), 7.32 (t, J=7.3, 1H), 7.25 (d, J=7.4, 1H), 5.04 (s, 2H), 4.81 (s, 2H), 3.32-3.03 (m, 2H), 3.01-2.74 (m, 2H), 0.86-0.72 (m, 6H).

The following are obtained analogously:

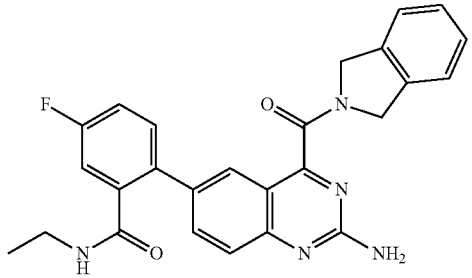 [SMILES: CCNC(=O)c1cc(F)ccc1-c1ccc2nc(N)nc(C(=O)N3Cc4ccccc4C3)c2c1]

2-[2-amino-4-(1,3-dihydroisoindole-2-carbonyl)quinazolin-6-yl]-N-ethyl-4,5-difluorobenzamide;
LC-MS retention time: 1.83 min (method 1);

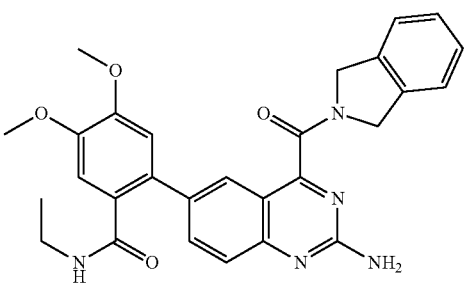 [SMILES: CCNC(=O)c1cc(OC)c(OC)cc1-c1ccc2nc(N)nc(C(=O)N3Cc4ccccc4C3)c2c1]

2-[2-amino-4-(1,3-dihydroisoindole-2-carbonyl)quinazolin-6-yl]-N,N-diethyl-4,5-dimethoxybenzamide;
LC-MS retention time: 1.88 min (method 1);

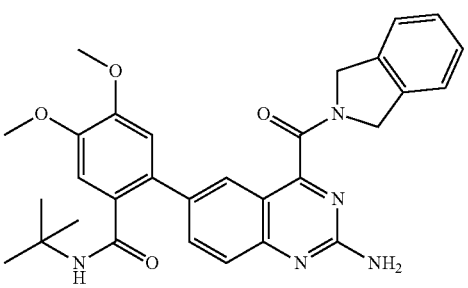 [SMILES: COc1cc(C(=O)NC(C)(C)C)c(-c2ccc3nc(N)nc(C(=O)N4Cc5ccccc5C4)c3c2)cc1OC]

2-[2-amino-4-(1,3-dihydroisoindole-2-carbonyl)quinazolin-6-yl]-N-ethyl-4,5-dimethoxybenzamide;
LC-MS retention time: 1.69 min (method 1);

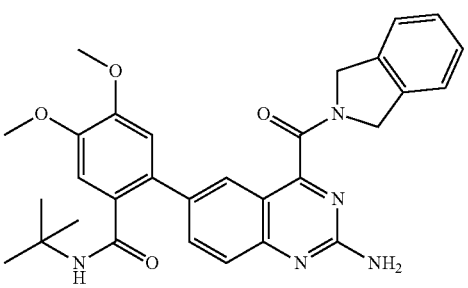 [SMILES: COc1cc(C(=O)NC(C)(C)C)c(-c2ccc3nc(N)nc(C(=O)N4Cc5ccccc5C4)c3c2)cc1OC]

2-[2-amino-4-(1,3-dihydroisoindole-2-carbonyl)quinazolin-6-yl]-N-tert-butyl-4,5-dimethoxybenzamide;
LC-MS retention time: 1.89 min (method 1);

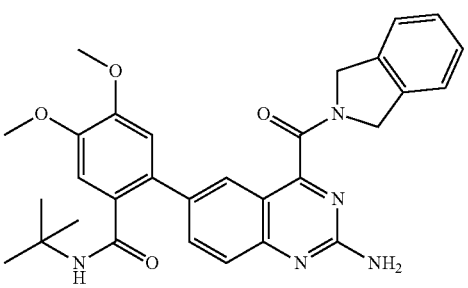 [SMILES: COc1cc(C(=O)NC(C)(C)C)c(-c2ccc3nc(N)nc(C(=O)N4Cc5ccccc5C4)c3c2)cc1OC]

2-[2-amino-4-(1,3-dihydroisoindole-2-carbonyl)quinazolin-6-yl]-4-chloro-N,N-diethylbenzamide;
LC-MS retention time: 2.14 min (method 1);

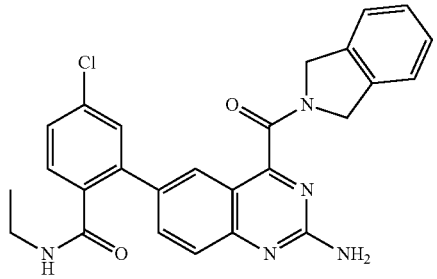 [SMILES: CCNC(=O)c1ccc(Cl)cc1-c1ccc2nc(N)nc(C(=O)N3Cc4ccccc4C3)c2c1]

2-[2-amino-4-(1,3-dihydroisoindole-2-carbonyl)quinazolin-6-yl]-4-chloro-N-ethylbenzamide;
LC-MS retention time: 1.99 min (method 1);

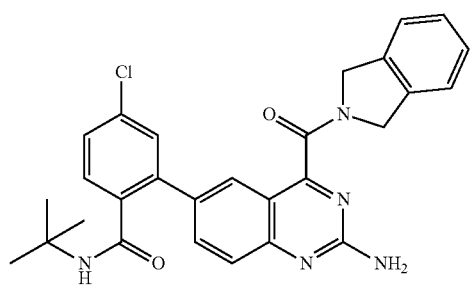 [SMILES: CC(C)(C)NC(=O)c1ccc(Cl)cc1-c1ccc2nc(N)nc(C(=O)N3Cc4ccccc4C3)c2c1]

2-[2-amino-4-(1,3-dihydroisoindole-2-carbonyl)quinazolin-6-yl]-4-chloro-N-tert-butylbenzamide;
LC-MS retention time: 2.13 min (method 1);

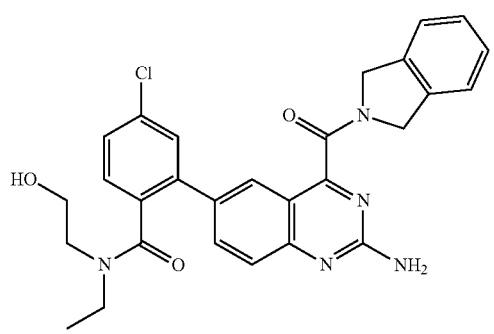 [SMILES: CCN(CCO)C(=O)c1ccc(Cl)cc1-c1ccc2nc(N)nc(C(=O)N3Cc4ccccc4C3)c2c1]

2-[2-amino-4-(1,3-dihydroisoindole-2-carbonyl)quinazolin-6-yl]-4-chloro-N-ethyl-N-(2-hydroxyethyl)benzamide;
LC-MS retention time: 1.95 min (method 1).

Preparation of {2-amino-6-[2-(3-aminopyrrolidine-1-carbonyl)phenyl]quinazolin-4-yl}-(1,3-dihydroisoindol-2-yl)methanone ("A43")

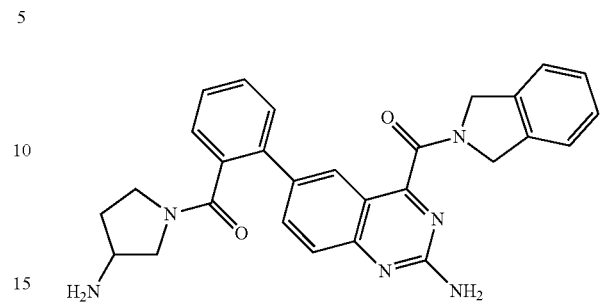

The product is obtained analogously to "A34" by reaction of 2-[2-amino-4-(1,3-dihydroisoindole-2-carbonyl)quinazolin-6-yl]benzoic acid with tert-butyl pyrrolidin-3-ylcarbamate. The resultant tert-butyl (1-{2-[2-amino-4-(1,3-dihydroisoindole-2-carbonyl)quinazolin-6-yl]benzoyl}pyrrolidin-3-yl)carbamate is treated directly with 1 M HCl in dioxane, causing the protecting group to be cleaved. The purification is carried out by means of column chromatography;
LC-MS retention time: 1.82 min (method 1).

Preparation of 1-{2-[2-amino-4-(1,3-dihydroisoindole-2-carbonyl)quinazolin-6-yl]benzoyl}pyrrolidine-2-methylamide ("A50")

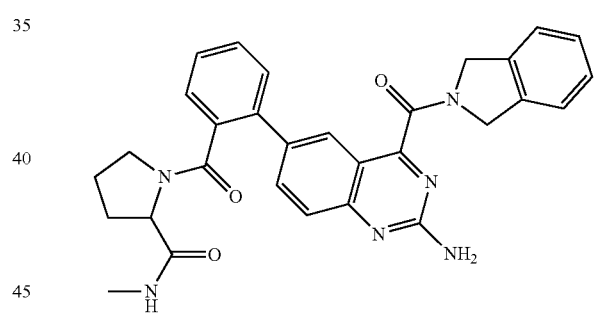

Step 1: Methyl 1-{2-[2-amino-4-(1,3-dihydroisoindole-2-carbonyl)quinazolin-6-yl]benzoyl}pyrrolidine-2-carboxylate ("A37")

The product is obtained analogously to "A34" by reaction of 2-[2-amino-4-(1,3-dihydroisoindole-2-carbonyl)quinazolin-6-yl]benzoic acid with methyl pyrrolidine-2-carboxylate;
LC-MS retention time: 1.78 min (method 1).

Step 2: 1-{2-[2-Amino-4-(1,3-dihydroisoindole-2-carbonyl)quinazolin-6-yl]-benzoyl}pyrrolidine-2-carboxylic acid ("A44")

Methyl 1-{2-[2-amino-4-(1,3-dihydroisoindole-2-carbonyl)quinazolin-6-yl]-benzoyl}pyrrolidine-2-carboxylate from step 1 is hydrolysed under alkaline conditions to give 1-{2-[2-amino-4-(1,3-dihydroisoindole-2-carbonyl)-quinazolin-6-yl]benzoyl}pyrrolidine-2-carboxylic acid;
LC-MS retention time: 1.66 min (method 1);

$^1$H NMR (500 MHz, DMSO-d$_6$) δ [ppm] 8.06 (dd, J=1.9, 8.7, 1H), 7.98 (d, J=1.9, 1H), 7.77 (d, J=8.7, 1H), 7.56-7.25 (m, 7H), 7.23 (d, J=7.4, 1H), 5.08-4.66 (m, 4H), 4.21 (dd, J=4.2, 8.5, 1H), 3.26-3.11 (m, 2H), 2.15-2.00 (m, 1H), 1.79-1.48 (m, 3H).

Step 3: 1-{2-[2-Amino-4-(1,3-dihydroisoindole-2-carbonyl)quinazolin-6-yl]-benzoyl}pyrrolidine-2-methylamide ("A50")

95 mg of TBTU (O-(benzotriazol-1-yl)-N,N,N',N'-tetramethyluronium tetrafluoroborate), 108 µl of 4-methylmorpholine and 197 µl of methylamine (2 M in THF) are added to a solution of 100 mg of 1-{2-[2-amino-4-(1,3-dihydroisoindole-2-carbonyl)quinazolin-6-yl]benzoyl}pyrrolidine-2-carboxylic acid in 4 ml of DMF. The mixture is stirred at 22° C. for 16 h, and the product is isolated directly by column chromatography;

HPLC retention time: 2.34 min (method 2).

Scheme 3: Sulfonamide Syntheses

Method C

Preparation of 2-[2-amino-4-(1,3-dihydroisoindole-2-carbonyl)quinazolin-6-yl]benzenesulfonic acid (9)

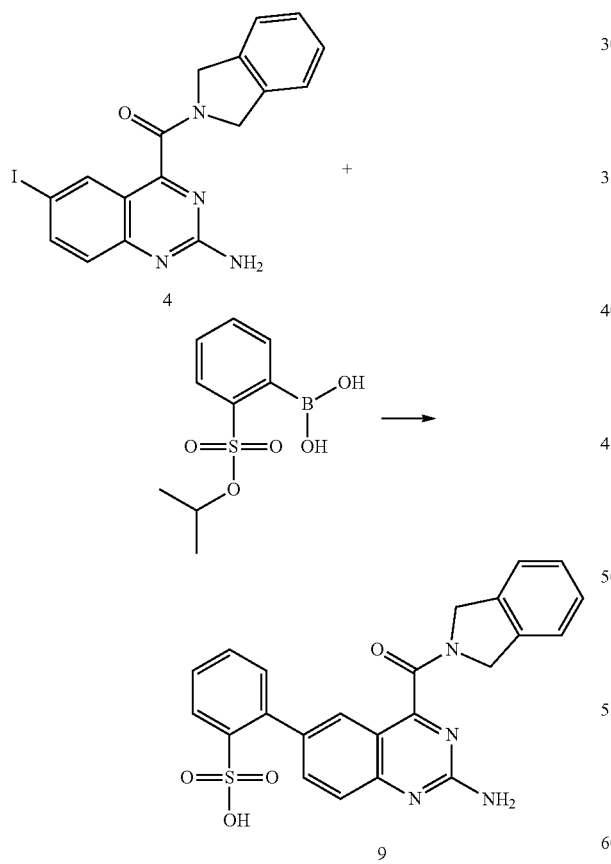

30 g of ethyl 2-(4,4,5,5-tetra methyl-1,3,2-dioxaborolan-2-yl)benzoate, 41 g of potassium carbonate, 40 ml of water and 4 g of [1,1'-bis(diphenylphosphino)ferrocene]palladium (II)dichloride are added to a solution of 40.8 g of 2-amino-6-iodo-4-(1,3-dihydroisoindol-2-ylcarbonyl)quinazoline in 500 ml of ethanol under argon. The mixture is heated at 120° C. for 60 min, giving a clear solution. The hot solution is filtered through kieselguhr and rinsed with ethanol. The filtrate is evaporated to dryness in vacuo, dissolved in 700 ml of water and filtered. The filtrate is acidified using 400 ml of HCl (1 N), giving a precipitate. The precipitate is filtered off with suction and washed with water. The residue is dried at 50° C. in vacuo. Yield: 43.8 g (86%) of 2-[2-amino-4-(1,3-dihydroisoindole-2-carbonyl)quinazolin-6-yl]benzenesulfonic acid;

LC-MS retention time: 1.43 min (method 1).

Preparation of 2-[2-amino-4-(1,3-dihydroisoindole-2-carbonyl)quinazolin-6-yl]benzenesulfonyl chloride (10)

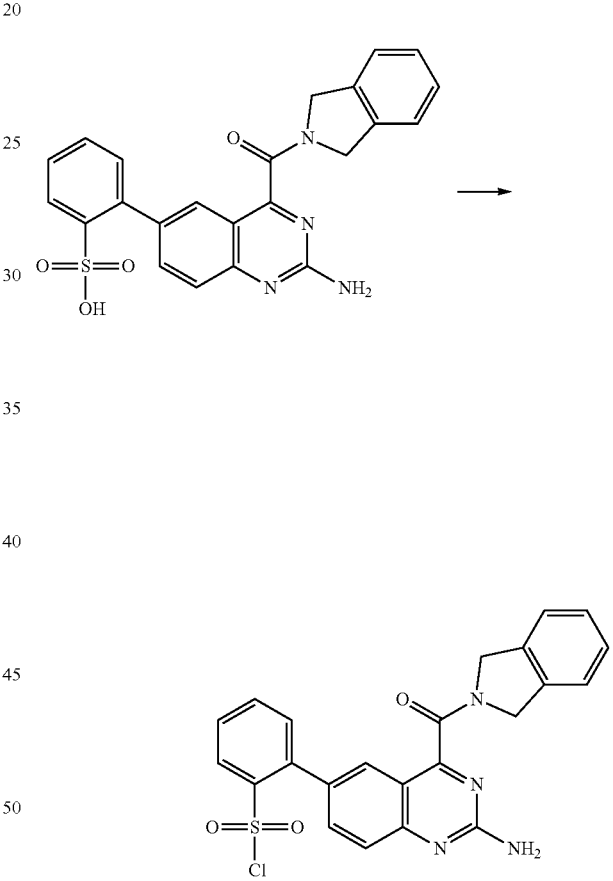

40 ml of thionyl chloride together with one drop of DMF are added to a solution of 5 g of 2-[2-amino-4-(1,3-dihydroisoindole-2-carbonyl)quinazolin-6-yl]benzenesulfonic acid. The mixture is stirred at 22° C. for 16 h, evaporated in vacuo, taken up in 500 ml of DCM and extracted twice with 300 ml of water each time. The organic phase is dried over magnesium sulfate, filtered off and evaporated to dryness in vacuo. The residue is employed in the following steps without further purification. Yield: 6.9 g (98%) of 2-[2-amino-4-(1,3-dihydroisoindole-2-carbonyl)quinazolin-6-yl]benzenesulfonyl chloride;

HPLC retention time: 2.75 min (method 2).

Preparation of {2-amino-6-[2-(2,5-dimethylpyrrolidine-1-sulfonyl)phenyl]-quinazolin-4-yl}-(1,3-dihydroisoindol-2-yl)methanone ("A64")

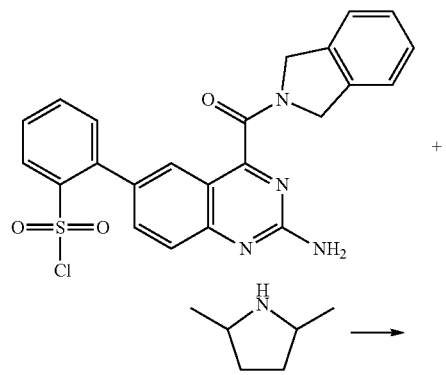

+

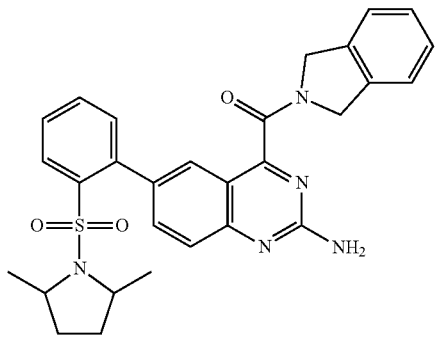

A solution of 58 µl of dimethylpyrrolidine in 4 ml of THF is added dropwise to a solution of 400 mg of 2-[2-amino-4-(1,3-dihydroisoindole-2-carbonyl)-quinazolin-6-yl]benzenesulfonyl chloride in 4 ml of THF with ice-cooling. The mixture is subsequently stirred at 22° C. for a further 1 h, evaporated in vacuo and taken up in 4 ml of diethyl ether. The solution is washed 3 times against sodium hydroxide solution (2N) and finally purified by column chromatography.

Yield: 63 mg (56%) of {2-amino-6-[2-(2,5-dimethylpyrrolidine-1-sulfonyl)-phenyl]quinazolin-4-yl}-(1,3-dihydroisoindol-2-yl)methanone;

LC-MS retention time: 2.24 min (method 1);

$^1$H NMR (500 MHz, DMSO-$d_6$/TFA) δ [ppm] 8.05 (dd, J=1.9, 8.7, 1H), 7.99 (d, J=1.8, 1H), 7.98 (dd, J=1.2, 7.9, 1H), 7.77 (d, J=8.7, 1H), 7.70 (td, J=1.3, 7.5, 1H), 7.64 (td, J=1.4, 7.7, 1H), 7.42-7.38 (m, 2H), 7.33-7.26 (m, 2H), 7.21 (d, J=7.3, 1H), 4.97 (s, 2H), 4.79 (s, 2H), 3.44-3.35 (m, 2H), 1.70-1.62 (m, 2H), 1.40-1.33 (m, 2H), 0.89 (d, J=6.4, 6H).

The following compounds are obtained analogously

| No. | Structure and/or name | HPLC retention time [min] (method) | ESI-MS m/e = MW + 1 | NMR |
|---|---|---|---|---|
| "A3" | 2-{2-Amino-4-(1,3-dihydroisoindole-2-carbonyl)quinazolin-6-yl]-N-(2-dimethylaminoethyl)benzenesulfonamide | 1.43 (1) | 517.62 | $^1$H NMR (400 MHz, DMSO-$d_6$/TFA): δ [ppm] 8.096-8.071 (m, 2H), 7.999(dd, 1H), 7.823(d, 1H), 7.743(t, 1H), 7.690(t, 1H), 7.475(dd, 1H), 7.435(d, 1H), 7.365-7.306(m, 2H), 7.264 (d, 1H), 5.001(s, 1H), 4.851(s, 2H), 3.082 (q, 4H), 2.731(s, 6H). |

-continued

| No. | Structure and/or name | HPLC retention time [min] (method) | ESI-MS m/e = MW + 1 | NMR |
|---|---|---|---|---|
| "A4" | 2-[2-Amino-4-(1,3-dihydroisoindole-2-carbonyl)quinazolin-6-yl]-N,N-dimethyl-benzenesulfonamide | 1.85 (1) | 474.55 | $^1$H NMR (400 MHz, DMSO-d$_6$/TFA): δ [ppm] 8.034 (dd, 1H), 8.007(d, 1H), 7.950(dd, 1H), 7.802(d, 1H), 7.737(t, 1H), 7.674(t, 1H), 7.437-7.422(m, 2H), 7.357-7.296(m, 2H), 7.250(d, 1H), 4.995(s, 2H), 4.820(s, 2H), 2.450(s, 6H). |
| "A5" | 2-[2-Amino-4-(1,3-dihydroisoindole-2-carbonyl)quinazolin-6-yl]-N-ethylbenzene-sulfonamide | 1.87 (1) | 474.55 | $^1$H NMR (400 MHz, DMSO-d$_6$/TFA): δ [ppm] 8.082 (dd, 1H), 8.032(d, 1H), 7.985(dd, 1H), 7.828(d, 1H), 7.698(t, 1H), 7.645(t, 1H), 7.443-7.419(m, 2H), 7.353-7.295(m, 2H), 7.255(d, 1H), 5.002(s, 2H), 4.853(s, 2H), 2.705(q, 2H), 0.867(t, 3H). |
| "A6" | 2-[2-Amino-4-(1,3-dihydroisoindole-2-carbonyl)quinazolin-6-yl]-N-methyl benzenesulfonamide | 1.77 (1) | 460.53 | $^1$H NMR (400 MHz, DMSO-d$_6$/TFA): δ [ppm] 8.093 (dd, 1H), 8.060(d, 1H), 7.964(dd, 1H), 7.830(d, 1H), 7.705(t, 1H), 7.653(t, 1H), 7.461-7.420(m, 2H), 7.355-7.297(m, 2H), 7.256(d, 1H), 5.007(s, 2H), 4.845(s, 1H), 2.351(s, 3H). |
| "A7" | {2-Amino-6-[2-(4-methyl-4-oxypiperazine-1-sulfonyl)phenyl]quinazolin-4-yl}-(1,3-dihydroisoindol-2-yl)methanone | 1.52 (1) | 545.63 | |
| "A8" | 2-[2-Amino-4-(1,3-dihydroisoindole-2-carbonyl)quinazolin-6-yl]-N-(2-hydroxy-ethyl)-N-methylbenzenesulfonamide | 2.38 (2) | 504.58 | $^1$H NMR (400 MHz, DMSO-d$_6$/TFA): δ [ppm] 8.025-8.007 (m, 2H), 7.937(d, 1H), 7.786(d, 1H), 7.668(t, 1H), 7.605(t, 1H), 7.392-7.364 (m, 2H), 7.313-7.253(m, 2H), 7.209(d, 1H), 4.969(s, 2H), 4.803(s, 2H), 3.316 (t, 2H), 2.790(t, 2H), 2.501(s, 3H). |

| No. | Structure and/or name | HPLC retention time [min] (method) | ESI-MS m/e = MW + 1 | NMR |
|---|---|---|---|---|
| "A9" | {2-Amino-6-[2-(4-hydroxypiperidine-1-sulfonyl)phenyl]quinazolin-4-yl}-(1,3-dihydroisoindol-2-yl)methanone | 2.93 (2) | 530.62 | $^1$H NMR (400 MHz, DMSO-$d_6$/TFA): δ [ppm] 7.975-7.955(m, 2H), 7.920(d, 1H), 7.747(d, 1H), 7.625(t, 1H), 7.564(t, 1H), 7.340-7.326(m, 2H), 7.270-7.209(m, 2H), 7.165(d, 1H), 5.543(s, 1H), 4.947(s, 2H), 4.786(s, 2H), 3.460-3.410(m, 1H), 2.991-2.953(m, 2H), 2.559-2.530(m, 2H), 1.539-1.488(m, 2H), 1.212-1.141(m, 2H). |
| "A11" | 2-[2-Amino-4-(1,3-dihydroisoindole-2-carbonyl)quinazolin-6-yl]-N-(2-hydroxy-ethyl)benzenesulfonamide | 1.65 (1) | 490.55 | $^1$H NMR (400 MHz, DMSO-$d_6$/TFA): δ [ppm] 8.06-8.00(m, 2H), 7.97(dd, J = 1.2, 7.9, 1H), 7.77(d, J = 8.9, 1H), 7.60(td, J = 1.3, 7.5, 1H), 7.55 (td, J = 1.4, 7.7, 1H), 7.37-7.32(m, 2H), 7.24(td, J = 6.9, 13.6, 2H), 7.17(d, J = 7.0, 1H), 4.95(s, 2H), 4.81(s, 2H), 3.24(t, J = 5.9, 2H), 2.72(t, J = 5.9, 2H). |
| "A12" | 4-{2-[2-Amino-4-(1,3-dihydroisoindole-2-carbonyl)quinazolin-6-yl]benzene-sulfonyl}piperazin-2-one | 1.62 (1) | 592.59 | $^1$H NMR (400 MHz, DMSO-$d_6$/TFA): δ [ppm] 8.02-7.98(m, 2H), 7.96(d, J = 8.7, 1H), 7.74(d, J = 8.7, 1H), 7.65(t, J = 7.5, 1H), 7.57(t, J = 7.7, 1H), 7.36(d, J = 7.6, 1H), 7.31(d, J = 7.5, 1H), 7.22(dt, J = 7.3, 15.0, 2H), 7.15(d, J = 7.2, 1H), 4.94(s, 2H), 4.80(s, 2H), 3.28(s, 2H), 2.98(s, 4H). |
| "A13" | 2-[2-Amino-4-(1,3-dihydroisoindole-2-carbonyl)quinazolin-6-yl]-N-methyl-N-(2-methylaminoethyl)benzenesulfonamide | 1.50 (1) | 517.62 | $^1$H NMR (400 MHz, DMSO-$d_6$/TFA): δ [ppm] 8.01(d, J = 1.5, 1H), 7.99(dd, J = 1.9, 8.6, 1H), 7.91(dd, J = 1.0, 7.9, 1H), 7.78(d, J = 8.6, 1H), 7.68-7.63(m, 1H), 7.60(td, J = 1.3, 7.8, 1H), 7.37(dd, J = 1.1, 7.5, 1H), 7.35(d, J = 7.2, 1H), 7.26 (dt, J = 7.1, 14.3, 2H), 7.19(d, J = 7.1, 1H), 4.95(s, 2H), 4.81(s, 2H), 3.05(t, J = 6.4, 2H), 2.93(t, J = 6.3, 2H), 2.47(s, 3H). |
| "A14" | 2-[2-Amino-4-(1,3-dihydroisoindole-2-carbonyl)quinazolin-6-yl]-N-(2-amino-ethyl)benzenesulfonamide | 1.45 (1) | 489.57 | $^1$H NMR (400 MHz, DMSO-$d_6$/TFA): δ [ppm] 8.06(dd, J = 1.9, 8.6, 1H), 8.03(d, J = 1.6, 1H), 7.97(dd, J = 1.1, 7.8, 1H), 7.79(d, J = 8.6, 1H), 7.70(td, J = 1.2, 7.5, 1H), 7.65(td, J = 1.3, 7.7, 1H), 7.44(dd, J = 1.1, 7.5, 1H), 7.40 (d, J = 7.1, 1H), 7.30(dt, J = 7.2, 14.3, 2H), 7.23(d, J = 7.1, 1H), 4.97(s, 2H), 4.83(s, 2H), 2.93(t, J = 6.5, 2H), 2.77(t, J = 6.5, 2H). |

| No. | Structure and/or name | HPLC retention time [min] (method) | ESI-MS m/e = MW + 1 | NMR |
|---|---|---|---|---|
| "A17" | 2-[2-Amino-4-(1,3-dihydroisoindole-2-carbonyl)quinazolin-6-yl]-N-(2-dimethyl-amino-1-methylethyl)benzenesulfonamide | 1.49 (1) | 531.65 | $^1$H NMR (400 MHz, DMSO-$d_6$/TFA): δ [ppm] 8.07(d, J = 7.8, 1H), 8.04(d, J = 8.7, 1H), 7.97(s, 1H), 7.80 (d, J = 8.6, 1H), 7.70(t, J = 7.4, 1H), 7.65 (t, J = 7.6, 1H), 7.39(t, J = 7.6, 2H), 7.33-7.25(m, 2H), 7.23(d, J = 7.0, 1H), 5.00-4.90(m, 2H), 4.89-4.80(m, 2H), 3.60-3.48(m, 1H), 2.95-2.83(m, 2H), 2.70(s, 6H), 0.73(d, J = 6.3, 3H). |
| "A18" | 2-[2-Amino-4-(1,3-dihydroisoindole-2-carbonyl)quinazolin-6-yl]-N-methyl-N-(3-methyl-3H-imidazol-4-ylmethyl)benzene-sulfonamide | 1.50 (1) | 554.64 | |
| "A19" | {2-Amino-6-[2-(2-methylpyrrolidine-1-sulfonyl)phenyl]quinazolin-4-yl}-(1,3-dihydroisoindol-2-yl)methanone | 2.01 (1) | 514.62 | |
| "A20" | N-(1-{2-[2-Amino-4-(1,3-dihydroisoindole-2-carbonyl)quinazolin-6-yl]benzene-sulfonyl}pyrrolidin-3-yl)acetamide | 1.69 (1) | 557.64 | |
| "A21" | {2-Amino-6-[2-(3-hydroxymethylpyrrolidine-1-sulfonyl)-phenyl]quinazolin-4-yl}-(1,3-dihydro-isoindol-2-yl)methanone | 1.71 (1) | 530.62 | |
| "A25" | 2-[2-Amino-4-(1,3-dihydroisoindole-2-carbonyl)quinazolin-6-yl]-N-ethyl-N-(2-hydroxyethyl)benzenesulfonamide | 1.74 (1) | 518.61 | $^1$H NMR (400 MHz, DMSO-$d_6$/TFA): δ [ppm] 8.06(dd, J = 1.9, 8.6, 1H), 8.03(d, J = 1.7, 1H), 7.99(dd, J = 1.2, 7.9, 1H), 7.83(d, J = 8.6, 1H), 7.71(td, J = 1.3, 7.5, 1H), 7.64(td, J = 1.3, 7.7, 1H), 7.45-7.42(m, 1H), 7.41(dd, J = 1.2, 7.5, 1H), 7.32(dt, J = 7.0, 10.8, 2H), 7.25(d, J = 7.1, 1H), 5.00(s, 2H), |

| No. | Structure and/or name | HPLC retention time [min] (method) | ESI-MS m/e = MW + 1 | NMR |
|---|---|---|---|---|
| | | | | 4.83(s, 2H), 3.29(t, J = 6.3, 2H), 2.93(q, J = 8.0, 15.1, 2H), 2.89(t, J = 6.4, 2H), 0.88(t, J = 7.1, 3H). |
| "A27" | {2-Amino-6-[2-(imidazole-1-sulfonyl)-phenyl]quinazolin-4-yl}-(1,3-dihydro-isoindol-2-yl)methanone | 1.82 (1) | 497.55 | |
| "A28" | {2-Amino-6-[2-(2-methylimidazole-1-sulfonyl)phenyl]quinazolin-4-yl}-(1,3-dihydroisoindol-2-yl)methanone | 1.79 (1) | 511.58 | |
| "A30" | {2-Amino-6-[2-(4-methylimidazole-1-sulfonyl)phenyl]quinazolin-4-yl}-(1,3-dihydroisoindol-2-yl)methanone | 1.88 (1) | 511.58 | |
| "A31" | {2-Amino-6-[2-(3-hydroxypyrrolidine-1-sulfonyl)phenyl]quinazolin-4-yl}-(1,3-dihydroisoindol-2-yl)methanone | 1.72 (1) | 516.59 | $^1$H NMR (400 MHz, DMSO-$d_6$/TFA): δ [ppm] 8.03(dd, J = 1.9, 8.6, 1H), 8.01(d, J = 1.5, 1H), 7.99 (dd, J = 1.3, 8.0, 1H), 7.77(d, J = 8.6, 1H), 7.67(td, J = 1.3, 7.5, 1H), 7.60(td, J = 1.4, 7.7, 1H), 7.40-7.35(m, 2H), 7.28(td, J = 6.7, 12.7, 2H), 7.21(t,d J = 6.8, 1H), 4.97(s, 2H), 4.79(s, 2H), 4.09-4.04(m, 1H), 3.00 (td, J = 7.0, 9.3, 1H), 2.96-2.89(m, 2H), 2.84(d, J = 10.2, 1H), 1.74-1.64(m, 1H), 1.61-1.54(m, 1H). |
| "A32" | {2-Amino-6-[2-(pyrrolidine-1-sulfonyl)-phenyl]quinazolin-4-yl}-(1,3-dihydro-isoindol-2-yl)methanone | 1.97 (1) | 500.59 | $^1$H NMR (400 MHz, DMSO-$d_6$/TFA): δ [ppm] 8.01(dd, J = 1.9, 8.6, 1H), 7.99(d, J = 1.6, 1H), 7.94(dd, J = 1.1, 7.9, 1H), 7.77(d, J = 8.6, 1H), 7.67(td, J = 1.2, 7.5, 1H), 7.60(td, J = 1.3, 7.7, 1H), 7.39-7.35(m, 2H), 7.31-7.23(m, 2H), 7.18(dd, J = 4.0, 9.7, 1H), 4.96(s, 2H), 4.78(s, 2H), 2.81(t, J = 6.7, 4H), 1.60-1.53(m, 4H). |
| "A45" | 2-[2-Amino-4-(1,3-dihydroisoindole-2-carbonyl)quinazolin-6-yl]-N,N-diethyl-benzenesulfonamide | 2.04 (1) | 502.61 | $^1$H NMR (400 MHz, DMSO-$d_6$/TFA): δ [ppm] 8.00(dd, J = 1.9, 8.6, 1H), 7.95(d, J = 1.8, 1H), 7.92(dd, J = 1.2, 7.9, 1H), 7.79(d, J = 8.6, 1H), 7.69(td, J = 1.2, 7.5, 1H), 7.61(td, J = 1.3, 7.7, 1H), 7.41(d, J = 7.2, 1H), 7.38(dd, J = 1.2, 7.6, 1H), 7.33-7.26(m, 2H), 7.21(d, J = 7.2, 1H), 4.96(s, 2H), 4.80(s, 2H), 2.83 (q, J = 7.1, 4H), 0.83(t, J = 7.1, 6H). |
| "A51" | 2-[2-Amino-4-(1,3-dihydroisoindole-2-carbonyl)quinazolin-6-yl]-N-cyclobutyl-benzenesulfonamide | 2.79 (2) | 500.59 | $^1$H NMR (400 MHz, DMSO-$d_6$/TFA): δ [ppm] 8.02(dd, J = 1.9, 8.7, 1H), 7.95-7.92(m, 2H), 7.79(d, J = 8.7, 1H), 7.64(td, J = 1.2, 7.5, 1H), 7.59(td, J = 1.2, 7.7, 1H), 7.39-7.35(m, 2H), 7.27(dt, J = 4.1, 7.4, 2H), 7.22(d, J = 6.6, 1H), 4.96(s, 2H), 4.85(s, 2H), 3.44-3.35(m, 1H), 1.85-1.77(m, 2H), 1.74-1.65(m, 2H), 1.33-1.16(m, 2H). |
| "A52" | 2-[2-Amino-4-(1,3-dihydroisoindole-2-carbonyl)quinazolin-6-yl]-N-cyclopropyl-benzenesulfonamide | 2.67 (2) | 486.57 | $^1$H NMR (400 MHz, DMSO-$d_6$/TFA): δ [ppm] 8.03-7.99(m, 2H), 7.96(d, J = 1.8, 1H), 7.78(d, J = 8.6, 1H), 7.67(td, J = 1.3, 7.5, 1H), 7.62(td, J = 1.3, 7.7, 1H), 7.39(t, J = 7.0, 2H), 7.28 (td, J = 6.9, 12.9, 2H), 7.22(d, J = 7.0, 1H), 4.96(s, 2H), 4.82(s, 2H), 2.10-2.03(m, 1H), 0.33-0.18(m, 4H). |
| "A53" | {2-Amino-6-[2-(3,3-difluoropyrrolidine-1-sulfonyl)phenyl]quinazolin-4-yl}-(1,3-dihydroisoindol-2-yl)methanone | 2.77 (2) | 536.57 | $^1$H NMR (400 MHz, DMSO-$d_6$/TFA): δ [ppm] 8.066-8.034(m, 3H), 7.822(d, 1H), 7.776(t, 1H), 7.693(t, 1H), 7.463-7.424(m, 2H), 7.356-7.295(m, 2H), 7.247(d, 1H), 4.997(s, 2H), 4.825(s, 2H), 3.319(t, 2H), 3.116(t, 2H), 2.242(m, 2H). |

-continued

| No. | Structure and/or name | HPLC retention time [min] (method) | ESI-MS m/e = MW + 1 | NMR |
|---|---|---|---|---|
| "A59" | 2-[2-Amino-4-(1,3-dihydroisoindole-2-carbonyl)quinazolin-6-yl]-N-tert-butyl-N-methylbenzenesulfonamide | 2.83 (2) | 516.64 | $^1$H NMR (400 MHz, DMSO-$d_6$/TFA): δ [ppm] 8.02(dd, J = 1.9, 8.6, 1H), 7.98 (dd, J = 1.3, 7.0, 2H), 7.81(d, J = 8.6, 1H), 7.64(td, J = 1.3, 7.5, 1H), 7.58(td, J = 1.4, 7.8, 1H), 7.38(d, J = 7.3, 1H), 7.33(dd, J = 1.2, 7.5, 1H), 7.32-7.24(m, 2H), 7.20(d, J = 7.2, 1H), 4.96(s, 2H), 4.84(s, 2H), 2.19(s, 3H), 1.06(s, 9H). |
| "A60" | {2-Amino-6-[2-(3,3-difluoroazetidine-1-sulfonyl)phenyl]quinazolin-4-yl}-(1,3-dihydroisoindol-2-yl)methanone | 2.77 (2) | 522.55 | $^1$H NMR (400 MHz, DMSO-$d_6$/TFA): δ [ppm] 8.09-8.03(m, 3H), 7.82-7.76(m, 2H), 7.68(ddd, J = 1.2, 6.1, 8.8, 1H), 7.46(dd, J = 1.0, 7.6, 1H), 7.40(d, J = 7.3, 1H), 7.33-7.26(m, 2H), 7.21(d, J = 7.3, 1H), 4.96(d, J = 9.2, 2H), 4.81-4.76(m, 2H), 4.05(t, J = 12.6, 4H). |
| "A64" | {2-Amino-6-[2-(2,5-dimethylpyrrolidine-1-sulfonyl)phenyl]quinazolin-4-yl}-(1,3-dihydroisoindol-2-yl)methanone | 2.24 (1) | 528.65 | $^1$H NMR (400 MHz, DMSO-$d_6$/TFA): δ [ppm] 8.05(dd, J = 1.9, 8.7, 1H), 7.99 (d, J = 1.8, 1H), 7.98(dd, J = 1.2, 7.9, 1H), 7.77(d, J = 8.7, 1H), 7.70(td, J = 1.3, 7.5, 1H), 7.64(td, J = 1.4, 7.7, 1H), 7.42-7.38(m, 2H), 7.33-7.26(m, 2H), 7.21(d, J = 7.3, 1H), 4.97(s, 2H), 4.79(s, 2H), 3.44-3.35 (m, 2H), 1.70-1.62(m, 2H), 1.40-1.33 (m, 2H), 0.89(d, J = 6.4, 6H). |
| "A65" | 2-[2-Amino-4-(1,3-dihydroisoindole-2-carbonyl)quinazolin-6-yl]-N-cyclopropyl-N-methylbenzenesulfonamide | | | |
| "A66" | {2-Amino-6-[2-((R)-2-methylpyrrolidine-1-sulfonyl)phenyl]quinazolin-4-yl}-(1,3-dihydroisoindol-2-yl)methanone | 2.16 (1) | 514.62 | $^1$H NMR (400 MHz, DMSO-$d_6$/TFA): δ [ppm] 8.06(dd, J = 1.9, 8.7, 1H), 8.00(d, J = 1.7, 1H), 7.98(dd, J = 1.1, 7.9, 1H), 7.79(dd, J = 5.2, 9.4, 1H), 7.72(td, J = 1.3, 7.5, 1H), 7.66(td, J = 1.3, 7.7, 1H), 7.45-7.40(m, 2H), 7.37-7.28(m, 2H), 7.24(d, J = 7.2, 1H), 4.99(s, 2H), 4.81(s, 2H), 3.54-3.42(m, 1H), 2.93-2.85(m, 1H), 2.85-2.78(m, 1H), 1.81-1.71 (m, 1H), 1.71-1.60(m, 1H), 1.56-1.47(m, 1H), 1.37-1.29(m, 1H), 0.85(d, J = 6.4, 3H). |
| "A67" | {2-Amino-6-[2-((S)-3-fluoropyrrolidine-1-sulfonyl)phenyl]quinazolin-4-yl}-(1,3-dihydroisoindol-2-yl)methanone | 2.51 (2) | 518.58 | $^1$H NMR (400 MHz, DMSO-$d_6$/TFA): δ [ppm] 8.04(dd, J = 1.9, 8.6, 1H), 8.02-7.99(m, 2H), 7.80(d, J = 8.6, 1H), 7.74(t, J = 7.6, 1H), 7.67(t, J = 7.7, 1H), 7.43(d, J = 7.4, 2H), 7.32(dt, J = 7.4, 15.8, 2H), 7.25(d, J = 7.3, 1H), 4.99(s, 2H), 4.82 (s, 2H), 3.24-2.96(m, 5H), 1.98-1.82(m, 2H). |

-continued

| No. | Structure and/or name | HPLC retention time [min] (method) | ESI-MS m/e = MW + 1 | NMR |
|---|---|---|---|---|
| "A68" | 2-[2-Amino-4-(1,3-dihydroisoindole-2-carbonyl)quinazolin-6-yl]-N-azetidin-3-yl-N-methylbenzenesulfonamide | 2.12 (2) | 515.61 | |
| "A82" | 2-[2-Amino-4-(1,3-dihydroisoindole-2-carbonyl)quinazolin-6-yl]-N-ethyl-4-fluoro-N-(2-hydroxyethyl)benzenesulfonamide | 1.94 (1) | 536.60 | $^1$H NMR (400 MHz, DMSO-d$_6$/TFA): δ [ppm] 8.09-8.02(m, 3H), 7.82(d, J = 9.4, 1H), 7.49-7.41(m, 2H), 7.31(ddd, J = 5.0, 11.7, 12.2, 3H), 7.24(d, J = 7.2, 1H), 5.00(s, 2H), 4.82(s, 2H), 3.29(t, J = 6.2, 2H), 3.13(q, J = 7.3, 2H), 1.21(t, J = 7.3, 3H), 0.87(t, J = 7.1, 3H). |

Method D

Preparation of 2-[2-amino-4-(1,3-dihydroisoindole-2-carbonyl)quinazolin-6-yl]-N-cyclopropyl-N-methylbenzenesulfonamide ("A65")

Step 1:
2-Bromo-N-cyclopropyl-N-methylbenzenesulfonamide

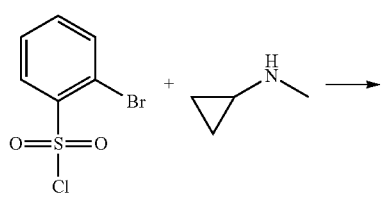

-continued

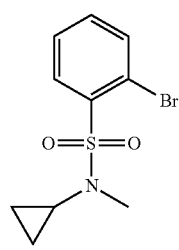

450 µl of N-cyclopropyl-N-methylamine are added dropwise with cooling to a solution of 640 mg of 2-bromobenzenesulfonyl chloride in 2.5 ml of DCM. The mixture is subsequently stirred at 22° C. for 2 h, extracted twice with 5 ml of 1N sodium hydroxide solution, the organic phase is dried over magnesium sulfate, filtered and evaporated in vacuo.

Yield: 670 mg (96%) of 2-bromo-N-cyclopropyl-N-methylbenzene-sulfonamide;

HPLC retention time: 2.70 min (method 2).

Step 2: "A65"

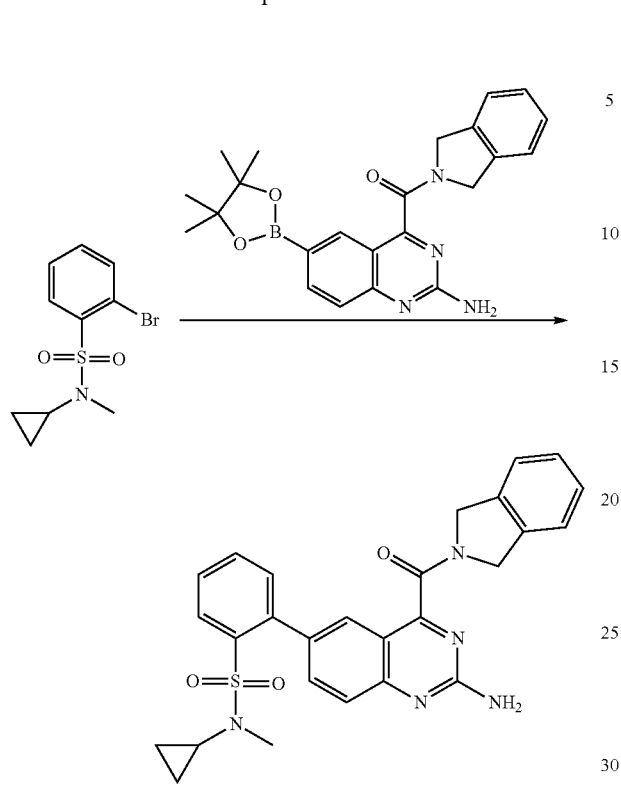

153 mg of 2-bromo-N-cyclopropyl-N-methylbenzenesulfonamide, 0.146 g of potassium carbonate, 9 μl of water and 43 mg of [1,1'-bis(diphenylphosphino)ferrocene]palladium(II)dichloride are added to a solution of 220 mg of {2-amino-5-[(Z)-2-(4,4,5,5-tetramethyl-1,3,2-dioxaborolan-2-yl)propenyl]-6-vinylpyrimidin-4-yl}-(1,3-dihydroisoindol-2-yl)methanone in 5 ml of ethanol under argon. The mixture is heated at 120° C. for 30 min. The hot mixture is subsequently filtered through kieselguhr, the filtrate is evaporated in vacuo, taken up in 1 ml of DMSO and purified by column chromatography.

Yield: 61 mg (23%) of 2-[2-amino-4-(1,3-dihydroisoindole-2-carbonyl)-quinazolin-6-yl]-N-cyclopropyl-N-methylbenzenesulfonamide ("A65");

LC-MS retention time: 2.61 min (method 1);

$^1$H NMR (500 MHz, DMSO-$d_6$/TFA) δ [ppm] 8.02 (dd, J=1.2, 7.9, 1H), 7.97 (dd, J=1.9, 8.6, 1H), 7.91 (d, J=1.8, 1H), 7.77 (d, J=8.7, 1H), 7.73 (dd, J=1.3, 7.5, 1H), 7.68 (td, J=1.4, 7.7, 1H), 7.42 (d, J=7.2, 1H), 7.40 (dd, J=1.2, 7.5, 1H), 7.35-7.27 (m, 2H), 7.23 (d, J=7.1, 1H), 4.97 (s, 2H), 4.80 (s, 2H), 2.35 (s, 3H), 2.05 (tt, J=3.6, 6.8, 1H), 0.46-0.34 (m, 2H), 0.34-0.26 (m, 2H).

The preparation of 2-[2-amino-4-(1,3-dihydroisoindole-2-carbonyl)quinazolin-6-yl]-N-tert-butylbenzenesulfonamide ("A1") is carried out analogously to the following scheme

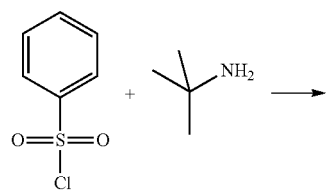

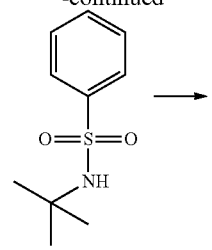

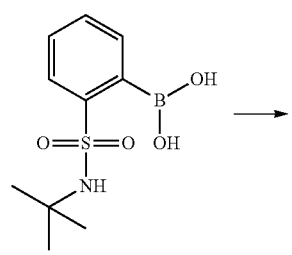

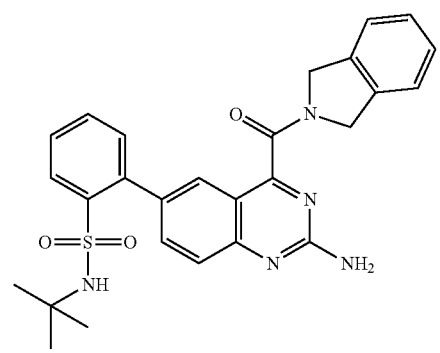

Step 1: Preparation of N-tert-butylbenzenesulfonamide

The synthesis is carried out analogously to the preparation of 2-bromo-N-cyclopropyl-N-methylbenzenesulfonamide; m.p. 77-78° C.

Step 2: 2-Borono-N-tert-butylbenzenesulfonamide 27 ml of n-butyllithium (15% solution in n-hexane) are added dropwise at −5° C. to a solution of 4.29 g of N-tert-butylbenzenesulfonamide in 25 ml of THF under argon. The mixture is stirred at 22° C. for 1 h, re-cooled to −5° C., and 2.8 g of trimethyl borate are slowly added dropwise. The mixture is stirred at 22° C. for 3 h, before 100 ml of aqueous ammonium chloride solution is added dropwise. The phases are separated, and the aqueous phase is extracted a further twice with MTB ether. The combined organic phases are dried over magnesium sulfate. Filtered and evaporated to dryness in vacuo.

Yield: 42% of 2-borono-N-tert-butylbenzenesulfonamide; HPLC retention time: 2.42 min (method 2).

Step 3: 2-[2-Amino-4-(1,3-dihydroisoindole-2-carbonyl)quinazolin-6-yl]-N-tert-butylbenzenesulfonamide ("A1")

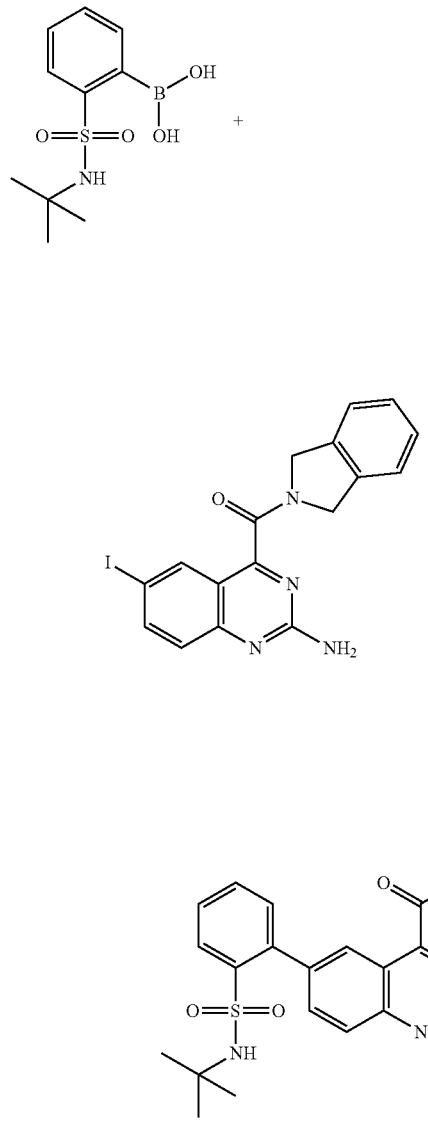

1.6 g of 2-borono-N-tert-butylbenzenesulfonamide, 2.66 g of potassium carbonate, 86 μl of water and 196 mg of [1,1'-bis(diphenylphosphino)ferrocene]palladium(II)dichloride are added to a solution of 2 g of 2-amino-6-iodo-4-(1,3-dihydroisoindol-2-ylcarbonyl)quinazoline in 100 ml of ethanol under argon. The mixture is heated at 120° C. for 16 h, giving a clear solution. The hot solution is filtered through kieselguhr and rinsed with ethanol. The filtrate is evaporated to dryness in vacuo. Crystallisation of the residue from 5 ml of acetonitrile/water gives the product.

Yield: 2.3 g (95%) of 2-[2-amino-4-(1,3-dihydroisoindole-2-carbonyl)quinazolin-6-yl]-N-tert-butylbenzenesulfonamide ("A1");

LC-MS retention time: 2.04 min (method 1);

$^1$H NMR (500 MHz, DMSO-$d_6$/TFA) δ [ppm] 8.082 (dd, 1H), 8.032 (d, 1H), 7.985 (dd, 1H), 7.828 (d, 1H), 7.698 (t, 1H), 7.645 (t, 1H), 7.443-7.419 (m, 2H), 7.353-7.295 (m, 2H), 7.255 (d, 1H), 5.002 (s, 2H), 4.853 (s, 2H), 0.867 (s, 9H).

Preparation of 2-[2-amino-4-(1,3-dihydroisoindole-2-carbonyl)quinazolin-6-yl]-benzenesulfonamide ("A2")

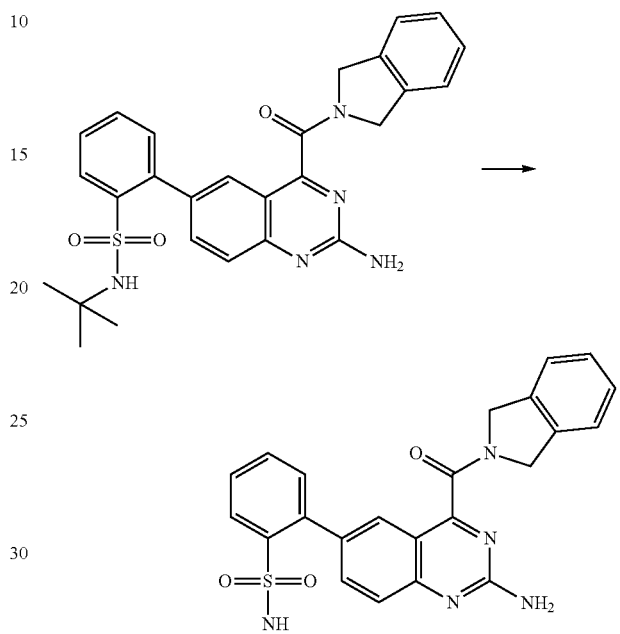

1 g of 2-[2-amino-4-(1,3-dihydroisoindole-2-carbonyl)quinazolin-6-yl]-N-tert-butylbenzenesulfonamide is dissolved in 10 ml of trifluoroacetic acid and stirred at 22° C. for 16 h. 10 ml of n-heptane are subsequently added and evaporated to dryness in vacuo. The crude product obtained in this way is purified by column chromatography.

Yield: 2.3 g (95%) of 2-[2-amino-4-(1,3-dihydroisoindole-2-carbonyl)quinazolin-6-yl]benzenesulfonamide;

LC-MS retention time: 1.64 min (method 1);

$^1$H NMR (500 MHz, DMSO-$d_6$/TFA) δ [ppm] 8.109-8.065 (m, 3H), 7.823 (d, 1H), 7.638-7.562 (m, 2H), 7.400-7.368 (m, 2H), 7.326-7.261 (m, 2H), 7.214 (d, 1H), 5.002 (s, 2H), 4.846 (s, 2H).

Preparation of 2-[2-amino-4-(1,3-dihydroisoindole-2-carbonyl)quinazolin-6-yl]-N-(2-methylaminoethyl)benzenesulfonamide ("A16")

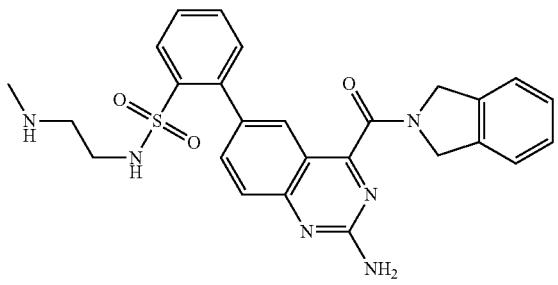 [SMILES: CNCCNS(=O)(=O)c1ccccc1-c1ccc2nc(N)nc(C(=O)N3Cc4ccccc4C3)c2c1]

The product is obtained analogously to the preparation of "A64" by reaction of 2-[2-amino-4-(1,3-dihydroisoindole-2-carbonyl)quinazolin-6-yl]benzenesulfonyl chloride and tert-butyl (2-aminoethyl)methylcarbamate. The resultant tert-butyl (2-{2-[2-amino-4-(1,3-dihydroisoindole-2-carbonyl)quinazolin-6-yl]benzenesulfonylamino}ethyl)methylcarbamate is treated directly with 1 M HCl in dioxane, causing the protecting group to be cleaved. The purification is carried out by means of preparative column chromatography.

Yield: 37%; LC-MS retention time: 1.42 min (method 1);

$^1$H NMR (500 MHz, DMSO-d$_6$/TFA) δ [ppm] 8.10-8.02 (m, 2H), 7.97 (dd, J=1.0, 7.9, 1H), 7.81-7.77 (m, 1H), 7.68 (dt, J=3.8, 7.6, 1H), 7.63 (td, J=1.2, 7.7, 1H), 7.42 (d, J=7.4, 1H), 7.38 (d, J=7.0, 1H), 7.33-7.24 (m, 2H), 7.22 (d, J=7.1, 1H), 4.97 (s, 2H), 4.83 (s, 2H), 2.97 (t, J=6.2, 2H), 2.86 (t, J=6.3, 2H), 2.47 (s, 3H).

The following compounds are obtained analogously

2-[2-amino-4-(1,3-dihydroisoindole-2-carbonyl)quinazolin-6-yl]-N-azetidin-3-ylbenzenesulfonamide ("A26");

LC-MS retention time: 1.43 min (method 1);

$^1$H NMR (500 MHz, DMSO-d$_6$/TFA) δ [ppm] 8.10-8.04 (m, 2H), 7.98 (dd, J=1.1, 7.9, 1H), 7.84 (d, J=8.4, 1H), 7.74 (td, J=1.2, 7.5, 1H), 7.67 (td, J=1.3, 7.8, 1H), 7.46 (dd, J=1.2, 7.6, 1H), 7.44 (d, J=7.2, 1H), 7.37-7.30 (m, 2H), 7.27 (d, J=7.0, 1H), 5.01 (s, 2H), 4.86 (s, 2H), 4.08-3.94 (m, 3H), 3.89-3.80 (m, 2H);

{2-amino-6-[2-(3-aminoazetidine-1-sulfonyl)phenyl]quinazolin-4-yl}-(1,3-dihydroisoindol-2-yl)methanone ("A29");

LC-MS retention time: 1.40 min (method 1);

$^1$H NMR (500 MHz, DMSO-d$_6$/TFA) δ [ppm] 8.11 (d, J=1.8, 1H), 8.05-8.00 (m, 2H), 7.79 (d, J=8.6, 1H), 7.72 (td, J=1.3, 7.6, 1H), 7.63 (td, J=1.3, 7.8, 1H), 7.42-7.37 (m, 2H), 7.33-7.25 (m, 2H), 7.22 (d, J=7.1, 1H), 4.99 (s, 2H), 4.81 (s, 2H), 4.00-3.92 (m, 1H), 3.80-3.76 (m, 2H), 3.73-3.68 (m, 2H);

{2-amino-6-[2-(3-aminopyrrolidine-1-sulfonyl)phenyl]quinazolin-4-yl}-(1,3-dihydroisoindol-2-yl)methanone ("A33");

LC-MS retention time: 1.48 min (method 1);

$^1$H NMR (500 MHz, DMSO-d$_6$/TFA) δ [ppm] 8.05-8.01 (m, 2H), 7.99 (dd, J=1.3, 7.9, 1H), 7.80-7.77 (m, 1H), 7.72 (td, J=1.4, 7.5, 1H), 7.65 (td, J=1.4, 7.7, 1H), 7.44-7.37 (m, 2H), 7.35-7.25 (m, 2H), 7.23 (d, J=6.7, 1H), 4.97 (s, 2H), 4.80 (s, 2H), 3.52-3.43 (m, 3H), 3.04-2.95 (m, 1H), 2.91-2.81 (m, 1H), 2.10-2.00 (m, 1H), 1.84-1.71 (m, 1H).

Preparation of 1-{2-[2-amino-4-(1,3-dihydroisoindole-2-carbonyl)quinazolin-6-yl]benzenesulfonyl}pyrrolidine-2-methylamide ("A58")

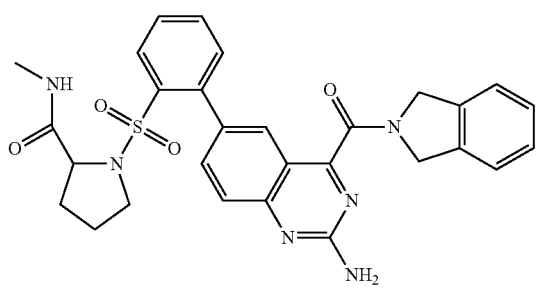 [SMILES: CNC(=O)C1CCCN1S(=O)(=O)c1ccccc1-c1ccc2nc(N)nc(C(=O)N3Cc4ccccc4C3)c2c1]

Step 1: Methyl 1-{2-[2-amino-4-(1,3-dihydroisoindole-2-carbonyl)quinazolin-6-yl]benzenesulfonyl}pyrrolidine-2-carboxylate The product is obtained analogously to "A64" by reaction of 2-[2-amino-4-(1,3-dihydroisoindole-2-carbonyl)quinazolin-6-yl]benzenesulfonyl chloride and methylpyrrolidine-2-carboxylate;

HPLC retention time: 2.65 min (method 2).

Step 2: 1-{2-[2-Amino-4-(1,3-dihydroisoindole-2-carbonyl)quinazolin-6-yl]-benzenesulfonyl}pyrrolidine-2-carboxylic acid Methyl 1-{2-[2-amino-4-(1,3-dihydroisoindole-2-carbonyl)quinazolin-6-yl]-benzenesulfonyl}pyrrolidine-2-carboxylate from step 1 is hydrolysed under alkaline conditions to give 1-{2-[2-amino-4-(1,3-dihydroisoindole-2-carbonyl)quinazolin-6-yl]benzenesulfonyl}pyrrolidine-2-carboxylic acid;

HPLC retention time: 2.45 min (method 2).

Step 3: 1-{2-[2-Amino-4-(1,3-dihydroisoindole-2-carbonyl)quinazolin-6-yl]-benzenesulfonyl}pyrrolidine-2-methylamide ("A58")

88.6 mg of TBTU (O-(benzotriazol-1-yl)-N,N,N',N'-tetramethyluronium tetrafluoroborate), 101 µl of 4-methylmorpholine and 184 µl of methylamine (2 M in THF) are added to a solution of 100 mg of 1-{2-[2-amino-4-(1,3-dihydroisoindole-2-carbonyl)quinazolin-6-yl]benzenesulfonyl}pyrrolidine-2-carboxylic acid in 4 ml of DMF. The mixture is stirred at 22° C. for 16 h, and the product is isolated directly by column chromatography.

HPLC retention time: 2.36 min (method 2);

$^1$H NMR (500 MHz, DMSO-d$_6$/TFA) δ [ppm] 8.11-8.06 (m, 2H), 8.01 (dd, J=1.1, 7.9, 1H), 7.77 (d, J=9.1, 1H), 7.67 (td, J=1.2, 7.5, 1H), 7.59 (td, J=1.3, 7.8, 1H), 7.38 (d, J=7.1, 1H), 7.35 (dd, J=1.1, 7.5, 1H), 7.28 (dt, J=7.2, 14.7, 2H), 7.20 (d, J=7.1, 1H), 4.97 (s, 2H), 4.79 (s, 2H), 3.74 (dd, J=3.8, 8.4, 1H), 3.01-2.92 (m, 2H), 2.36 (s, 3H), 1.88-1.79 (m, 1H), 1.73-1.65 (m, 1H), 1.64-1.57 (m, 1H), 1.57-1.48 (m, 1H).

The compound

N-(2-hydroxyethyl)-1-{2-[2-amino-4-(1,3-dihydroisoindole-2-carbonyl)quinazolin-6-yl]benzenesulfonyl}pyrrolidine-2-carboxamide ("A61")

is obtained analogously

HPLC retention time: 2.32 min (method 2);

$^1$H NMR (500 MHz, DMSO-d$_6$/TFA) δ [ppm] 8.11-8.06 (m, 2H), 8.01 (dd, J=1.1, 7.9, 1H), 7.77 (d, J=9.1, 1H), 7.67 (td, J=1.2, 7.5, 1H), 7.59 (td, J=1.3, 7.8, 1H), 7.38 (d, J=7.1, 1H), 7.35 (dd, J=1.1, 7.5, 1H), 7.28 (dt, J=7.2, 14.7, 2H), 7.20 (d, J=7.1, 1H), 4.97 (s, 2H), 4.79 (s, 2H), 3.74 (dd, J=3.8, 8.4, 1H), 3.01-2.92 (m, 2H), 2.36 (s, 3H), 1.88-1.79 (m, 1H), 1.73-1.65 (m, 1H), 1.64-1.57 (m, 1H), 1.57-1.48 (m, 1H).

Preparation of 2-({2-[2-amino-4-(1,3-dihydroisoindole-2-carbonyl)quinazolin-6-yl]benzenesulfonyl}methylamino)ethyl aminoacetate ("A15")

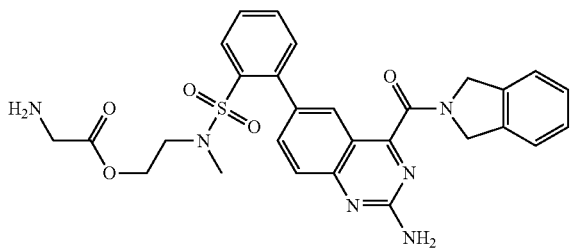 [SMILES: CN(CCOC(=O)CN)S(=O)(=O)c1ccccc1-c1ccc2nc(N)nc(C(=O)N3Cc4ccccc4C3)c2c1]

56 mg of tert-butoxycarbonylaminoacetic acid, 33 mg of N,N'-dicyclohexylcarbodiimide and 2 mg of dimethylaminopyridine (DMAP) are added to a solution of 80 mg of 2-[2-amino-4-(1,3-dihydroisoindole-2-carbonyl)quinazolin-6-yl]-N-(2-hydroxyethyl)-N-methylbenzenesulfonamide in 1 ml of THF. After 120 min, the mixture is evaporated in vacuo, the residue is taken up in 1 ml of DCM:TFA (1:1) with cooling, and the mixture is stirred for 30 min. The mixture is evaporated to dryness in vacuo, the residue is taken up in 500 µl of DMSO and purified by column chromatography on a reversed phase.

LC-MS retention time: 1.49 min (method 1);

$^1$H NMR (500 MHz, DMSOd$_6$) δ [ppm] 8.05-8.01 (m, 2H), 7.99 (dd, J=1.2, 7.9, 1H), 7.84 (d, J=4.6, 1H), 7.74 (td, J=1.3, 7.5, 1H), 7.67 (td, J=1.4, 7.8, 1H), 7.46-7.41 (m, 2H), 7.33 (dt, J=7.0, 14.0, 2H), 7.26 (d, J=7.0, 1H), 5.01 (s, 2H), 4.87 (s, 2H), 4.17 (t, J=5.2, 2H), 3.74 (s, 2H), 3.03 (t, J=5.2, 2H).

Preparation of 1-{2-[2-amino-4-(1,3-dihydroisoindole-2-carbonyl)quinazolin-6-yl]benzenesulfonyl}piperidin-4-yl aminoacetate ("A10")

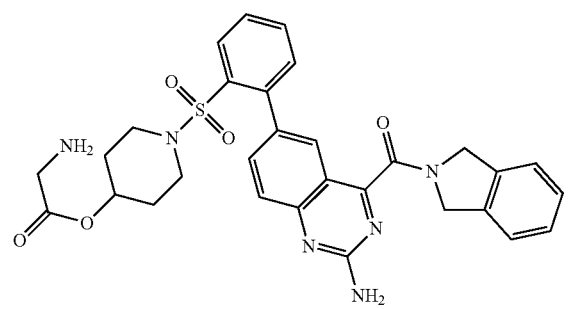 [SMILES: NCC(=O)OC1CCN(S(=O)(=O)c2ccccc2-c2ccc3nc(N)nc(C(=O)N4Cc5ccccc5C4)c3c2)CC1]

LC-MS retention time: 1.54 min (method 1);

$^1$H NMR (400 MHz, DMSO-d$_6$/TFA) δ [ppm] 8.04 (dd, J=1.9, 8.6, 1H), 8.02-7.98 (m, 2H), 7.80 (d, J=8.7, 1H), 7.75 (td, J=1.3, 7.5, 1H), 7.68 (td, J=1.4, 7.7, 1H), 7.46-7.41 (m, 2H), 7.38-7.29 (m, 2H), 7.26 (d, J=6.7, 1H), 5.00 (s, 2H), 4.88 (s, 3H), 3.82 (s, 2H), 3.13-3.01 (m, 2H), 2.86-2.76 (m, 2H), 1.74-1.62 (m, 2H), 1.56-1.42 (m, 2H).

The following compounds are obtained analogously to the preparation of "A65", step 1

1-(2-bromo-4,5-difluorobenzenesulfonyl)-4-methylpiperazine

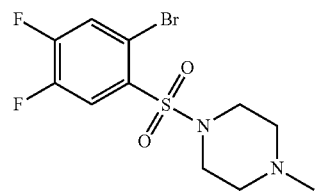 [SMILES: CN1CCN(S(=O)(=O)c2cc(F)c(F)cc2Br)CC1]

HPLC retention time: 1.35 min (method 1);

4-(2-bromo-4,5-difluorobenzenesulfonyl)-1,2-dimethylpiperazine

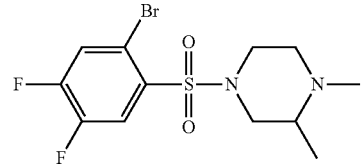 [SMILES: CC1CN(S(=O)(=O)c2cc(F)c(F)cc2Br)CCN1C]

HPLC retention time: 1.41 min (method 1);

1-(2-bromo-4,5-difluorobenzenesulfonyl)piperidin-4-ol

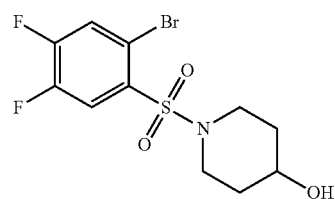 [SMILES: O=S(=O)(c1cc(F)c(F)cc1Br)N1CCC(O)CC1]

HPLC retention time: 1.89 min (method 1);

tert-butyl 4-(2-bromo-4,5-difluorobenzenesulfonyl)piperazine-1-carboxylate

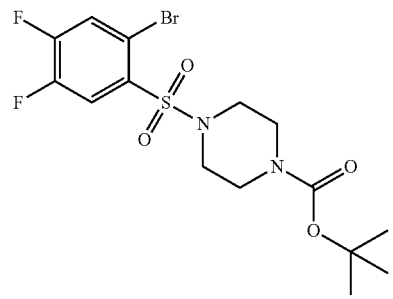 [SMILES: CC(C)(C)OC(=O)N1CCN(S(=O)(=O)c2cc(F)c(F)cc2Br)CC1]

HPLC retention time: 2.24 min (method 1);

87

2-bromo-N-ethyl-4,5-difluoro-N-(2-hydroxyethyl)benzenesulfonamide

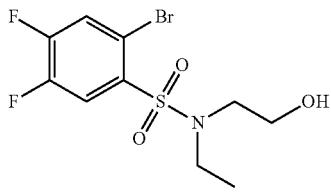 [SMILES: CCN(CCO)S(=O)(=O)c1cc(F)c(F)cc1Br]

HPLC retention time: 1.95 min (method 1);

1-(2-bromo-4,5-difluorobenzenesulfonyl)pyrrolidine

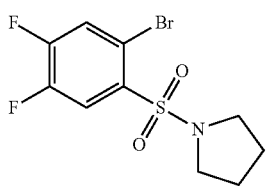 [SMILES: O=S(=O)(c1cc(F)c(F)cc1Br)N1CCCC1]

HPLC retention time: 2.28 min (method 1);

2-bromo-N-tert-butyl-4,5-difluoro-N-methylbenzenesulfonamide

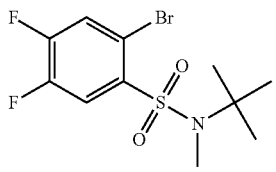 [SMILES: CN(C(C)(C)C)S(=O)(=O)c1cc(F)c(F)cc1Br]

HPLC retention time: 2.49 min (method 1);

1-(2-bromo-4,5-difluorobenzenesulfonyl)-3,3-difluoropyrrolidine

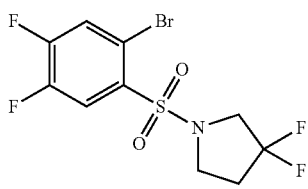 [SMILES: O=S(=O)(c1cc(F)c(F)cc1Br)N1CCC(F)(F)C1]

HPLC retention time: 2.33 min (method 1);

88

1-(2-bromo-4,5-difluorobenzenesulfonyl)pyrrolidin-3-ol

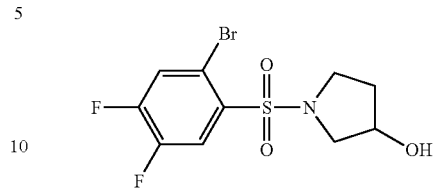

HPLC retention time: 1.83 min (method 1);

1-(2-bromo-4,5-difluorobenzenesulfonyl)-3-methylpiperazine

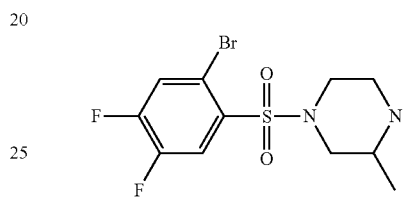

HPLC retention time: 1.34 min (method 1);

1-(2-bromo-4,5-difluorobenzenesulfonyl)-3-trifluoromethylpiperazine

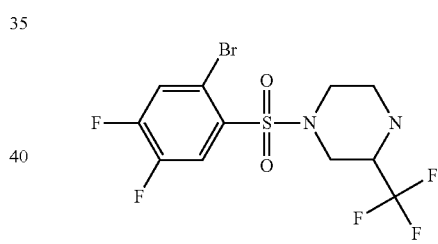

HPLC retention time: 2.17 min (method 1);

1-(2-bromo-4,5-difluorobenzenesulfonyl)-3,5-dimethylpiperazine

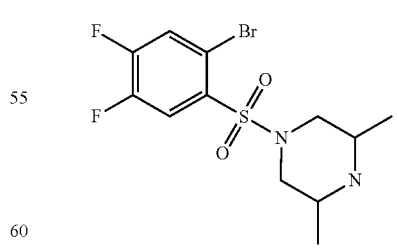

HPLC retention time: 1.44 min (method 1);
$^1$H NMR (400 MHz, DMSO-$d_6$/TFA-$d_1$) δ [ppm] 8.09 (dd, J=10.2, 8.1, 1H), 8.03 (dd, J=9.6, 7.0, 1H), 3.90 (dt, J=11.3, 5.6, 2H), 3.47-3.30 (m, 2H), 2.92 (dd, J=13.6, 11.6, 2H), 1.26 (d, J=6.4, 6H).

The following compounds are obtained analogously to the preparation of "A65", step 2

{2-amino-6-[4,5-difluoro-2-(4-methylpiperazine-1-sulfonyl)phenyl]quinazolin-4-yl}-(1,3-dihydroisoindol-2-yl)methanone ("A91")

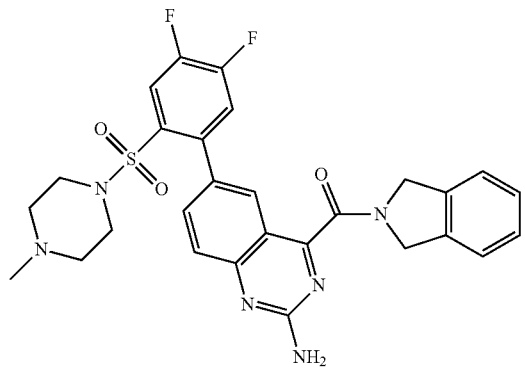 [SMILES: CN1CCN(S(=O)(=O)c2cc(F)c(F)cc2-c2ccc3nc(N)nc(C(=O)N4Cc5ccccc5C4)c3c2)CC1]

HPLC retention time: 1.68 min (method 1);
$^1$H NMR (500 MHz, DMSO-d$_6$/TFA-d$_1$) δ [ppm] 8.10 (dd, J=10.1, 7.9, 1H), 8.04 (d, J=1.5, 1H), 8.02 (dd, J=8.6, 1.8, 1H), 7.80 (d, J=8.6, 1H), 7.66 (dd, J=10.5, 7.5, 1H), 7.45 (d, J=7.2, 1H), 7.38-7.30 (m, 2H), 7.27 (d, J=7.2, 1H), 5.03 (d, J=18.0, 2H), 4.82 (d, J=18.2, 2H), 3.34 (m, 4H), 2.86 (m, 4H), 2.82 (s, 3H);

{2-amino-6-[2-(3,4-dimethylpiperazine-1-sulfonyl)-4,5-difluorophenyl]quinazolin-4-yl}-(1,3-dihydroisoindol-2-yl)methanone ("A92")

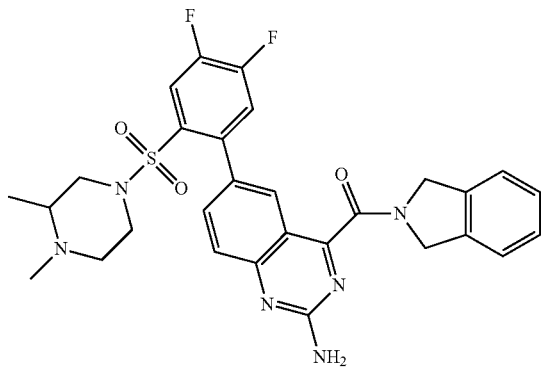 [SMILES: CC1CN(S(=O)(=O)c2cc(F)c(F)cc2-c2ccc3nc(N)nc(C(=O)N4Cc5ccccc5C4)c3c2)CCN1C]

HPLC retention time: 1.74 min (method 1);
$^1$H NMR (500 MHz, DMSO-d$_6$/TFA-d$_1$) δ [ppm] 8.12-8.06 (m, 2H), 8.04 (d, J=8.6, 1H), 7.84 (d, J=8.8, 1H), 7.61 (dd, J=10.4, 7.6, 1H), 7.44 (d, J=7.3, 1H), 7.38-7.30 (m, 2H), 7.27 (d, J=7.2, 1H), 5.03 (s, 2H), 4.87 (s, 2H), 3.46-3.30 (m, 2H), 3.20 (s, 2H), 3.06-2.89 (m, 1H), 2.85 (s, 3H), 2.76-2.65 (m, 2H), 1.21 (d, J=6.2, 3H);

{2-amino-6-[4,5-difluoro-2-(4-hydroxypiperidine-1-sulfonyl)phenyl]quinazolin-4-yl}-(1,3-dihydroisoindol-2-yl)methanone ("A93")

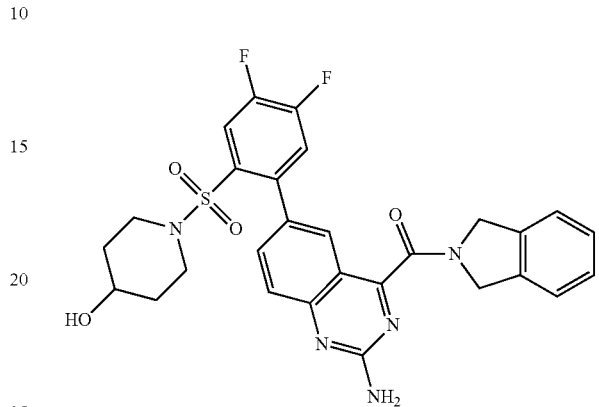

HPLC retention time: 1.97 min (method 1);
$^1$H NMR (500 MHz, DMSO-d$_6$/TFA-d$_1$) δ [ppm] 8.03 (td, J=4.6, 1.9, 2H), 7.99 (dd, J=10.3, 7.9, 1H), 7.83-7.78 (m, 1H), 7.58 (dd, J=10.6, 7.5, 1H), 7.44 (d, J=7.2, 1H), 7.38-7.28 (m, 2H), 7.26 (d, J=7.3, 1H), 5.00 (s, 2H), 4.83 (s, 2H), 3.52-3.43 (m, 1H), 3.09-3.00 (m, 2H), 2.61 (m, 2H), 1.61-1.52 (m, 2H), 1.27-1.16 (m, 2H);

{2-amino-6-[4,5-difluoro-2-piperazine-1-sulfonyl)phenyl]quinazolin-4-yl}-(1,3-dihydroisoindol-2-yl)methanone ("A94")

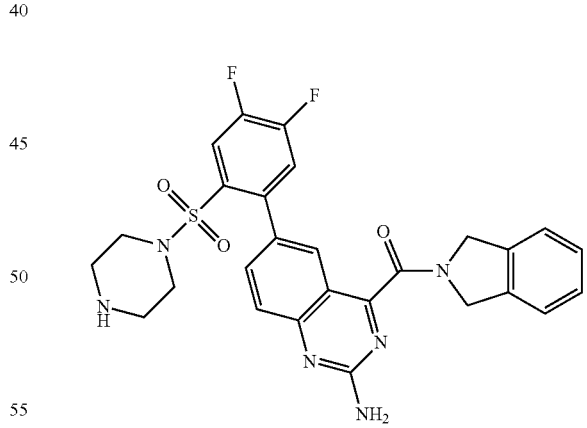

The compound is obtained from the reaction between tert-butyl 4-(2-bromo-4,5-difluorobenzenesulfonyl)piperazine-1-carboxylate and [2-amino-6-(4,4,5,5-tetramethyl-1,3,2-dioxaborolan-2-yl)quinazolin-4-yl]-(1,3-dihydroisoindol-2-yl)methanone with subsequent Boc cleavage by treatment with acid;

HPLC retention time: 1.71 min (method 1);
$^1$H NMR (500 MHz, DMSO-d$_6$/TFA-d$_1$) δ [ppm] 8.09 (dd, J=10.3, 7.9, 1H), 8.06-8.02 (m, 2H), 7.82 (d, J=8.8, 1H), 7.64

(dd, J=10.5, 7.6, 1H), 7.45 (d, J=7.2, 1H), 7.38-7.30 (m, 2H), 7.27 (d, J=7.2, 1H), 5.04 (d, J=20.5, 2H), 4.86 (s, 2H), 3.06 (m, 8H);

{2-amino-6-[5-butoxy-4-fluoro-2-(piperazine-1-sulfonyl)phenyl]quinazolin-4-yl}-(1,3-dihydroisoindol-2-yl)methanone ("A95")

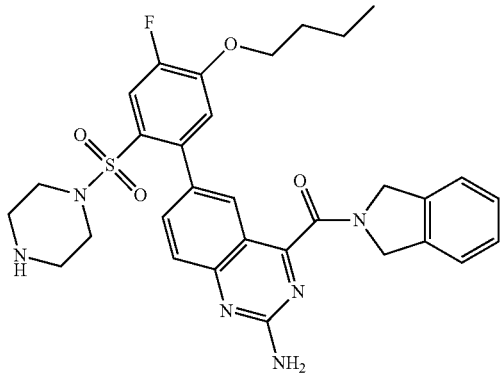 [SMILES: CCCCOc1cc(-c2ccc3nc(N)nc(C(=O)N4Cc5ccccc5C4)c3c2)c(S(=O)(=O)N2CCNCC2)cc1F]

The compound is obtained from the reaction between tert-butyl 4-(2-bromo-4,5-difluorobenzenesulfonyl)piperazine-1-carboxylate and [2-amino-6-(4,4,5,5-tetramethyl-1,3,2-dioxaborolan-2-yl)quinazolin-4-yl]-(1,3-dihydroisoindol-2-yl)methanone in butanol with subsequent Boc cleavage by treatment with acid;

HPLC retention time: 1.94 min (method 1);

¹H NMR (500 MHz, DMSO-d₆/TFA-d) δ [ppm] 8.06-8.01 (m, 2H), 7.82 (dd, J=9.7, 6.1, 2H), 7.44 (d, J=7.3, 1H), 7.38-7.29 (m, 2H), 7.26 (d, J=7.2, 1H), 7.19 (d, J=8.1, 1H), 5.03 (s, 2H), 4.88 (s, 2H), 4.13 (t, J=6.4, 2H), 3.06 (d, J=18.2, 8H), 1.77-1.68 (m, 2H), 1.48-1.36 (m, 2H), 0.91 (t, J=7.4, 3H);

2-[2-amino-4-(1,3-dihydroisoindole-2-carbonyl)quinazolin-6-yl]-4,5-difluorobenzenesulfonic acid ("A96")

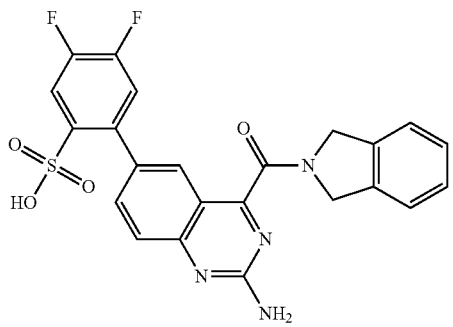 [SMILES: Nc1nc(C(=O)N2Cc3ccccc3C2)c2cc(-c3cc(F)c(F)cc3S(=O)(=O)O)ccc2n1]

HPLC retention time: 1.68 min (method 1);

¹H NMR (500 MHz, DMSO-d₆/TFA-d₁) δ [ppm] 8.39 (d, J=1.8, 1H), 8.27 (dd, J=8.7, 1.9, 1H), 7.88 (dd, J=11.1, 8.5, 1H), 7.78 (d, J=8.8, 1H), 7.44 (d, J=7.3, 1H), 7.40-7.28 (m, 3H), 7.24 (d, J=7.3, 1H), 5.02 (s, 2H), 4.86 (s, 2H);

2-[2-amino-4-(1,3-dihydroisoindole-2-carbonyl)quinazolin-6-yl]-N-ethyl-4,5-difluoro-N-(2-hydroxyethyl)benzenesulfonamide ("A97")

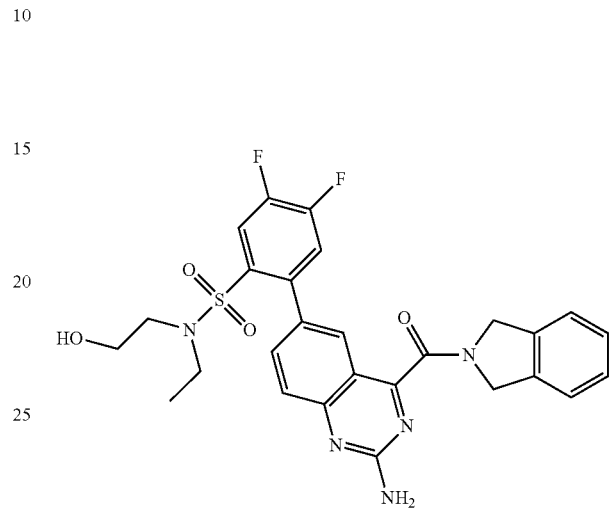

HPLC retention time: 2.01 min (method 1);

¹H NMR (500 MHz, DMSO-dB₆/TFA-d₁) δ [ppm] 8.08-8.04 (m, 2H), 8.03-7.99 (m, 1H), 7.84 (d, J=8.4, 1H), 7.57-7.51 (m, 1H), 7.44 (d, J=7.5, 1H), 7.38-7.28 (m, 2H), 7.24 (d, J=7.3, 1H), 5.01 (s, 2H), 4.83 (s, 2H), 3.32 (t, J=6.1, 2H), 2.98-2.86 (m, 4H), 0.89 (t, J=7.1, 3H);

{2-amino-6-[4,5-difluoro-2-(pyrrolidine-1-sulfonyl)phenyl]quinazolin-4-yl}-(1,3-dihydroisoindol-2-yl)methanone ("A98")

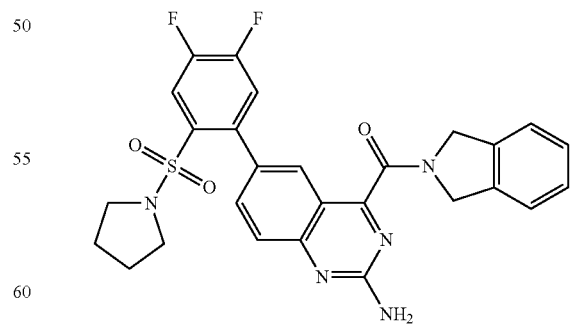

HPLC retention time: 2.26 min (method 1);

¹H NMR (500 MHz, DMSO-d₆/TFA-d₁) δ [ppm] 8.05 (dd, J=4.4, 2.6, 2H), 7.98 (dd, J=10.2, 8.0, 1H), 7.82 (d, J=8.3, 1H), 7.60-7.54 (m, 2H), 7.44 (d, J=7.3, 1H), 7.37-7.29 (m, 2H), 7.25 (d, J=7.3, 1H), 5.01 (s, 2H), 4.82 (s, 2H), 2.85 (t, J=6.5, 4H), 1.62 (t, J=6.5, 4H);

2-[2-amino-4-(1,3-dihydroisoindole-2-carbonyl)quinazolin-6-yl]-N-tert-butyl-4,5-difluoro-N-methyl-benzenesulfonamide ("A99")

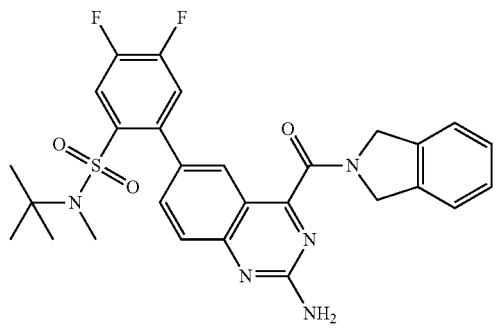 [SMILES: CN(C(C)(C)C)S(=O)(=O)c1cc(F)c(F)cc1-c1ccc2nc(N)nc(C(=O)N3Cc4ccccc4C3)c2c1]

HPLC retention time: 2.38 min (method 1);

¹H NMR (500 MHz, DMSO-d₆/TFA-d₁) δ [ppm] 8.08-8.03 (m, 2H), 7.99 (dd, J=10.4, 8.0, 1H), 7.87 (d, J=9.4, 1H), 7.51 (dd, J=10.3, 7.5, 1H), 7.44 (d, J=7.3, 1H), 7.32 (dd, J=17.0, 7.8, 2H), 7.24 (d, J=7.3, 1H), 5.02 (s, 2H), 4.84 (s, 2H), 2.19 (s, 3H), 1.09 (s, 9H);

{2-amino-6-[2-(3,3-difluoropyrrolidine-1-sulfonyl)-4,5-difluorophenyl]quinazolin-4-yl}-(1,3-dihydroisoindol-2-yl)methanone ("A100")

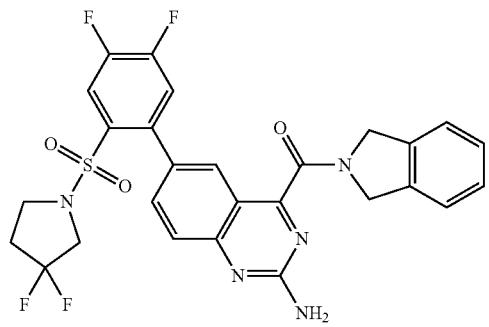 [SMILES: Nc1nc(C(=O)N2Cc3ccccc3C2)c2cc(-c3cc(F)c(F)cc3S(=O)(=O)N3CCC(F)(F)C3)ccc2n1]

HPLC retention time: 2.3 min (method 1);

¹H NMR (500 MHz, DMSO-d₆/TFA-d₁) δ [ppm] 8.05-8.01 (m, 1H), 7.99 (dd, J=10.2, 2.8, 2H), 7.79 (d, J=8.6, 1H), 7.53 (dd, J=10.2, 7.6, 1H), 7.38 (d, J=7.2, 1H), 7.32-7.22 (m, 2H), 7.19 (d, J=7.3, 1H), 4.96 (s, 2H), 4.78 (s, 2H), 3.30 (t, J=12.6, 2H), 3.08 (t, J=7.3, 2H), 2.20 (tt, J=14.1, 7.2, 2H);

{2-amino-6-[4,5-difluoro-2-(3-hydroxypyrrolidine-1-sulfonyl)phenyl]quinazolin-4-yl}-(1,3-dihydroisoindol-2-yl)methanone ("A101")

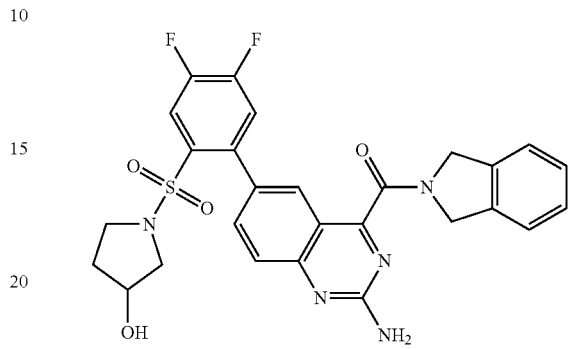

HPLC retention time: 1.97 min (method 1);

¹H NMR (500 MHz, DMSO-d₆/TFA-d₁) δ [ppm] 8.07 (s, 3H), 7.84-7.80 (m, 1H), 7.57 (dd, J=10.6, 7.5, 1H), 7.44 (d, J=7.3, 1H), 7.39-7.28 (m, 2H), 7.25 (d, J=7.3, 1H), 5.02 (s, 2H), 4.83 (s, 2H), 4.14 (s, 1H), 3.09 (dd, J=16.2, 9.3, 1H), 2.99 (ddd, J=24.6, 14.7, 6.5, 3H), 1.81-1.71 (m, 1H), 1.70-1.63 (m, 1H);

{2-amino-6-[4,5-difluoro-2-(3-methylpiperazine-1-sulfonyl)phenyl]quinazolin-4-yl}-(1,3-dihydroisoindol-2-yl)methanone ("A102")

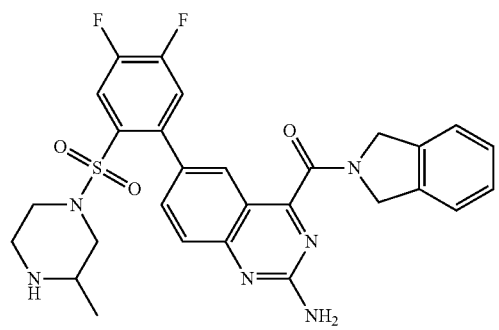 [SMILES: CC1CN(S(=O)(=O)c2cc(F)c(F)cc2-c2ccc3nc(N)nc(C(=O)N4Cc5ccccc5C4)c3c2)CCN1]

HPLC retention time: 1.68 min (method 1);

¹H NMR (500 MHz, DMSO-d₆/TFA-d₁) δ [ppm] 8.10-8.06 (m, 2H), 8.04 (dd, J=8.7, 1.9, 1H), 7.84 (d, J=8.6, 1H), 7.61 (dd, J=10.5, 7.5, 1H), 7.44 (d, J=7.3, 1H), 7.38-7.30 (m, 2H), 7.26 (d, J=7.2, 1H), 5.03 (s, 2H), 4.88 (s, 2H), 3.33 (d, J=13.0, 2H), 3.27-3.14 (m, 2H), 2.91 (td, J=12.4, 2.8, 1H), 2.83 (t, J=11.5, 1H), 2.66 (dd, J=13.4, 10.6, 1H), 1.14 (d, J=6.4, 3H);

{2-amino-6-[4,5-difluoro-2-(3-trifluoromethylpip-erazine-1-sulfonyl)phenyl]-quinazolin-4-yl}-(1,3-dihydroisoindol-2-yl)methanone ("A103")

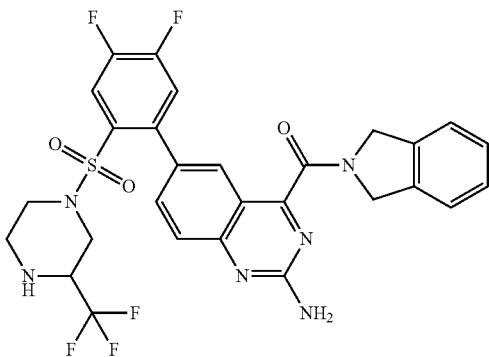 [SMILES: Nc1nc(C(=O)N2Cc3ccccc3C2)c2cc(-c3cc(F)c(F)cc3S(=O)(=O)N3CCNC(C(F)(F)F)C3)ccc2n1]

HPLC retention time: 2.23 min (method 1);

$^1$H NMR (500 MHz, DMSO-d$_6$/TFA-d$_1$) δ [ppm] 8.18-8.09 (m, 3H), 8.06 (d, J=8.6, 1H), 7.85 (d, J=8.6, 1H), 7.59 (t, J=8.8, 1H), 7.44 (d, J=7.3, 1H), 7.34 (dt, J=15.0, 7.3, 2H), 7.26 (d, J=7.3, 1H), 5.04 (s, 2H), 4.87 (s, 2H), 4.43 (s, 1H), 3.59 (d, J=12.1, 1H), 3.33 (d, J=10.8, 2H), 3.17-3.01 (m, 2H), 2.97 (t, J=11.5, 1H);

{2-amino-6-[2-(3,5-dimethylpiperazine-1-sulfonyl)-4,5-difluorophenyl]quinazolin-4-yl}-(1,3-dihydroisoindol-2-yl)methanone ("A104")

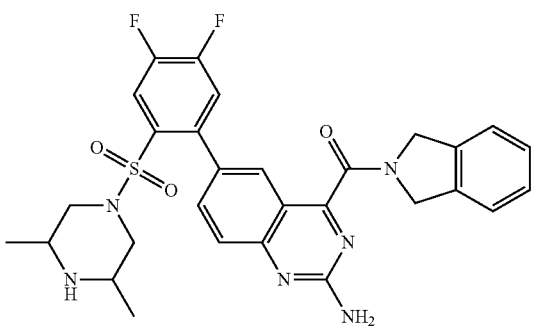 [SMILES: CC1CN(S(=O)(=O)c2cc(F)c(F)cc2-c2ccc3nc(N)nc(C(=O)N4Cc5ccccc5C4)c3c2)CC(C)N1]

HPLC retention time: 1.74 min (method 1);

$^1$H NMR (500 MHz, DMSO-d$_6$/TFA-d$_1$) δ [ppm] 8.09 (t, J=7.6, 1H), 8.05 (d, J=1.5, 1H), 8.03 (dd, J=8.6, 1.8, 1H), 7.80 (d, J=8.6, 1H), 7.68-7.61 (m, 1H), 7.45 (d, J=7.2, 1H), 7.38-7.29 (m, 2H), 7.26 (d, J=7.2, 1H), 5.00 (s, 2H), 4.86 (s, 2H), 3.39 (d, J=12.5, 2H), 3.18 (s, 2H), 1.24-0.99 (m, 6H);

$^1$H NMR (500 MHz, DMSO-d$_6$) δ 7.96 (dd, J=10.5, 8.1, 1H), 7.74 (d, J=1.8, 1H), 7.71 (dd, J=8.8, 2.0, 1H), 7.62 (dd, J=10.8, 7.7, 1H), 7.52 (d, J=8.6, 1H), 7.42 (d, J=7.3, 1H), 7.34-7.28 (m, 1H), 7.26 (t, J=6.0, 2H), 7.18 (s, 2H), 4.93 (s, 2H), 4.73 (s, 2H), 2.95 (d, J=9.7, 2H), 2.34-2.24 (m, 2H), 1.74 (t, J=11.1, 2H), 0.69 (d, J=6.2, 6H).

The following compound is obtained analogously to the preparation of "A69", step 2

2-[2-amino-4-(1,3-dihydroisoindole-2-carbonyl) quinazolin-6-yl]-4,5-difluorobenzoic acid ("A105")

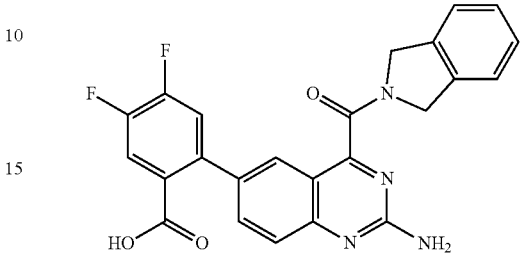

The compound is obtained from the reaction between ethyl 2-bromo-4,5-difluorobenzoate and [2-amino-6-(4,4,5,5-tet-ramethyl-1,3,2-dioxaborolan-2-yl)quinazolin-4-yl]-(1,3-di-hydroisoindol-2-yl)methanone with subsequent hydrolysis of the ethyl ester;

HPLC retention time: 1.98 min (method 2);

$^1$H NMR (500 MHz, DMSO-d$_6$/TFA-d$_1$) δ [ppm] 8.06 (d, J=1.8, 1H), 8.02 (dd, J=8.6, 2.0, 1H), 7.94 (dd, J=10.9, 8.2, 1H), 7.81 (dd, J=9.1, 3.9, 1H), 7.52 (dd, J=11.0, 7.7, 1H), 7.45 (d, J=7.2, 1H), 7.38-7.29 (m, 2H), 7.27 (d, J=7.5, 1H), 5.04 (s, 2H), 4.87 (s, 2H).

The following examples relate to pharmaceutical compositions:

EXAMPLE A

Injection Vials

A solution of 100 g of an active ingredient according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of NaH$_2$PO$_4$.2; H$_2$O, 28.48 g of Na$_2$HPO$_4$.12; H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula

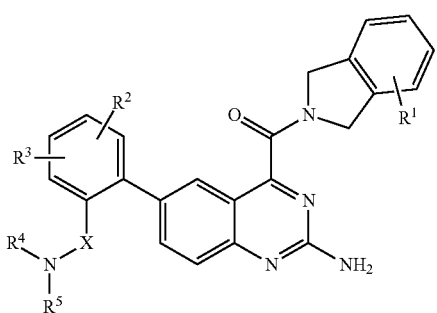

I in which
$R^1$ denotes H, $(CH_2)_n$Het, $(CH_2)_n$Ar, Hal or A,
$R^2$, $R^3$ each, independently of one another, denote H, $(CH_2)_n$Het, $(CH_2)_n$Ar, Hal, OH or OA,
$R^4$, $R^5$ each, independently of one another, denote H, A, $(CH_2)_n$Het, $(CH_2)_n$Ar or $(CH_2)_pOC(=O)(CH_2)_pNH_2$,
$R^4$ and $R^5$, together with the N atom to which they are bonded, also denote a saturated, unsaturated or aromatic mono- or bicyclic heterocycle which is unsubstituted or mono-, di- or trisubstituted by Hal, A, $(CH_2)_n$OH, $(CH_2)_n$OA, $(CH_2)_n$NH$_2$, $(CH_2)_n$COOH, $(CH_2)_n$COOA, NHCOA, NA'COA, CONH$_2$, CONHA, CONAA', OC(=O)(CH$_2$)$_p$NH$_2$ and/or =O (carbonyl oxygen) and which may contain a further 1 to 3 N, O and/or S atoms, and in which, in addition, one N atom may be oxidised,
X denotes CO or SO$_2$,
Ar denotes phenyl, naphthyl, tetrahydronaphthyl or biphenyl, each of which is unsubstituted or mono-, di-, tri-, tetra- or pentasubstituted by A, Hal, $(CH_2)_n$OA, $(CH_2)_n$OH, $(CH_2)_n$CN, SA, SOA, SO$_2$A, NO$_2$, C≡CH, $(CH_2)_n$COOH, CHO, $(CH_2)_n$COOA, CONH$_2$, CONHA, CONAA', NHCOA, CH(OH)A, $(CH_2)_n$NH$_2$, $(CH_2)_n$NHA, $(CH_2)_n$NAA', $(CH_2)_n$NHSO$_2$A, SO$_2$NH(CH$_2$)$_n$NH$_2$, SO$_2$NH$_2$, SO$_2$NHA, SO$_2$NAA', CONH(CH$_2$)$_n$COOA, CONH(CH$_2$)$_n$COOH, NHCO(CH$_2$)$_n$COOA, NHCO(CH$_2$)$_n$COOH, CONH(CH$_2$)$_n$NH$_2$, CONH(CH$_2$)$_n$NHA, CONH(CH$_2$)$_n$NAA', CONH(CH$_2$)$_n$CN and/or $(CH_2)_n$CH(NH$_2$)COOH,
Het denotes a mono- or bicyclic saturated, unsaturated or aromatic heterocycle having 1 to 4 N, O and/or S atoms, which may be unsubstituted or mono-, di- or trisubstituted by A, OA, OH, phenyl, SH, S(O)$_m$A, Hal, NO$_2$, CN, COA, COOA, COObenzyl, CONH$_2$, CONHA, CONAA', SO$_2$NH$_2$, NH$_2$, NHA, NAA', NHCOA, NHSO$_2$A and/or =O (carbonyl oxygen),
A, A' each, independently of one another, denote unbranched or branched alkyl having 1-10 C atoms, in which 1-3 non-adjacent CH$_2$ groups may be replaced by O, S, SO, SO$_2$, NH, NMe or NEt and/or, in addition, 1-5 H atoms may be replaced by F and/or Cl,
or cyclic alkyl having 3-8 C atoms,
n denotes 0, 1, 2, 3 or 4,
p denotes 1, 2, 3 or 4,
and pharmaceutically usable salts and stereoisomers thereof, including mixtures thereof in al ratios.
2. Compounds according to claim 1 in which
Het denotes pyridyl, pyrimidinyl, furyl, thienyl, pyrrolyl, pyrazolyl, triazolyl, oxazolyl, isoxazolyl, thiazolyl, benzothiazolyl, benzo-1,4-dioxanyl, quinolyl, isoquinolyl, quinazolinyl, benzimidazolyl, indazolyl, indolyl, 1,3-dihydroisoindolyl, benzofuranyl, dihydrobenzofuranyl, benzo-1,3-dioxolyl, piperazinyl, pyrazinyl, pyridazinyl, morpholinyl, azepanyl, azetidinyl, pyrrolidinyl or piperidinyl, each of which is unsubstituted or mono-, di- or trisubstituted by A, OA, OH, Hal, CN and/or =O (carbonyl oxygen),
and pharmaceutically usable salts, tautomers and stereoisomers thereof, including mixtures thereof in all ratios.
3. Compounds according to claim 1 in which
Ar denotes phenyl which is unsubstituted or mono-, di-, tri-, tetra- or pentasubstituted by A, Hal and/or OA,
and pharmaceutically usable salts, tautomers and stereoisomers thereof, including mixtures thereof in all ratios.
4. Compounds according to claim 1 in which
A,A' each, independently of one another, denote unbranched or branched alkyl having 1-6 C atoms, in which 1-2 non-adjacent CH$_2$ groups may be replaced by O, NH, NMe or NEt and/or, in addition, 1-5 H atoms may be replaced by F and/or Cl,
or cyclic alkyl having 3-8 C atoms,
and pharmaceutically usable salts, tautomers and stereoisomers thereof, including mixtures thereof in all ratios.

5. Compounds according to claim 1 in which

Het denotes pyridyl, pyrimidinyl, furyl, thienyl, pyrrolyl, imidazolyl, pyrazolyl, triazolyl, oxazolyl, isoxazolyl, thiazolyl, piperazinyl, pyrazinyl, pyridazinyl, morpholinyl, azepanyl, azetidinyl, pyrrolidinyl or piperidinyl, each of which is unsubstituted or mono-, di- or trisubstituted by A, OA, OH, Hal, CN and/or =O (carbonyl oxygen), and pharmaceutically usable salts, tautomers and stereoisomers thereof, including mixtures thereof in all ratios.

6. Compounds according to claim 1 in which $R^4$ and $R^5$, together with the N atom to which they are bonded, also denote 1,3-dihydroisoindolyl, pyrrolidinyl, azetidinyl, azepanyl, piperazinyl, piperidinyl, morpholinyl, pyridyl, imidazolyl, benzimidazolyl, triazolyl or pyrimidinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA', OC(=O)$(CH_2)_pNH_2$ and/or =O (carbonyl oxygen), and in which, in addition, one N atom may be oxidised, and pharmaceutically usable salts, tautomers and stereoisomers thereof, including mixtures thereof in all ratios.

7. Compounds according to claim 1 in which $R^1$ denote H, Hal or A, and pharmaceutically usable salts, tautomers and stereoisomers thereof, including mixtures thereof in all ratios.

8. Compounds according to claim 1 in which $R^2$, $R^3$ each, independently of one another, denote H, Hal, OH or OA, and pharmaceutically usable salts, tautomers and stereoisomers thereof, including mixtures thereof in all ratios.

9. Compounds according to claim 1 in which $R^1$ denotes H, Hal or A, $R^2$, $R^3$ each, independently of one another, denote H, Hal, OH or OA, $R^4$, $R^5$ each, independently of one another, denote H, A, $(CH_2)_n$Het, $(CH_2)_n$Ar or $(CH_2)_pOC(=O)(CH_2)_pNH_2$, $R^4$ and $R^5$, together with the N atom to which they are bonded, also denote 1,3-dihydroisoindolyl, pyrrolidinyl, azetidinyl, azepanyl, piperazinyl, piperidinyl, morpholinyl, pyridyl, pyrrolyl, imidazolyl, benzimidazolyl, triazolyl or pyrimidinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)COOA$, NHCOA, NA'COA, $CONH_2$, CONHA, CONAA', OC(=O)$(CH_2)_pNH_2$ and/or =O (carbonyl oxygen), and in which, in addition, one N atom may be oxidised, X denotes CO or $SO_2$, Ar denotes phenyl which is unsubstituted or mono-, di-, tri-, tetra- or pentasubstituted by A, Hal and/or OA, Het denotes pyridyl, furyl, thienyl, pyrrolyl, imidazolyl, pyrazolyl, triazolyl, oxazolyl, isoxazolyl, thiazolyl, piperazinyl, pyrazinyl, pyridazinyl, morpholinyl, azepanyl, azetidinyl, pyrrolidinyl or piperidinyl, each of which is unsubstituted or mono-, di- or trisubstituted by A, OA, OH, Hal, CN and/or =O (carbonyl oxygen), A, A' each, independently of one another, denote unbranched or branched alkyl having 1-6 C atoms, in which 1-2 non-adjacent $CH_2$ groups may be replaced by O, NH, NMe or NEt and/or, in addition, 1-5 H atoms may be replaced by F and/or Cl, or cyclic alkyl having 3-8 C atoms, n denotes 0, 1, 2, 3 or 4, p denotes 1, 2, 3 or 4, and pharmaceutically usable salts, tautomers and stereoisomers thereof, including mixtures thereof in all ratios.

10. Compounds according to claim 1 selected from the group

| Compound No. | Structure and/or name |
|---|---|
| "A1" | 2-[2-Amino-4-(1,3-dihydroisoindole-2-carbonyl)quinazolin-6-yl]-N-tert-butylbenzenesulfonamide |
| "A2" | 2-[2-Amino-4-(1,3-dihydroisoindole-2-carbonyl)quinazolin-6-yl]-benzenesulfonamide |
| "A3" | 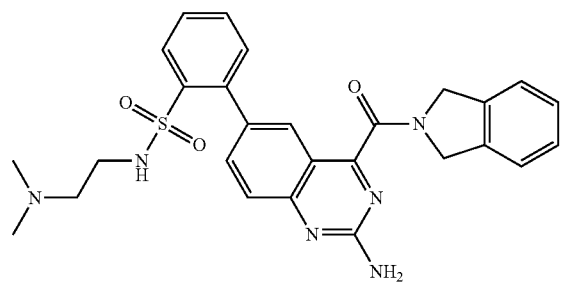 2-[2-Amino-4-(1,2-dihydroisoindole-2-carbonyl)quinazolin-6-yl]-N-(2-dimethylaminoethyl)benzenesulfonamide |

-continued

| Compound No. | Structure and/or name |
|---|---|
| "A4" | 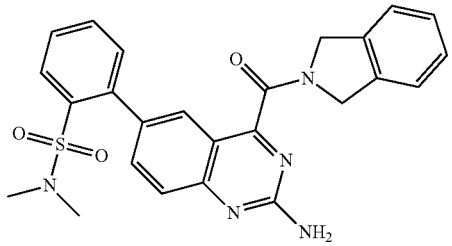
2-[2-Amino-4-(1,3-dihydroisoindole-2-carbonyl)quinazolin-6-yl]-N,N-dimethylbenzenesulfonamide |
| "A5" | 2-[2-Amino-4-(1,3-dihydroisoindole-2-carbonyl)quinazolin-6-yl]-N-ethylbenzenesulfonamide |
| "A6" | 2-[2-Amino-4-(1,3-dihydroisoindole-2-carbonyl)quinazolin-6-yl]-N-methylbenzenesulfonamide |
| "A7" | 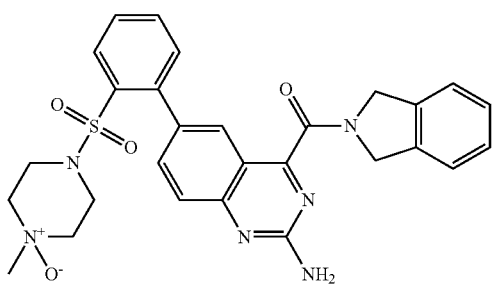
{2-Amino-6-[2-(4-methyl-4-oxypiperazine-1-sulfonyl)phenyl]-quinazolin-4-yl}-(1,3-dihydroisoindol-2-yl)methanone |
| "A8" | 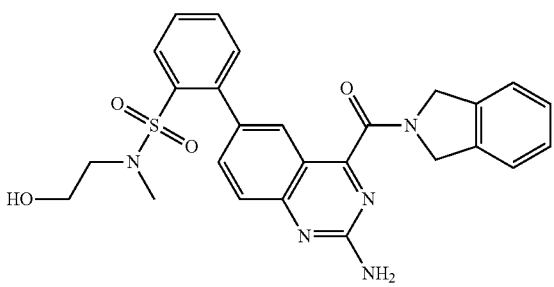
2-[2-Amino-4-(1,3-dihydroisoindole-2-carbonyl)quinazolin-6-yl]-N-(2-hydroxyethyl)-N-methylbenzenesulfonamide |
| "A9" | 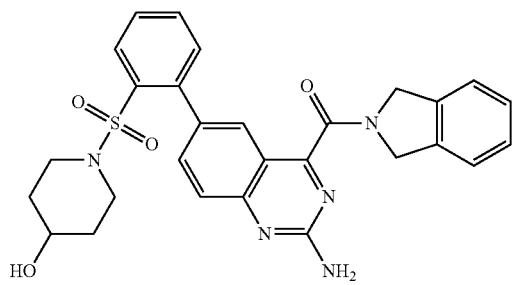
{2-Amino-6-[2-(4-hydroxypiperidine-1-sulfonyl)phenyl]-quinazolin-4-yl}-(1,3-dihydroisoindol-2-yl)methanone |

| Compound No. | Structure and/or name |
|---|---|
| "A10" | 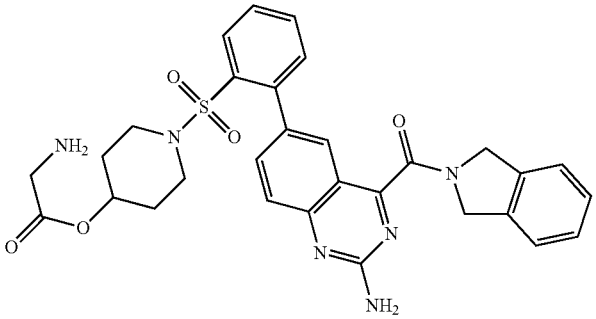<br>1-{2-[2-Amino-4-(1,3-dihydroisoindole-2-carbonyl)quinazolin-6-yl]benzenesulfonyl}piperidin-4-yl aminoacetate |
| "A11" | 2-[2-Amino-4-(1,3-dihydroisoindole-2-carbonyl)quinazolin-6-yl]-N-(2-hydroxyethyl)benzenesulfonamide |
| "A12" | 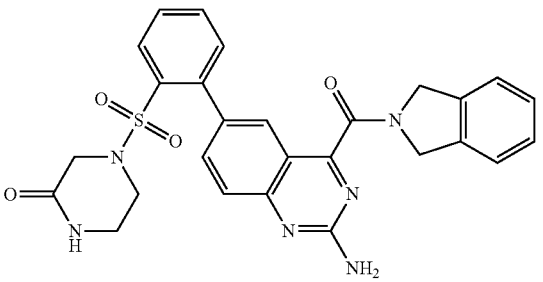<br>4-{2-[2-Amino-4-(1,3-dihydroisoindole-2-carbonyl)quinazolin-6-yl]benzenesulfonyl}piperazin-2-one |
| "A13" | 2-[2-Amino-4-(1,3-dihydroisoindole-2-carbonyl)quinazolin-6-yl]-N-methyl-N-(2-methylaminoethyl)benzenesulfonamide |
| "A14" | 2-[2-Amino-4-(1,3-dihydroisoindole-2-carbonyl)quinazolin-6-yl]-N-(2-aminoethyl)benzenesulfonamide |
| "A15" | 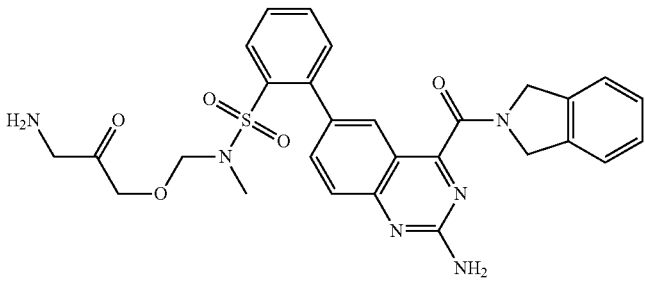<br>2-({2-[2-Amino-4-(1,3-dihydroisoindole-2-carbonyl)quinazolin-6-yl]benzenesulfonyl}methylamino)ethyl aminoacetate |
| "A16" | 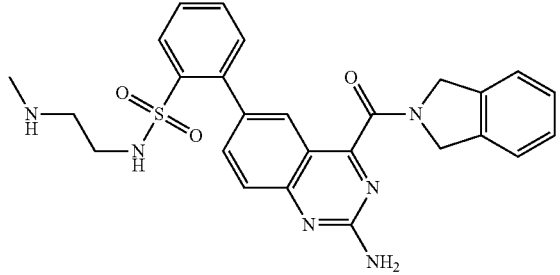<br>2-[2-Amino-4-(1,3-dihydroisoindole-2-carbonyl)quinazolin-6-yl]-N-(2-methylaminoethyl)benzenesulfonamide |

-continued

| Compound No. | Structure and/or name |
|---|---|
| "A17" | 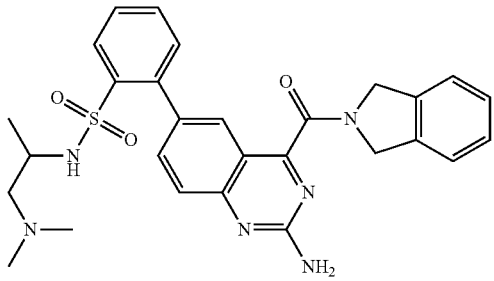
2-[2-Amino-4-(1,3-dihydroisoindole-2-carbonyl)quinazolin-6-yl]-N-(2-dimethylamino-1-methylethyl)benzenesulfonamide |
| "A18" | 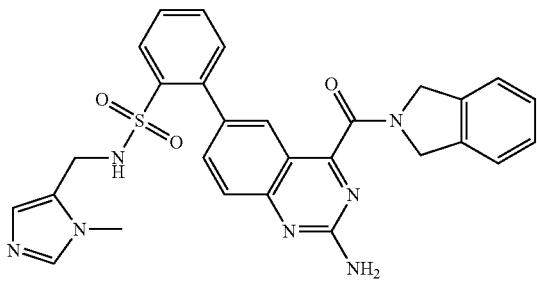
2-[2-Amino-4-(1,3-dihydroisoindole-2-carbonyl)quinazolin-6-yl]-N-methyl-N-(3-methyl-3H-imidazol-4-ylmethyl)-benzenesulfonamide |
| "A19" | {2-Amino-6-[2-(2-methylpyrrolidine-1-sulfonyl)phenyl]-quinazolin-4-yl}-(1,3-dihydroisoindol-2-yl)methanone |
| "A20" | 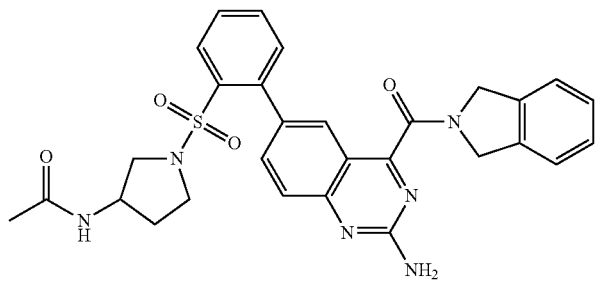
N-(1-{2-[2-Amino-4-(1,3-dihydroisoindole-2-carbonyl)-quinazolin-6-yl]benzenesulfonyl}pyrrolidin-3-yl)acetamide |
| "A21" | [2-Amino-6-[2-(3-hydroxymethylpyrrolidine-1-sulfonyl)phenyl]-quinazolin-4-yl}-(1,3-dihydroisoindol-2-yl)methanone |
| "A22" | 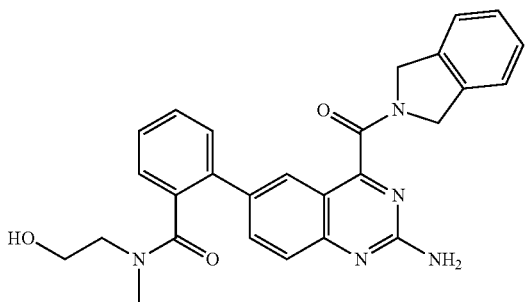
2-[2-Amino-4-(1,3-dihydroisoindole-2-carbonyl)quinazolin-6-yl]-N-(2-hydroxyethyl)-N-methylbenzamide |

-continued

| Compound No. | Structure and/or name |
|---|---|
| "A23" | 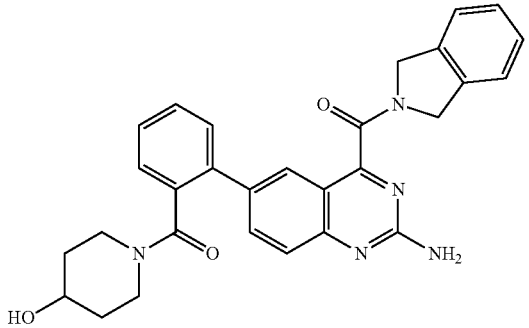<br>{2-Amino-6-[2-(4-hydroxypiperidine-1-carbonyl)phenyl]-quinazolin-4-yl}-(1,3-dihydroisoindol-2-yl)methanone |
| "A24" | 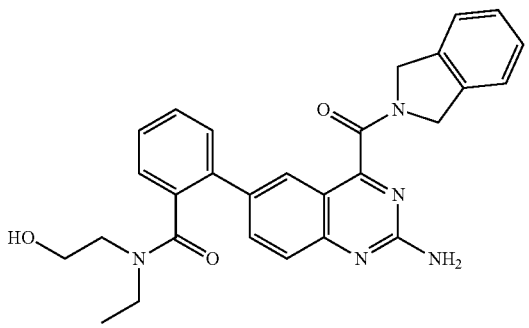<br>2-[2-Amino-4-(1,3-dihydroisoindole-2-carbonyl)quinazolin-6-yl]-N-ethyl-N-(2-hydroxyethyl)benzamide |
| "A25" | 2-[2-Amino-4-(1,3-dihydroisoindole-2-carbonyl)quinazolin-6-yl]-N-ethyl-N-(2-hydroxyethyl)benzenesulfonamide |
| "A26" | 2-[2-Amino-4-(1,3-dihydroisoindole-2-carbonyl)quinazolin-6-yl]-N-azetidin-3-ylbenzenesulfonamide |
| "A27" | {2-Amino-6-[2-(imidazole-1-sulfonyl)phenyl]quinazolin-4-yl}-(1,3-dihydroisoindol-2-yl)methanone |
| "A28" | {2-Amino-6-[2-(2-methylimidazole-1-sulfonyl)phenyl]-quinazolin-4-yl}-(1,3-dihydroisoindol-2-yl)methanone |
| "A29" | {2-Amino-6-[2-(3-aminoazetidine-1-sulfonyl)phenyl]quinazolin-4-yl}-(1,3-dihydroisoindol-2-yl)methanone |
| "A30" | {2-Amino-6-[2-(4-methylimidazole-1-sulfonyl)phenyl]-quinazolin-4-yl}-(1,3-dihydroisoindol-2-yl)methanone |
| "A31" | 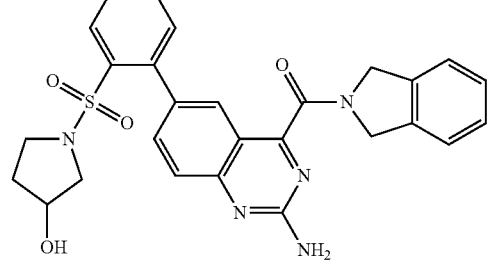<br>{2-Amino-6-[2-(3-hydroxypyrrolidine-1-sulfonyl)phenyl]-quinazolin-4-yl}-(1,3-dihydroisoindol-2-yl)methanone |
| "A32" | {2-Amino-6-[2-(pyrrolidine-1-sulfonyl)phenyl]quinazolin-4-yl}-(1,3-dihydroisoindol-2-yl)methanone |
| "A33" | {2-Amino-6-[2-(3-aminopyrrolidine-1-sulfonyl)phenyl]-quinazolin-4-yl}-(1,3-dihydroisoindol-2-yl)methanone |
| "A34" | {2-Amino-6-[2-(4-methylpiperazine-1-carbonyl)phenyl]-quinazolin-4-yl}-(1,3-dihydroisoindol-2-yl)methanone |

| Compound No. | Structure and/or name |
|---|---|
| "A35" | 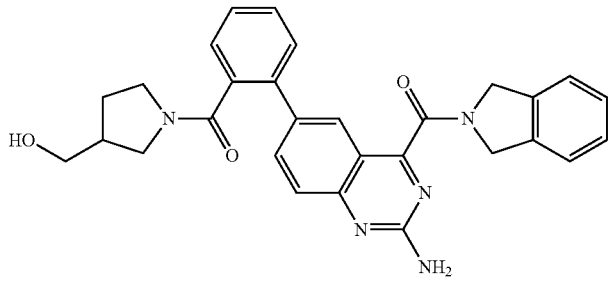<br>{2-Amino-6-[2-(3-hydroxymethylpyrrolidine-1-carbonyl)-phenyl]quinazolin-4-yl}-(1,3-dihydroisoindol-2-yl)methanone |
| "A36" | 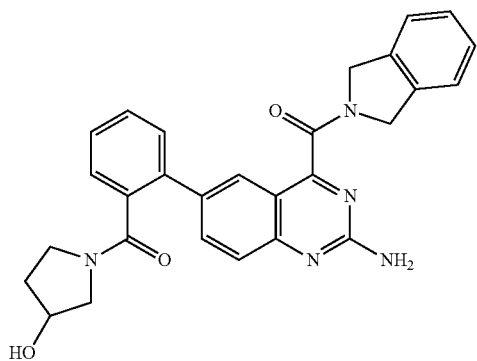<br>{2-Amino-6-[2-(3-hydropyrrolidine-1-carbonyl)phenyl]-quinazolin-4-yl}-(1,3-dihydroisoindol-2-yl)methanone |
| "A37" | 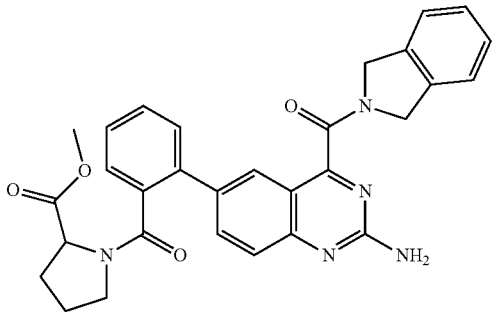<br>Methyl 1-{2-[2-Amino-4-(1,3-dihydroisoindole-2-carbonyl)-quinazolin-6-yl]benzoyl}pyrrolidine-2-carboxylate |
| "A38" | 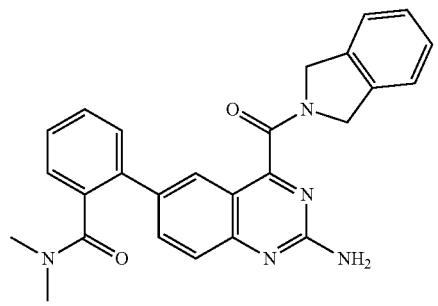<br>2-[2-Amino-4-(1,3-dihydroisoindole-2-carbonyl)quinazolin-6-yl]-N,N-dimethylbenzamide |

-continued

| Compound No. | Structure and/or name |
|---|---|
| "A39" | 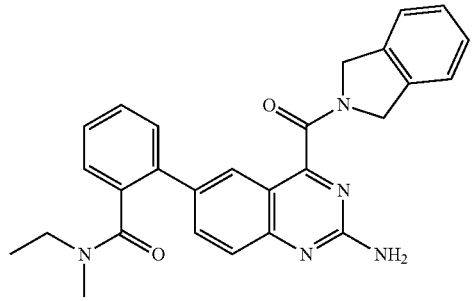
2-[2-Amino-4-(1,3-dihydroisoindole-2-carbonyl)quinazolin-6-yl]-N-ethyl-N-methylbenzamide |
| "A40" | 2-[2-Amino-4-(1,3-dihydroisoindole-2-carbonyl)quinazolin-6-yl]-N,N-diethylbenzamide |
| "A41" | 2-[2-Amino-4-(1,3-dihydroisoindole-2-carbonyl)quinazolin-6-yl]-N-ethylbenzamide |
| "A42" | {2-Amino-6-[2-(2-methylpyrrolidine-1-carbonyl)phenyl]-quinazolin-4-yl}-(1,3-dihydroisoindol-2-yl)methanone |
| "A43" | {2-Amino-6-[2-(3-aminopyrrolidine-1-carbonyl)phenyl]-quinazolin-4-yl}-(1,3-dihydroisoindol-2-yl)methanone |
| "A44" | 1-{2-[2-Amino-4-(1,3-dihydroisoindole-2-carbonyl)quinazolin-6-yl]benzoyl}pyrrolidine-2-carboxylic acid |
| "A45" | 2-[2-Amino-4-(1,3-dihydroisoindole-2-carbonyl)quinazolin-6-yl]-N,N-diethylbenzenesulfonamide |
| "A46" | 2-[2-Amino-4-(1,3-dihydroisoindole-2-carbonyl)quinazolin-6-yl]-N-cyclobutylbenzamide |
| "A47" | 2-[2-Amino-4-(1,3-dihydroisoindole-2-carbonyl)quinazolin-6-yl]-N-tert-butylbenzamide |
| "A48" | 2-[2-Amino-4-(1,3-dihydroisoindole-2-carbonyl)quinazolin-6-yl]-N-cyclopropylbenzamide |
| "A49" | {2-Amino-6-[2-(3,3-difluoropyrrolidine-1-carbonyl)phenyl]-quinazolin-4-yl}-(1,3-dihydroisoindol-2-yl)methanone |
| "A50" | 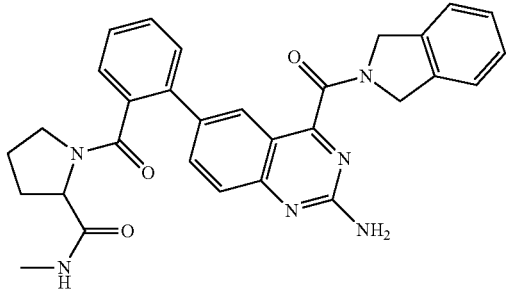
1-{2-[2-Amino-4-(1,3-dihydroisoindole-2-carbonyl)quinazolin-6-yl]benzoyl}pyrrolidine-2-methylamide |
| "A51" | 2-[2-Amino-4-(1,3-dihydroisoindole-2-carbonyl)quinazolin-6-yl]-N-cyclobutylbenzenesulfonamide |
| "A52" | 2-[2-Amino-4-(1,3-dihydroisoindole-2-carbonyl)quinazolin-6-yl]-N-cyclopropylbenzenesulfonamide |
| "A53" | {2-Amino-6-[2-(3,3-difluoropyrrolidine-1-sulfonyl)phenyl]-quinazolin-4-yl}-(1,3-dihydroisoindol-2-yl)methanone |

-continued

| Compound No. | Structure and/or name |
|---|---|
| "A54" | 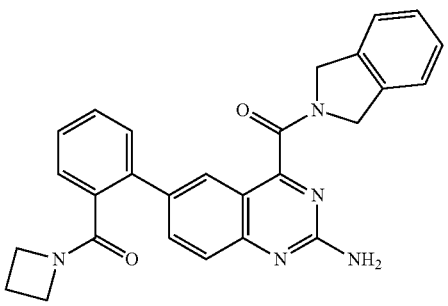
{2-Amino-6-[2-(azetidine-1-carbonyl)phenyl]quinazolin-4-yl}-(1,3-dihydroisoindol-2-yl)methanone |
| "A55" | 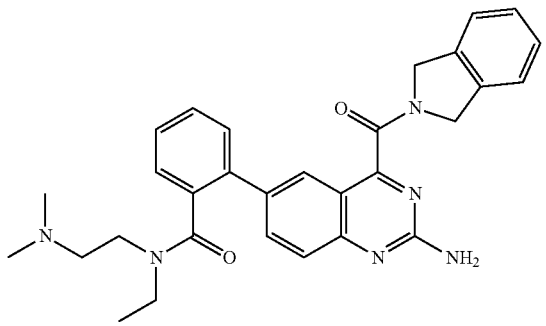
2-[2-Amino-4-(1,3-dihydroisoindole-2-carbonyl)quinazolin-6-yl]-N-(2-dimethylaminoethyl)-N-ethylbenzamide |
| "A56" | 2-[2-Amino-4-(1,3-dihydroisoindole-2-carbonyl)quinazolin-6-yl]-N-tert-butyl-N-methylbenzamide |
| "A57" | 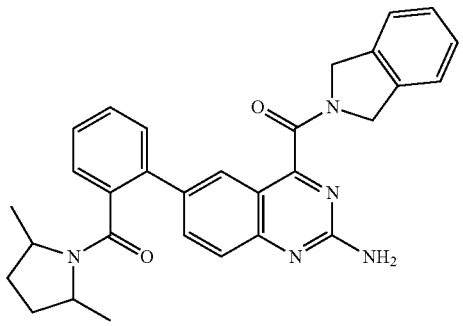
{2-Amino-6-[2-(2,5-dimethylpyrrolidine-1-carbonyl)phenyl]-quinazolin-4-yl}-(1,3-dihydroisoindol-2-yl)methanone |
| "A58" | 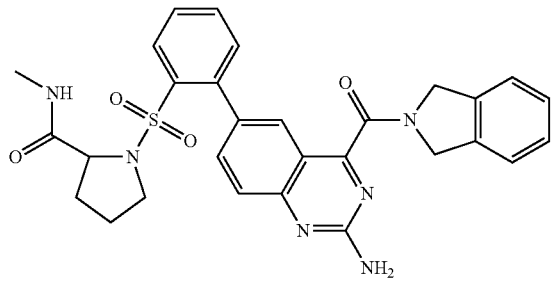
1-{2-[2-Amino-(1,3-dihydroisoindole-2-carbonyl)quinazolin-6-yl]benzenesulfonyl}pyrrolidine-2-methylamide |

-continued

| Compound No. | Structure and/or name |
|---|---|
| "A59" | 2-[2-Amino-4-(1,3-dihydroisoindole-2-carbonyl)quinazolin-6-yl]-N-tert-butyl-N-methylbenzenesulfonamide |
| "A60" | 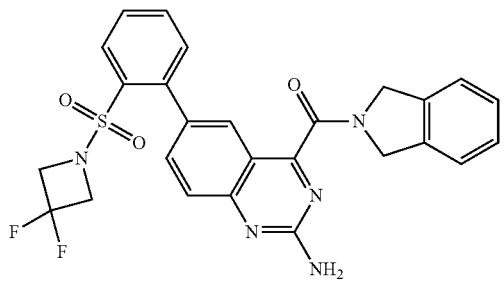<br>{2-Amino-6-[2-(3,3-difluoroazetidine-1-sulfonyl)phenyl]-quinazolin-4-yl}-(1,3-dihydroisoindol-2-yl)methanone |
| "A61" | N-(2-Hydroxyethyl)-1-{2-[2-amino-4-(1,3-dihydroisoindole-2-carbonyl)quinazolin-6-yl]benzenesulfonyl}pyrrolidine-2-carboxamide |
| "A62" | 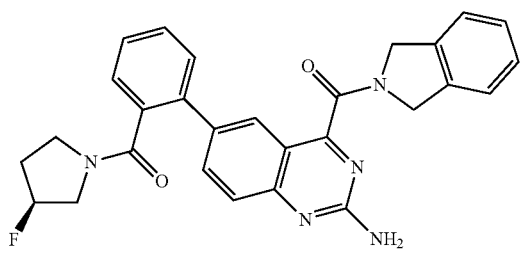<br>{2-Amino-6-[2-((S)-3-fluoropyrrolidine-1-carbonyl)phenyl]-quinazolin-4-yl}-(1,3-dihydroisoindol-2-yl)methanone |
| "A63" | 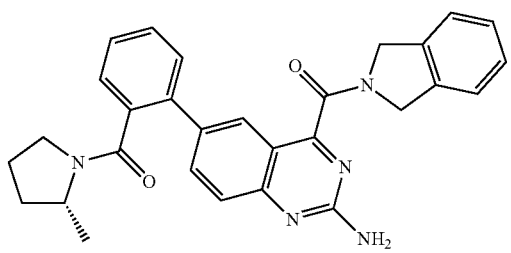<br>{2-Amino-6-[2-((R)-2-methylpyrrolidine-1-carbonyl)phenyl]-quinazolin-4-yl}-(1,3-dihydroisoindol-2-yl)methanone |
| "A64" | {2-Amino-6-[2-(2,5-dimethylpyrrolidine-1-sulfonyl)phenyl]-quinazolin-4-yl}-(1,3-dihydroisoindol-2-yl)methanone |
| "A65" | 2-[2-Amino-4-(1,3-dihydroisoindole-2-carbonyl)quinazolin-6-yl]-N-cyclopropyl-N-methylbenzenesulfonamide |
| "A66" | {2-Amino-6-[2-((R)-2-methylpyrrolidine-1-sulfonyl)phenyl]-quinazolin-4-yl}-(1,3-dihydroisoindol-2-yl)methanone |
| "A67" | {2-Amino-6-[2-((S)-3-fluoropyrrolidine-1-sulfonyl)phenyl]-quinazolin-4-yl}-(1,3-dihydroisoindol-2-yl)methanone |

-continued

| Compound No. | Structure and/or name |
|---|---|
| "A68" | 2-[2-Amino-4-(1,3-dihydroisoindole-2-carbonyl)quinazolin-6-yl]-N-azetidin-3-yl-N-methylbenzenesulfonamide |
| "A69" | 2-[2-Amino-4-(1,3-dihydroisoindole-2-carbonyl)quinazolin-6-yl]-N,N-diethyl-4,5-difluorobenzamide |
| "A70" | 2-[2-Amino-4-(1,3-dihydroisoindole-2-carbonyl)quinazolin-6-yl]-N,N-diethyl-4-fluorobenzamide |
| "A71" | 2-[2-Amino-4-(1,3-dihydroisoindole-2-carbonyl)quinazolin-6-yl]-N,N-diethyl-5-fluorobenzamide |
| "A72" | {2-Amino-6-[2-((S)-2-methylpyrrolidine-1-carbonyl)phenyl]-quinazolin-4-yl}-(1,3-dihydroisoindol-2-yl)methanone |
| "A73" | 2-[2-Amino-4-(1,3-dihydroisoindole-2-carbonyl)quinazolin-6-yl]-N,N-bis-(2-hydroxyethyl)benzamide |
| "A74" | 2-[2-Amino-4-(1,3-dihydroisoindole-2-carbonyl)quinazolin-6-yl]-N-ethyl-4,5-difluorobenzamide |
| "A75" | 2-[2-Amino-4-(1,3-dihydroisoindole-2-carbonyl)quinazolin-6-yl]-N-ethyl-4,5-difluoro-N-(2-hydroxyethyl)benzamide |
| "A76" | 2-[2-Amino-4-(1,3-dihydroisoindole-2-carbonyl)quinazolin-6-yl]-N-(2-dimethylaminoethyl)-N-ethyl-4,5-difluorobenzamide |
| "A77" | 2-[2-Amino-4-(1,3-dihydroisoindole-2-carbonyl)quinazolin-6-yl]-N-ethyl-4,5-difluoro-N-methylbenzamide |
| "A78" | {2-Amino-6-[4,5-difluoro-2-(pyrrolidine-1-carbonyl)phenyl]-quinazolin-4-yl}-(1,3-dihydroisoindol-2-yl)methanone |
| "A79" | {2-Amino-6-[4,5-difluoro-2-(2-methylpyrrolidine-1-carbonyl)-phenyl]quinazolin-4-yl}-(1,3-dihydroisoindol-2-yl)methanone |
| "A80" | {2-Amino-6-{2-(azetidine-1-carbonyl)-4,5-difluorophenyl]-quinazolin-4-yl}-(1,3-dihydroisoindol-2-yl)methanone |
| "A81" | 2-[2-Amino-4-(1,3-dihydroisoindole-2-carbonyl)quinazolin-6-yl]-N-tert-butyl-4,5-difluorobenzamide |

| Compound No. | Structure and/or name |
|---|---|
| "A82" | 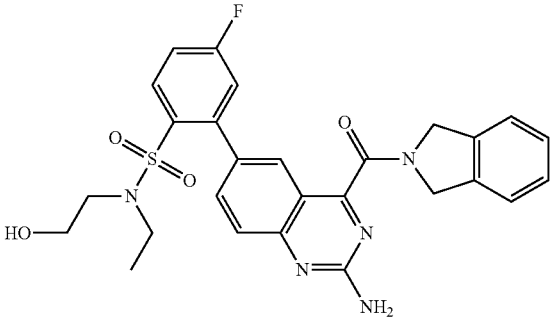<br>2-[2-Amino-4-(1,3-dihydroisoindole-2-carbonyl)quinazolin-6-yl]-N-ethyl-4-fluoro-N-(2-hydroxyethyl)benzenesulfonamide |
| "A83" | 2-[2-Amino-4-(1,3-dihydroisoindole-2-carbonyl)quinazolin-6-yl]-N-ethyl-5-fluorobenzamide |
| "A84" | 2-[2-Amino-4-(1,3-dihydroisoindole-2-carbonyl)quinazolin-6-yl]-N-ethyl-4,5-dimethoxybenzamide |
| "A85" | 2-[2-Amino-4-(1,3-dihydroisoindole-2-carbonyl)quinazolin-6-yl]-N-tert-butyl-4,5-dimethoxybenzamide |
| "A86" | 2-[2-Amino-4-(1,3-dihydroisoindole-2-carbonyl)quinazolin-6-yl]-4-chloro-N-ethylbenzamide |
| "A87" | 2-[2-Amino-4-(1,3-dihydroisoindole-2-carbonyl)quinazolin-6-yl]-4-chloro-N,N-diethylbenzamide |
| "A88" | 2-[2-Amino-4-(1,3-dihydroisoindole-2-carbonyl)quinazolin-6-yl]-N,N-diethyl-4,5-dimethoxybenzamide |
| "A89" | 2-[2-Amino-4-(1,3-dihydroisoindole-2-carbonyl)quinazolin-6-yl]-N-tert-butyl-4-chlorobenzamide |
| "A90" | 2-[2-Amino-4-(1,3-dihydroisoindole-2-carbonyl)quinazolin-6-yl]-4-chloro-N-ethyl-N-(2-hydroxyethyl)benzamide |
| "A91" | {2-Amino-6-[4,5-difluoro-2-(4-methylpiperazine-1-sulfonyl)-phenyl]quinazolin-4-yl}-(1,3-dihydroisoindol-2-yl)methanone |
| "A92" | {2-Amino-6-[2-(3,4-dimethylpiperazine-1-sulfonyl)-4,5-difluorophenyl]quinazolin-4-yl}-(1,3-dihydroisoindol-2-yl)-methanone |
| "A93" | {2-Amino-6-[4,5-difluoro-2-(4-hydroxypiperidine-1-sulfonyl)-phenyl]quinazolin-4-yl}-(1,3-dihydroisoindol-2-yl)methanone |
| "A94" | {2-Amino-6-[4,5-difluoro-2-(piperazine-1-sulfonyl)phenyl]-quinazolin-4-yl}-(1,3-dihydroisoindol-2-yl)methanone |
| "A95" | {2-Amino-6-[5-butoxy-4-fluoro-2-(piperazine-1-sulfonyl)-phenyl]quinazolin-4-yl}-(1,3-dihydroisoindol-2-yl)methanone |
| "A96" | 2-[2-Amino-4-(1,3-dihydroisoindole-2-carbonyl)quinazolin-6-yl]-4,5-difluorobenzenesulfonic acid |
| "A97" | 2-[2-Amino-4-(1,3-dihydroisoindole-2-carbonyl)quinazolin-6-yl]-N-ethyl-4,5-difluoro-N-(2-hydroxyethyl)benzenesulfonamide |
| "A98" | {2-Amino-6-[4,5-difluoro-2-(pyrrolidine-1-sulfonyl)phenyl]-quinazolin-4-yl}-(1,3-dihydroisoindol-2-yl)methanone |
| "A99" | 2-[2-Amino-4-(1,3-dihydroisoindole-2-carbonyl)quinazolin-6-yl]-N-tert-butyl-4,5-difluoro-N-methylbenzenesulfonamide |
| "A100" | {2-Amino-6-[2-(3,3-difluoropyrrolidine-1-sulfonyl)-4,5-difluorophenyl]quinazolin-4-yl}-(1,3-dihydroisoindol-2-yl)-methanone |
| "A101" | {2-Amino-6-[4,5-difluoro-2-(3-hydroxypyrrolidine-1-sulfonyl)-phenyl]quinazolin-4-yl}-(1,3-dihydroisoindol-2-yl)methanone |
| "A102" | {2-Amino-6-[4,5-difluoro-2-(3-methylpiperazine-1-sulfonyl)-phenyl]quinazolin-4-yl}-(1,3-dihydroisoindol-2-yl)methanone |
| "A103" | {2-Amino-6-[4,5-difluoro-2-(3-trifluoromethylpiperazine-1-sulfonyl)phenyl]quinazolin-4-yl}-(1,3-dihydroisoindol-2-yl)-methanone |
| "A104" | {2-Amino-6-[2-(3,5-dimethylpiperazine-1-sulfonyl)-4,5-difluorophenyl]quinazolin-4-yl}-(1,3-dihydroisoindol-2-yl)-methanone |
| "A105" | 2-[2-Amino-4-(1,3-dihydroisoindole-2-carbonyl)quinazolin-6-yl]-4,5-difluorobenzoic acid | and pharmaceutically usable salts, tautomers and stereoisomers thereof, including mixtures thereof in all ratios.

11. Process for the preparation of compounds of the formula I according to claim 1 and pharmaceutically usable salts, tautomers and stereoisomers thereof, characterised in that
a) a compound of the formula II

[Structure II: quinazoline with -C(=O)-N-isoindoline substituent bearing R¹, a phenyl group with R², R³ substituents and L-X group, and 2-amino group]

in which
R¹, R², R³ and X have the meanings indicated in claim 1, and L denotes F, Cl, Br, I or a free or reactively modified OH group,
is reacted with a compound of the formula III

NHR⁴R⁵        III in which
R⁴ and R⁵ have the meanings indicated in claim 1,
or
b) a compound of the formula IV

[Structure IV: phenyl ring with R², R³ substituents, N(R⁴)(R⁵)-X group and Hal]

in which X, R², R³, R⁴ and R⁵ have the meanings indicated in claim 1,
and Hal denotes bromine or iodine,
is reacted with a compound of the formula V

[Structure V: quinazoline with -C(=O)-N-isoindoline substituent bearing R¹, an L group, and 2-amino group]

in which R¹ has the meaning indicated in claim 1,
and L denotes a boronic acid or boronic acid ester radical,
or
c) a compound of the formula VI

[Structure VI: phenyl ring with R², R³ substituents, N(R⁴)(R⁵)-X group and L]

in which X, R², R³, R⁴ and R⁵ have the meanings indicated in claim 1 and
L denotes a boronic acid or boronic acid ester radical,
is reacted with a compound of the formula VII

[Structure VII: quinazoline with -C(=O)-N-isoindoline substituent bearing R¹, Hal group, and 2-amino group]

in which R¹ has the meaning indicated in claim 1,
and Hal denotes bromine or iodine,
and/or a base or acid of the formula I is converted into one of its salts.

12. Medicaments comprising at least one compound according to claim 1 and/or pharmaceutically usable salts, tautomers and stereoisomers thereof, including mixtures thereof in all ratios, and optionally excipients and/or adjuvants.

13. A method of treating a disease in which the inhibition, regulation and/or modulation of HSP90 plays a role, said method comprising administering and effective amount of a compound of formula I according to claim 1, or a pharmaceutically acceptable salt, tautomer or stereoisomer thereof, including mixtures thereof in all ratios, to a patient in need thereof.

14. A method according to claim 13 wherein the disease that is treated is selected from tumour diseases, viral diseases, inflammation-induced diseases, cystic fibrosis, diseases associated with angiogenesis, infectious diseases, autoimmune diseases, ischaemia, fibrogenetic diseases,
    the growth of cancer, the growth of tumour cells, tumour metastases, and
    diseases in which incorrect protein folding or aggregation is a principal causal factor.

15. A method according to claim 14, where the tumour diseases are fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease.

16. A method according to claim 14, where the viral pathogen of the viral diseases is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, hantavirus, Coxsackie virus, mumps virus, measles virus, rubella virus, polio-virus, human immunodeficiency virus type I (HIV-I) and human immunodeficiency virus type II (HIV-II).

17. A method according to claim 14, where the inflammation-induced diseases are rheumatoid arthritis, sepsis, asthma, multiple sclerosis, type 1 diabetes, lupus erythematosus, psoriasis and inflammatory bowel disease.

18. A method according to claim 14, where the diseases associated with angiogenesis are diabetic retinopathy, haemangiomas, endometriosis and tumour angiogenesis.

19. A method according to claim 14, where the fibrogenetic diseases are scleroderma, polymyositis, systemic lupus, cirrhosis of the liver, keloid formation, interstitial nephritis and pulmonary fibrosis.

20. A method according to claim 14, where the diseases in which incorrect protein folding or aggregation is a principal causal factor is scrapie, Creutzfeldt-Jakob disease, Huntington's or Alzheimer's.

21. Medicament comprising at least one compound according to claim 1 and/or pharmaceutically usable salts, tautomers and stereoisomers thereof, including mixtures thereof in all ratios, and at least one further medicament active ingredient.

22. Set (kit) consisting of separate packs of
(a) effective amount of a compound according to claim 1 and/or pharmaceutically usable salts, tautomers and stereoisomers thereof, including mixtures thereof in all ratios,
and
(b) an effective amount of a further medicament active ingredient.

23. Compounds of the formula II

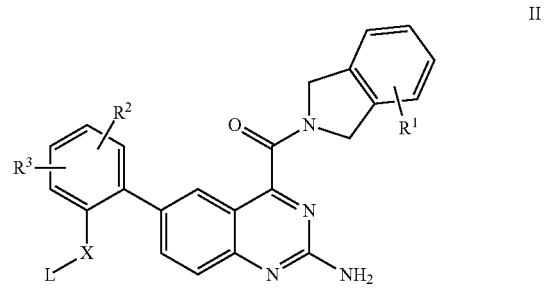

in which
$R^1$ denotes H, Hal or A,
$R^2$, $R^3$ each, independently of one another, denote H, Hal, OH or OA,
X denotes CO or $SO_2$,
A denotes unbranched or branched alkyl having 1-6 C atoms, in which 1-2 non-adjacent $CH_2$ groups may be replaced by O, NH, NMe or NEt and/or, in addition, 1-5 H atoms may be replaced by F and/or Cl,
or cyclic alkyl having 3-8 C atoms,
L denotes F, Cl, Br, I or a free or reactively modified OH group,
and salts thereof.

* * * * *

UNITED STATES PATENT AND TRADEMARK OFFICE
CERTIFICATE OF CORRECTION

| | | |
|---|---|---|
| PATENT NO. | : 8,546,565 B2 | Page 1 of 1 |
| APPLICATION NO. | : 13/133495 | |
| DATED | : October 1, 2013 | |
| INVENTOR(S) | : Hans-Michael Eggenweiler et al. | |

It is certified that error appears in the above-identified patent and that said Letters Patent is hereby corrected as shown below:

On title page, Item (73) Assignee: reads "Merck Patent Gesellschaft", should read --Merck Patent Gesellschaft Mit Beschrankter Hafting--;

In the Claims:

Column 98, line 42, after "pyrrolyl", insert --imidazolyl--.

Signed and Sealed this
Eleventh Day of February, 2014

Michelle K. Lee
*Deputy Director of the United States Patent and Trademark Office*